United States Patent
Garbark et al.

(10) Patent No.: US 12,351,539 B2
(45) Date of Patent: Jul. 8, 2025

(54) BIO-BASED SURFACTANTS

(71) Applicant: Battelle Memorial Institute, Columbus, OH (US)

(72) Inventors: Daniel B. Garbark, Columbus, OH (US); Jeffrey T. Cafmeyer, Columbus, OH (US); Manoj Kumar Valluri, Columbus, OH (US); Phillip Denen, Columbus, OH (US); Albert J. Darling, Columbus, OH (US)

(73) Assignee: Battelle Memorial Institute, Columbus, OH (US)

(*) Notice: Subject to any disclaimer, the term of this patent is extended or adjusted under 35 U.S.C. 154(b) by 463 days.

(21) Appl. No.: 17/482,344

(22) Filed: Sep. 22, 2021

(65) Prior Publication Data
US 2022/0089983 A1     Mar. 24, 2022

Related U.S. Application Data

(60) Provisional application No. 63/081,875, filed on Sep. 22, 2020.

(51) Int. Cl.
*C07C 231/14* (2006.01)
*C11D 1/52* (2006.01)
(Continued)

(52) U.S. Cl.
CPC ............ *C07C 231/14* (2013.01); *C11D 1/523* (2013.01); *C11D 1/662* (2013.01); *C11D 1/90* (2013.01); *C11D 1/92* (2013.01); *C11D 2111/12* (2024.01)

(58) Field of Classification Search
None
See application file for complete search history.

(56) References Cited

U.S. PATENT DOCUMENTS 3,138,566 A    6/1964 Arnold
6,204,238 B1 *  3/2001 Oftring ............... C11D 1/528
                                                510/502
(Continued)

FOREIGN PATENT DOCUMENTS

CA     731107 A      3/1966
WO     2020058664 A1  3/2020
WO     2021116500 A1  6/2021

OTHER PUBLICATIONS

International Search Report from International Application No. PCT/US2021/051616, date of mailing Feb. 7, 2022.
(Continued)

*Primary Examiner* — Necholus Ogden, Jr.
(74) *Attorney, Agent, or Firm* — Susanne A. Wilson; Frank Rosenberg

(57) ABSTRACT

Bio-based surfactants have great opportunity for use in a variety of applications such as laundry detergents, industrial cleaners, adjuvants, and oil & gas. Surfactants in these applications can be nonionic, anionic, cationic, or amphoteric. Utilizing high oleic soybean oil as a platform chemical, a variety of surfactants and properties can be produced. While early work focused solely on surfactant use in laundry cleaning and fracking, recent work has expanded functional groups and application evaluations in hard surface cleaning. The current invention expands on Battelle's high oleic soybean oil (HOSO) surfactant technology. Use of HOSO overcomes the limitations of regular soybean oil and significantly reduces or eliminates undesirable byproducts in most chemistries. However, with use of select reagents, a few candidates were achievable with regular epoxidized soybean oil (ESO). The HOSO surfactant platform offers several key advantages including: a highly water miscible (not typical of C18 surfactants) and water stable surfactant; ability to adjust and vary hydrophilic-lipophilic (HLB) val-
(Continued)

ues for stain removal performance; and increased biodegradability without toxic or persistent by-products.

19 Claims, 2 Drawing Sheets

(51) Int. Cl.
*C11D 1/66* (2006.01)
*C11D 1/90* (2006.01)
*C11D 1/92* (2006.01)

(56) References Cited

U.S. PATENT DOCUMENTS

| | | |
|---|---|---|
| 6,797,684 B2 | 9/2004 | Henneberry et al. |
| 7,951,766 B1 | 5/2011 | Frenkel |
| 9,085,709 B1 | 7/2015 | Lele |
| 11,168,284 B2 | 11/2021 | Garbark et al. |
| 2017/0044090 A1 | 2/2017 | Benecke |

OTHER PUBLICATIONS

Written Opinion of the International Search Authority from International Application No. PCT/US2021/051616, date of mailing Feb. 7, 2022.

\* cited by examiner

BIO-BASED SURFACTANTS

RELATED APPLICATIONS

This application claims the priority benefit of U.S. Provisional Patent Application Ser. 63/081,875 filed 22 Sep. 2020.

SUMMARY OF THE INVENTION

The invention includes any of the compounds described or drawn herein. The invention also includes surfactant compositions, laundry detergent compositions, general cleaners, dishwasher detergent, kitchen cleaners, dish cleaners, industrial cleaners, and/or adjuvants comprising one or any combination of the compounds described herein. The invention also includes methods of cleaning using a cleaning formulation comprising one or any combination of the compounds described herein.

In one aspect, the invention provides a composition, comprising one or more compounds selected from candidates 14-32, 34-48, and 50-55. In some preferred embodiments, the composition comprises one or any combination of the following characteristics: at least 0.5 wt % (or at least 1, at least 2, or at least 5 wt %) of one or more compounds selected from candidates 14-32, 34-48, and 50-55; the composition comprising one or more compounds selected from candidates 14-32, 34-48, and 50-55 mixed with SDBS in a weight ratio in the range of 1:10 to 10:1 or 2:1 to 1:2; wherein the one or more compounds is at least 50% biobased carbon, or at least 70% biobased carbon; comprising any candidate or combination of candidates selected from the above list; for example, one or more of candidates 25, 32, 43, and 48. The invention also includes an intermediate composition comprising one or more compounds selected from candidates 14-32, 34-48, and 50-55. The invention also includes a method of washing laundry, comprising contacting dirty laundry with any composition of the invention; the invention similarly includes methods of washing hair, or methods of washing a floor or other surfaces.

In another aspect, the invention comprises a surfactant compound, comprising: a C18 carbon chain moiety comprising a ketone moiety (C=O) at one end of the C18 carbon chain moiety and a OH moiety in the middle of the C18 carbon chain moiety; and further: wherein the surfactant compound comprises a betaine surfactant comprising a quarternary ammonium; or wherein the surfactant compound comprises a hydroxysultaine surfactant comprising a quarternary ammonium; or wherein the surfactant compound comprises an alkoxyamide surfactant; or wherein the surfactant compound comprises a glucoside or polyglucoside surfactant; or wherein the surfactant compound comprises a chelating surfactant comprising a polyether sidechain connected via an ether linkage to the C18 carbon chain moiety or a polyamine sidechain connected via an amine linkage to the C18 carbon chain moiety. In some preferred embodiments, the composition comprises one or a combination of the following characteristics: wherein the OH moiety is bonded to the $10^{th}$ carbon of the carbon chain, wherein the first carbon is the carbon of the C=O moiety; comprising a betaine surfactant based on functionalized epoxidized high oleic soybean oil. In the present invention, high oleic soybean oil comprises at least 50% wt % or at least 70 wt % or 70 to 99 wt % oleic acid or other oleate; comprising a hydroxysultaine surfactant based on functionalized epoxidized soybean oil; comprising a hydroxysultaine surfactant based on functionalized epoxidized high oleic soybean oil; comprising a hydroxyalkylamide surfactant based on functionalized epoxidized soybean oil; comprising a hydroxyalkylamide surfactant based on functionalized epoxidized high oleic soybean oil; comprising a betaine surfactant containing a betaine functionality at the fatty acid salt at the original fatty acid carboxyl group; comprising a chelating surfactant based on functionalized epoxidized soybean oil; comprising a chelating surfactant based on functionalized epoxidized high oleic soybean oil; comprising a betaine surfactant based on functionalized epoxidized soybean oil.

In a further aspect, the invention provides a method of making a surfactant, comprising: providing an oil comprising at least 50% wt % or at least 70 wt % or 70 to 99 wt % oleic acid or other oleate; reacting the oleic acid or other oleate to form an epoxide; reacting the epoxide with an alcohol to form an ether; and reacting with an amide to form a C(O)N moiety. In another aspect, the invention provides a method of making a surfactant, comprising: providing an oil comprising at least 50% wt % or at least 70 wt % or 70 to 99 wt % oleic acid or other oleate; reacting the oleic acid or other oleate in a hydroformylation reaction followed by hydrogenation to form a hydroxymethyl group at the original double bond of the oleic acid or other oleate; and reacting with a sulfonic acid. In another aspect, the invention provides a method of making a surfactant, comprising: providing a compound comprising a C18 carbon chain moiety comprising a ketone moiety (C=O) at one end of the C18 carbon chain moiety and a OH moiety in the middle of the C18 carbon chain moiety; reacting with an amine or amide to form an amide-containing derivative, and reacting the amide-containing derivative with a halogenated acid to produce a betaine. In a further aspect, the invention provides a method of making a surfactant, comprising: providing a first compound comprising a C18 carbon chain moiety comprising a ketone moiety (C=O) at one end of the C18 carbon chain moiety and a OH moiety in the middle of the C18 carbon chain moiety; reacting the OH moiety with a diol, such as a polyalkyl glycol, to form a hydroxyl-functionalized product; and reacting the hydroxyl-functionalized product with a second compound comprising a C18 carbon chain moiety comprising a ketone moiety (C=O) at one end of the C18 carbon chain moiety and a OH moiety in the middle of the C18 carbon chain moiety. In any of the inventive methods, the invention can be further characterized by one or any combination of the following characteristics: wherein the alcohol comprises a diol or a dialkylaminoalcohol such as dimethylaminoethanol; wherein the diol comprises polyalkylene glycol such as polyethylene glycol or polypropylene glycol; wherein the amide has the structure $HNR^1R^2$ wherein $R^1$ is selected from the group consisting of H and C1 to C6 alkyl or substituted alkyl and wherein $R^2$ is selected from the group consisting C1 to C6 alkyl or substituted alkyl; wherein the amide is dimethylaminopropylamine; wherein the $R^1$ or $R^2$ comprises an amide moiety and further comprising reacting to form a betaine; and/or wherein the OH moiety is bonded to the $10^{th}$ carbon of the carbon chain, wherein the first carbon is the carbon of the C=O moiety.

In another aspect, the invention provides an intermediate structure, comprising

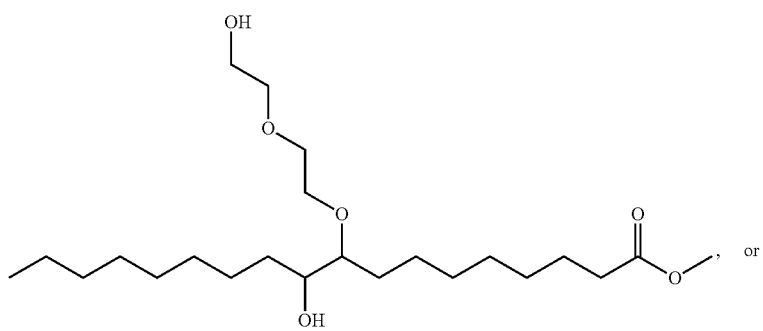

Candidate 25 Intermediate 1

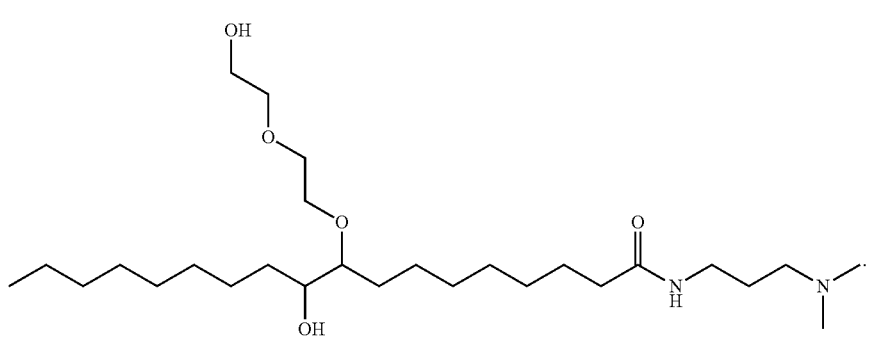

Candidate 25 Intermediate 2

In one aspect, the invention comprises a surfactant composition comprising:

This compound can be calculated at 56.8% biobased based on molecular weight or 81.8% biobased carbon based on the carbon content from soybean oil versus the total carbon.

The invention also provides an intermediate structure, comprising a dimethylaminoamide, ester, polyamine amide, and/or polyamine on the fatty acid after functionalization of the epoxide. The invention further provides a surfactant based on hydroformylated and hydrogenated high oleic soybean oil. The invention also provides a glucoside or polyglucoside based on any hydroxylated intermediate from any of the candidates described herein. The invention also provides a glucoside or polyglucoside based on an alkoxy diol or polyol ring opened epoxidized high oleic soybean oil.

Any aspect of the invention may also be described by one or any combination of the test results reported herein, or ±10%, or ±20%, or ±30% of one or any combination of the test results reported herein. The compounds and intermediates herein preferably contain a carbon content that is at least 50% or 100% biobased. The compounds and intermediates are preferably derived from soybeans. Note that bio-based compositions can be identified by knowledge of their derivation or $^{14}C$ levels as is known in the literature. Any of the compounds can be further characterized by one or any combination of the results described herein (or within ±10%, or ±20%, or ±30% of the results described herein).

The superior results observed for some of the compounds was a surprising result of our research.

The invention also includes the methods of making the compounds and intermediates described herein. The invention also includes the intermediates described herein. The invention also includes surfactants (or detergents, etc.) made by reaction chemistries of the types described herein; for example, surfactants made by a process comprising reacting chlorosulfonic acid with epoxidized high oleic soybean oil methyl ester (MeEHOSO). The invention includes any of the methods described herein and generalized methods based on the methods described herein. The invention also includes compounds made by any of the methods described herein or generalized methods based on the methods described herein.

DETAILED DESCRIPTION OF THE INVENTION

Figure 1:
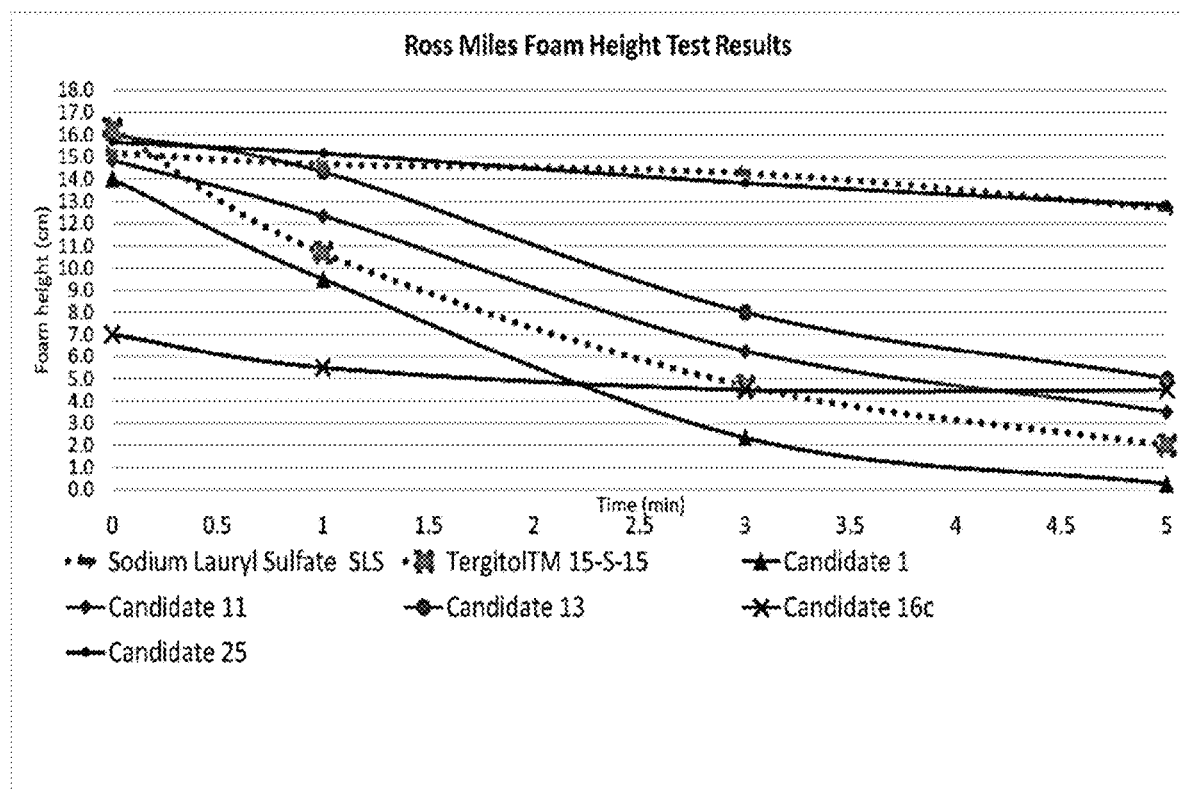
FIG. 1 shows anti-foaming performance of selected surfactants.

Earlier work by Battelle is described in US Patent Application US 2019/0177655 A1 "Laundry Builders and Surfactants Derived from Bio-Based Hydroxy-Acids and Epoxides", which is incorporated herein as if reproduced in full below. An approach for synthesizing epoxidized HOSO based surfactants is to build molecular weight through reactions at the epoxide site and/or the fatty acid site. Through a series of reactions with a variety of components, surfactants with various functional groups can be produced while maintaining the original fatty acid backbone. This important trait allows us to tailor functional groups for improved performance for any given application. We can further target a wide range of hydrophilic-lipophilic balance (HLB) which results in controlling or altering properties such as octanol/water partition coefficient and surface tension. The main reason C18 surfactants are not typically used is due to their lower solubility in water. For example, sodium oleate (a common soap), is approximately 10% soluble in water. Sodium stearate, however, is fully water soluble but solubility is very sensitive to water temperature. A more direct comparison would be that of stearamidopropyl betaine. Stearamidopropyl betaine has a water solubility of 1.6 mg/L. Our functionalized betaine candidates are fully water miscible and are typically produced at 45% in water.

The advent of high oleic soybean oil availability has changed the range of applications versus commodity soybean oil. HOSO is utilized due to the reduced side reactions that take place when reacting with ESO. The process for inter- and intra-molecular reactions can be seen below.

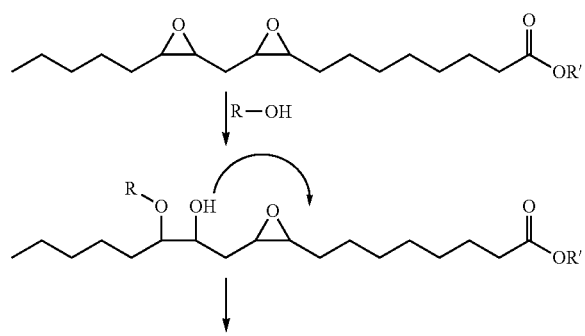

-continued

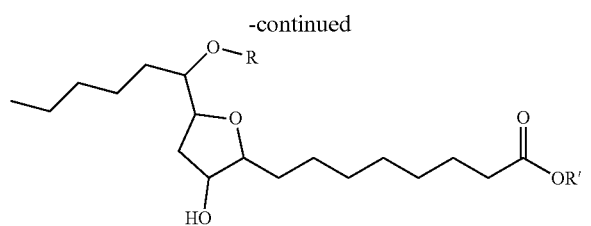

When reacting a hydroxyl group, containing reduced reactivity, across the fatty acid ester epoxides of fatty acid esters such as those from linoleic acid and linolenic acid, a tetrahydrofuran group or an oligomer of multiple fatty acid esters can form. After saponification, this detrimental group of reactions cause gel particles to form in water. However, when using higher amounts of reagents and select chemistries, we can utilize ESO. This is typically the case when reacting alcohols containing highly reactive hydroxyls such as ethyl cellosolve or triethylene glycol.

Hard Surface Cleaning

A wide variety of functionalities are used in surfactants for hard surface cleaning. Hard surface cleaners are used to remove dust, dirt, and stains and are even used in some health and beauty applications. They typically consist of non-ionic surfactants but can also include anionic and amphoteric surfactants in some cases. One hard surface surfactant is that of cocamide diethanolamine (DEA). Cocamide DEA is used in a variety of applications such as cosmetics, hand soaps, and shampoos. Cocamide DEA is listed in California Prop 65 as a known cancer-causing agent. Recently, there has also been concerns in the long-term supply and sustainability of coconut fatty acids. We have developed novel alternatives to cocamide DEA. Initially, we produced candidates for the main purpose of replacing diethanolamide functionalized coconut fatty acids (cocamide DEA). Candidate 22 is produced by first ring opening epoxidized high oleic soybean oil (EHOSO) with ethanol followed by amidification with diethanolamine. The resulting structure can be found below. Alternatively, methanol can also be used (produced and named Candidate 49). Further, any hydroxyalkylamine could be used in place of diethanolamine. Some examples of hydroxyalkylamines, including but not limited to, are ethanolamine, 2-(methylamino)ethanol, 2-(ethylamino)ethanol, tris(hydroxymethyl)aminomethane, 1-aminopropan-2-ol, and di-isopropanolamine.

Candidate 22

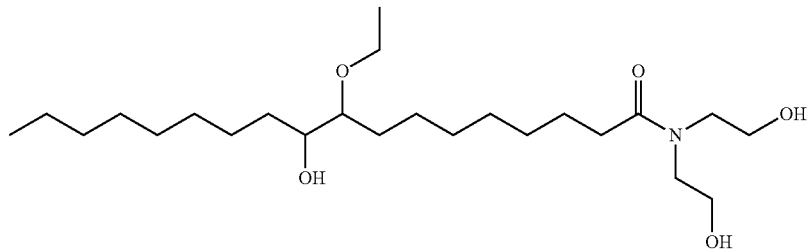

Another compound was produced by ring opening and amidifying both reactive sites with ethanolamine to obtain Candidate 23 seen below.

Candidate 23

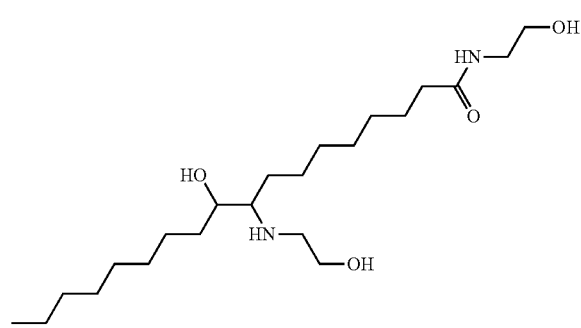

A third replacement was produced by reacting the epoxide with propylene glycol followed by amidification of the fatty acid ester with ethanolamine. This structure can be seen below.

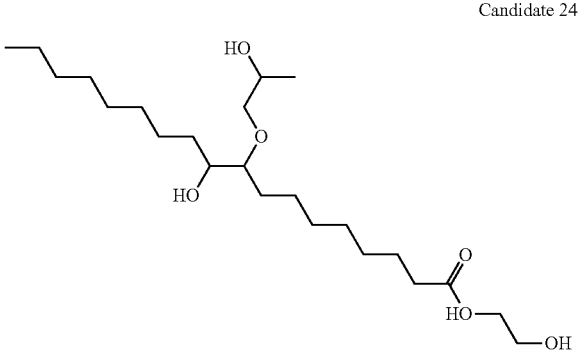 [SMILES: CCCCCCCCC(O)C(CCCCCCCC(=O)OCCO)OCC(C)O]

Candidate 24

Other candidates can be produced by varying the reactants for both the ring opening and carboxylic acid sites. Other potential candidates are listed later in this application and include chelating surfactants. The important factor for cleaners is varying components in a manner that maintains water miscibility or dispersibility. Choosing the incorrect reactants can lead to a surfactant that will maintain greater hydrophobicity. This lack of miscibility would be fine for some applications, but unsuitable for others. Reactions that first ring open the epoxide with a highly reactive material, such as ethanol, can be used to produce derivates from regular ESO without the undesirable side reactions (cyclization and cross-linking). The general formulation for ESO can be seen below.

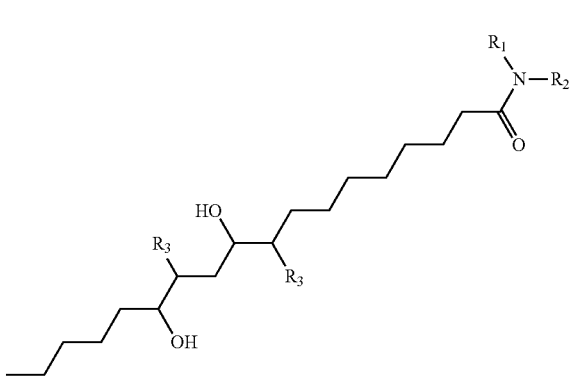

General Structure for ESO-Based Hard Surface Cleaning Surfactant

In compounds of the present invention, R1 and R2 could be hydrogen, methoxy, ethoxy, propoxy, isopropoxy, tris (hydroxymethyl), or any mixture thereof. R3 would require very reactive materials to limit side reactions. R3 could be methoxy, ethoxy, propoxy, alkoxy, or the reaction product of alkyl alcohol, poly-hydroxyl, polypropylene glycol, poly-ethylene glycol, propylene glycol mono-ether, ethyelene glycol mono-ether, polypropylene glycol mono-ether, poly-ethylene glycol mono-ether, polyamine, or amine carboxylates; preferably primary hydroxyl containing materials such as methanol or ethanol and may also contain poly-hydroxyl containing material such as polypropylene glycol or poly-ethylene glycol or monoethers thereof. For the sake of maintaining the overall biobased content, we limited the polyalkylene glycols and monoethers to four repeating units or less.

Another, non-amide, candidate was produced by reacting dipropylene glycol mono-methyl ether with epoxidized high oleic soybean oil (EPHOSO) followed by saponification of the fatty acid ester. The idealized structure can be seen below.

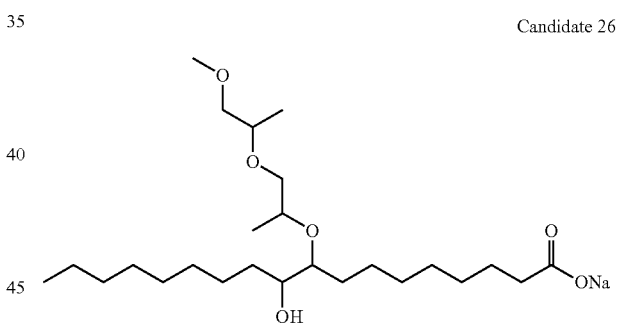

Candidate 26

A formulation utilizing cocamide DEA was used as a standard for hard surface cleaning evaluation. Cocamide DEA was then replaced on a weight-to-weight basis in the formulation for three stain types. The results can be seen in the table below.

| Soil | Type | Substrate | Cocamide DEA | Can. 22 | Can. 1 | Can. 4 | Can. 13 | Sig. Dif. |
|---|---|---|---|---|---|---|---|---|
| ASTM D4488-A3 | Grime | Vinyl Tile | 76.5 | 74.2 | 66.7 | 63.9 | 72.5 | 7.2 |
| ASTM D4488-A5 | General Purpose | Vinyl Tile | 89.6 | 89.3 | 83.6 | 85.1 | 83.7 | 4.9 |
| ASTM D4488-A2 | Kitchen Grease | Wallboard | 35.6 | 31.5 | 31.2 | 28.3 | 19.8 | 3.4 |
| Overall Soil Removal Totals | | | 201.7 | 195 | 181.5 | 177.3 | 176 | |
| % of Best | | | Best | 96.70% | 90.00% | 87.90% | 87.30% | | grease. It is interesting to note that Candidate 1 (described in US 2019/0177655) is produced from the reaction of citrate and EHOSO which does not contain a nitrogen group. The other two candidates, 4 and 13 also described in US2019/0177655, were slightly deficient.

For the second evaluation, we used an alternative formulation that utilized a standard non-ionic surfactant alcohol ethoxylate Tergitol™ 15-s-15. The Tergitol™ was replaced on a weight-to-weight basis in the formulation. Results can be seen below.

| Soil | Type | Substrate | Tergitol 15-s-15 Standard | Can. 25 | Can. 1 | Can. 4 | Sig. Dif. |
|---|---|---|---|---|---|---|---|
| ASTM D4488-A3 | Grime | Vinyl Tile | 33.7 | 39.9 | 22.5 | 6.5 | 3.2 |
| ASTM D4488-A5 | General Purpose | Vinyl Tile | 23.6 | 22.1 | 21 | 23. | 7.3 |
| ASTM D4488-A2 | Kitchen Grease | Wallboard | 6.7 | 3.5 | 20.1 | 3.6 | 8.6 |
| Overall Soil Removal Totals | | | 64.0 | 65.5 | 63.6 | 33.1 | 19.1 |
| % of Best | | | 100 | 102.3% | 99.4% | 51.7% | |

As seen in the table, Candidate 1 and the amphoteric Candidate 25 (described later in this application) performed equivalent to the Tergitol™. Candidate 4, which contains a triethylene glycol group, did not perform well on grime. Candidate 1 performed exceptionally well on kitchen grease. Overall, the data shows that our technology can produce soy-based compounds effective for use in hard surface cleaning.

Other Applications

In considering both laundry and hard surface applications, other candidates were also produced. The first candidate was produced to be an amphoteric replacement for the anionic surfactant component in laundry detergent (sodium dodecylbenzenesulfonate; SDBS). Candidate 25 was produced by first ring opening EHOSO with diethylene glycol. The intermediate 1 was then amidified with dimethylaminopropylamine to produce intermediate 2.

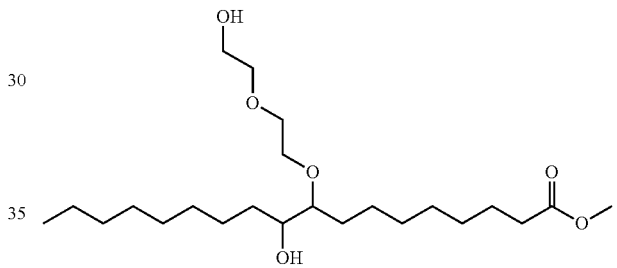

Candidate 25 Intermediate 1

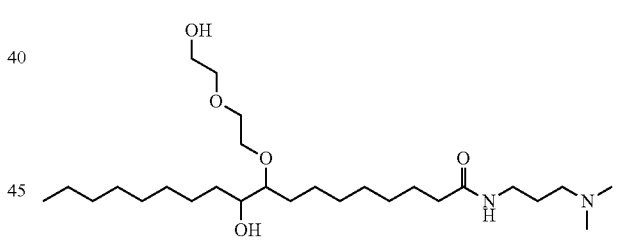

Candidate 25 Intermediate 2

Intermediate 2 was then reacted with chloroacetic acid in the presence of sodium hydroxide and water to produce the amphoteric (zwitterionic) candidate seen below.

Candidate 25

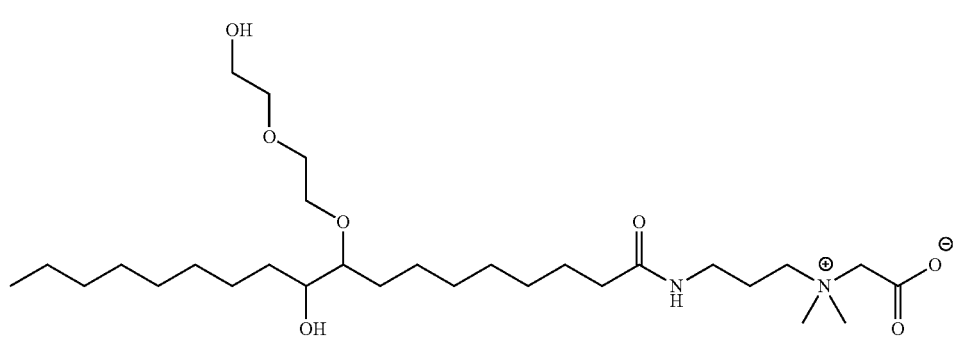

Other variations of these surfactants were produced. One such variation was first reacting with ethyl cellosolve instead of diethylene glycol followed by production of the betaine.

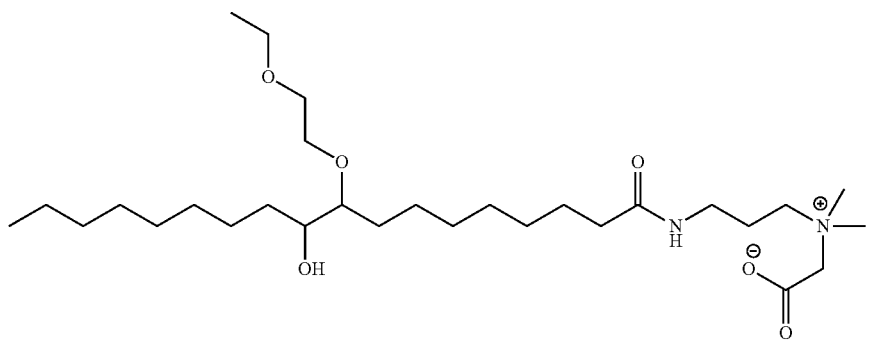

As ethyl cellosolve contains a highly reactive primary hydroxyl, a variation of this candidate was produced from commodity soybean oil. As seen in the structure below, two moles of ethyl cellosolve were required per linoleic acid (on average 1.5 epoxides per fatty acid for commodity soybean oil) leading a lower percent weight of soybean oil in the final surfactant.

When reacting with an oleic epoxy, the aliphatic tail is 8 carbons long. When reacting with a linoleic diepoxy, the aliphatic tail is shorter at 5 carbons. This difference in aliphatic chain length can play a role in the surfactant's performance.

A few more candidates can be seen below. The important factor to producing the zwitterion is having the tetrasubstituted nitrogen compound that is bound to the main structure Candidate 43

Candidate 48 (ESO)

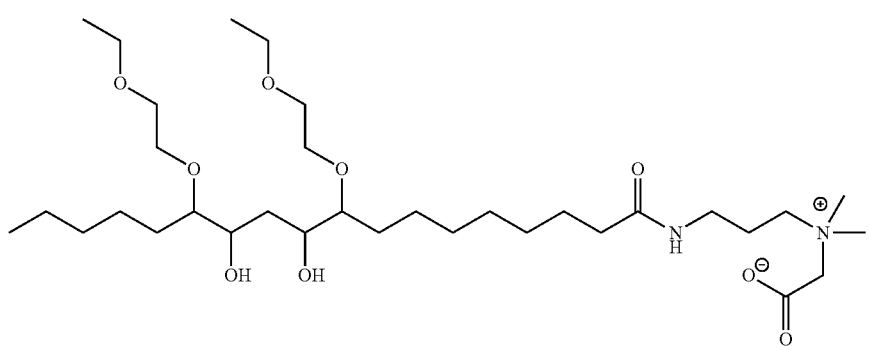

As can be seen in Candidates 43 and 48, there are two distinct differences in using high oleic soybean oil versus conventional soybean oil. The first was mentioned above in the percent weight of soybean oil in the final compound. The second is in the carbon length of the remaining aliphatic tail.

by a basic water stable bond. In soap formulations, an ester would hydrolyze. The betaines can also be produced with other halogenated acids like 2-chloropropionic acids or chloroacetic acid sodium salt. However, we produced betaines from chloroacetic acid initially.

Candidate 27

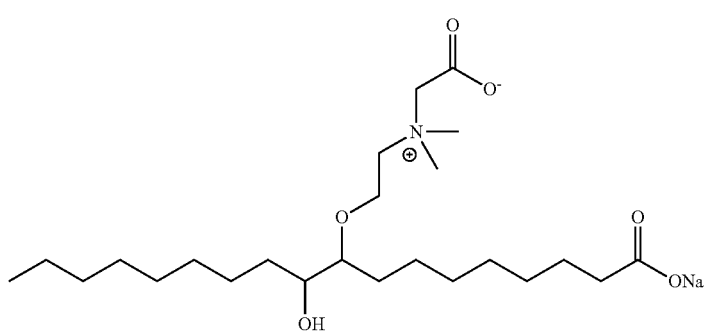

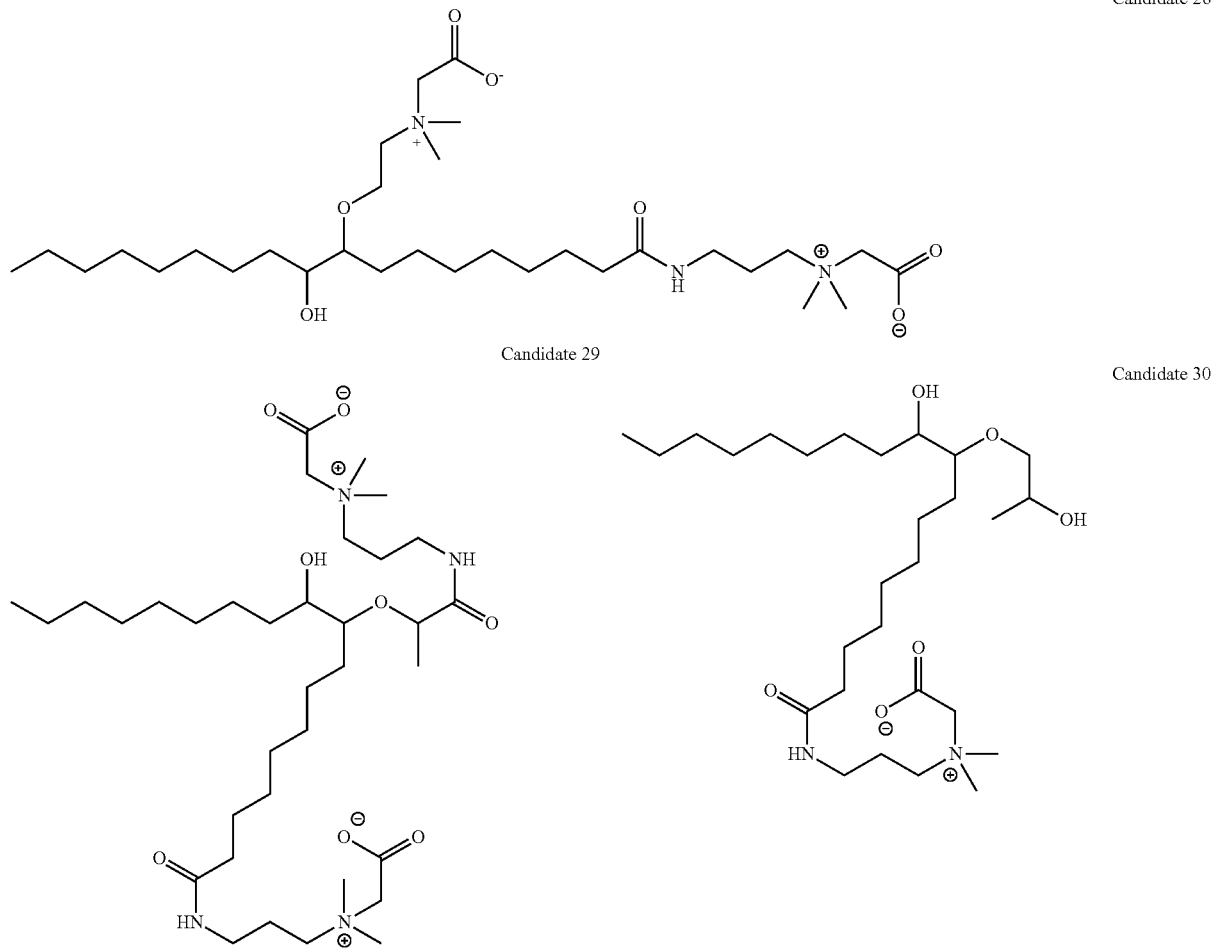

The same process can also be used to produce hydroxysultaines. One candidate produced can be seen below.

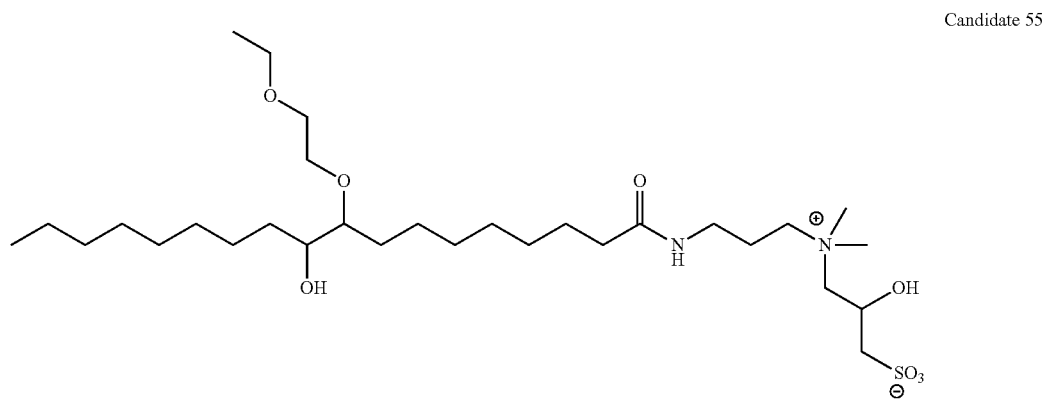

Foam testing of Candidate 25 revealed similar performance to sodium laurylsulfate as seen in FIG. 1.

Select candidates were also evaluated for surface tension. As you can see, some candidates such as 43 performed surprisingly low with a value of 25.5. Many typical laundry surfactants have surface tension (ST) values of 34-45. The results can be seen in the table below.

| | |
|---|---|
| Water | 71.2 |
| Candidate 1 | 32.5 |
| Candidate 2 | 36.6 |

-continued

| | |
|---|---|
| Candidate 4 | 34.5 |
| Candidate 5 | 33.6 |
| Candidate 10 | 32.0 |
| Candidate 11 | 36.5 |
| Candidate 12 | 32.4 |
| Candidate 13 | 35.2 |
| Candidate 14 | 32.0 |
| Candidate 15 | 37.3 |
| Candidate 16 | 39.8 |
| Candidate 25 | 28.2 |
| Candidate 29 | 26.8 |
| Candidate 32 | 27.1 |
| Candidate 39 | 27.1 |
| Candidate 43 | 25.5 |

We next evaluated a few select candidates for evaluation in laundry detergent. The first test was at the same temperature as we have run in the past.

| 90 F Soil | Substrate | Standard 120 mL | Candidate 25 100% SDBS Replacement 120 mL | Pilot Scale Candidate 4 100% Terqitol Replacement 120 mL | Sig. Dif. |
|---|---|---|---|---|---|
| Clay | Cotton | 56 | 50.5 | 54.7 | 3.1 |
| Coffee | Cotton | 42.5 | 43.7 | 43.7 | 2.6 |
| Dust sebum | Cotton | 64.3 | 62.1 | 44.2 | 6.2 |
| EMPA 101 (Olive Oil) | Cotton | 8.7 | 11.1 | 7.6 | 1.7 |
| EMPA 112 (Cocoa) | Cotton | 1.1 | 2 | 8 | 5.2 |
| EMPA 116 (Blood, Milk, Ink.) | Cotton | 12.8 | 10.3 | 11 | 1.7 |
| Grass | Cotton | 47 | 42.6 | 10.9 | 1.6 |
| Makeup | Cotton | 59.2 | 63.7 | 56.3 | 6.5 |
| Red wine | Cotton | 31.5 | 29.8 | 34.5 | 0.9 |
| Spaghetti | Cotton | 85 | 79.2 | 84 | 3.5 |
| Overall Soil Removal Totals | | 408.1 | 395.0 | 354.9 | 33.0 |
| % of Best | | Best | 97% | 87% | |

Candidate 25 was used as a 100% molar replacement of SDBS in a standard formulation. As seen in the table above, Candidate 25 (amphoteric) performed equivalent to the standard SDBS (anionic). This is important as the predicted environmental toxic threshold values (in the EPA ECOSAR model) for Candidate 25 are greater than the SDBS (meaning less toxic).

The invention also includes methods to produce a compound containing a peroxidic site (and the resulting compounds). This was done by reacting epoxidized high oleic soybean oil methyl ester (MeEHOSO) with dimethylaminoethanol to form the ether linkage at the epoxy site. The ether product was then reacted with hydrogen peroxide to oxidize at the dimethylamine site followed by salt formation can be seen in the structure below.

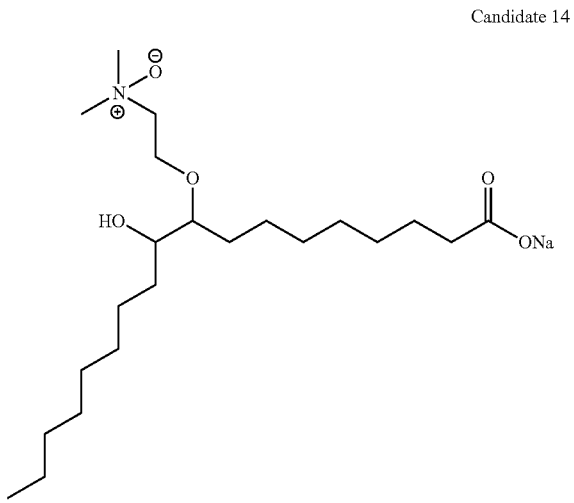

Candidate 14

Another way to change the HLB is to react one fatty acid surfactant with a second epoxide. This is done by first forming the ether at the epoxy site by reacting polyethylene glycol with MeEHOSO. The remaining glycolic hydroxyl can then be reacted with a second MeEHOSO to form a diether with two fatty acids followed by salt formation. This reaction can be performed with any polyethylene glycol. For simplicity, we chose to use triethylene glycol. The structure can be seen below.

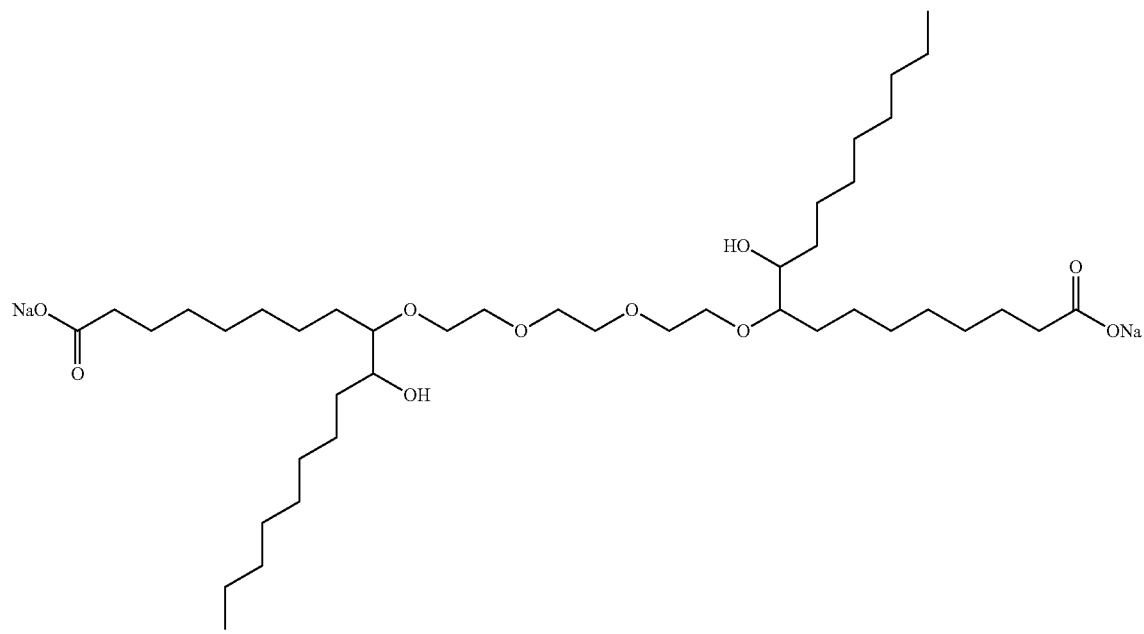

Candidate 20

The presence of sulfonates significantly improves the ability to remove grass stains. Our previous sulfonates were based on the reaction of MeEHOSO with amino-aromatic sulfonates. These sulfonates did not perform well when compared to sodium dodecylbenzene sulfonate (SDBS) or sodium lauryl sulfonate (SLS). This was likely due to the higher pKa of the amino-aromatic sulfonates when compared to sulfonates attached to an aliphatic chain. For this reason, new sulfonates were developed. The first candidate was based on the direct reaction of chlorosulfonic acid with MeEHOSO followed by salt formation. The product can be seen below.

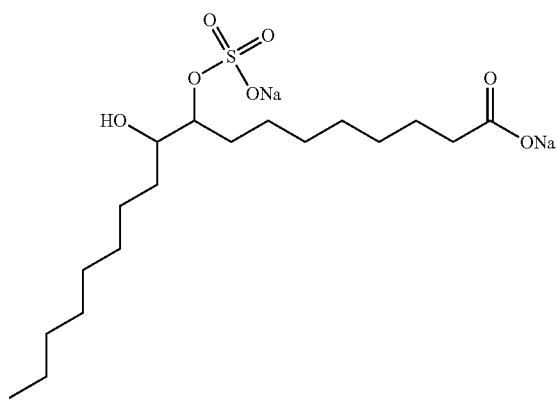

Candidate 15

Another sulfonate candidate was produced by first hydroformylation of high oleic soybean oil methyl ester followed by hydrogenation to form a mono-hydroxymethyl group at the original double bond. This hydroxyl was then sulfonated followed by salt formation. The structure can be seen below.

Candidate 17

The best performing candidate was produced by first reacting the MeEHOSO with diethylene glycol to form an ether and then sulfonating the remaining hydroxyl. The intermediate was the converted into the salt form. While diethylene glycol was chosen to minimize the percent weight, any polyethylene glycol could be used. The structure can be seen below.

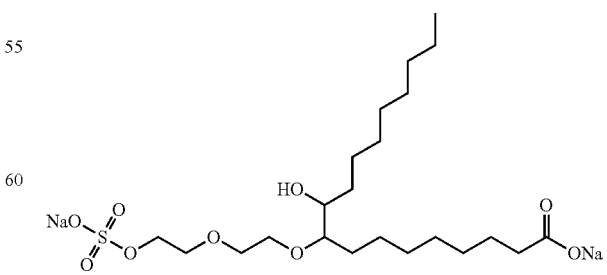

Candidate 16

Candidate 16's performance was tested against SLS and SDBS. The results can be seen in the table below.

| Soil | Substrate | Standard 120 mL | Candidate 16C 50% SDBS Replacement 120 mL | Candidate 16C 100% SDBS Replacement 120 mL | SIS Bio-Standard (normalized 120 mL | Sig. Dif. |
|---|---|---|---|---|---|---|
| Clay | Cotton | 58.8 | 53.8 | 58.6 | 60.8 | 6.9 |
| Coffee | Cotton | 51.2 | 51.5 | 44.8 | 42.2 | 8.6 |
| Dust Sebum | Cotton | 56.3 | 44.1 | 40.4 | 44.7 | 5.6 |
| EMPA 101 (Olive Oil) | Cotton | 8.4 | 8.6 | 8.4 | 8.9 | 2.4 |
| EMPA 112 (Cocoa) | Cotton | 7.1 | 4.4 | 11.1 | 9.3 | 5.9 |
| EMPA 116 (Blood, Milk, Ink.) | Cotton | 22.1 | 18.8 | 18.4 | 32.4 | 2.2 |
| Grass | Cotton | 59.1 | 72.8 | 48.3 | 33.9 | 6.2 |
| Make up | Cotton | 34.9 | 25.4 | 18.1 | 20.8 | 7.8 |
| Red wine | Cotton | 34.9 | 38.7 | 36.1 | 46.1 | 5.6 |
| Spaghetti | Cotton | 75.6 | 72. | 74.5 | 85.2 | 7.8 |
| Overall Soil Removal Totals | | 418.4 | 390.1 | 358.7 | 384.2 | 59.0 |
| % of Best | | Best | 93% | 86% | 92% | |

The standard formulation contained SDBS as the anionic surfactant. A difference in stain removal of 10% or less is considered equivalent performance. As can be seen, equivalent performance to the standard was observed when replacing 50% of SDBS with Candidate 16 called 16C in the Table). More importantly, an improvement in grass stain removal was observed. However, this advantage was lost when replacing 100% of SDBS. Both levels of substitution were equivalent in the same formulation where SLS was used as the anionic surfactant.

We next produced Candidate 43 at 30-gallon scale and tested some candidates versus our standard formulations and three off-the-shelf fully additized standards. Results are shown below.

that there were no differences when scaling betaine Candidate 43 (ethyl cellosolve ring opened) from bench to 30-gallon scale. More interesting was the result in Candidate 48 being equivalent. Candidate 48 is the commodity soybean oil version of Candidate 43. The reason that this was interesting was due to testing performed earlier. We had found that Candidate 25 (diethylene glycol ring opened) had performed equivalent to cocamidopropylbetaine in our formulations (Standard 2). However, the equivalent commodity soybean oil Candidate 32 performed at 95% of the standard; 5 percent deficient. The change from diethylene glycol to ethyl cellosolve improved the performance of the commodity soybean oil candidate.

| Soils on Cotton | Off-Shelf Std 1 | Off-Shelf 7th Std 2 | Off-Shelf Std 3 | Standard 1 | Standard 2 | Soy Mix 1 | Candidate 43 (30-Gal Scale) | Candidate 48 | Sig Dif. |
|---|---|---|---|---|---|---|---|---|---|
| Clay | 63.8 | 60.0 | 53.7 | 61.6 | 68 | 57.6 | 71.8 | 69.0 | 3.2 |
| Coffee | 54.7 | 51.4 | 46.0 | 52.8 | 48.3 | 64.1 | 48.1 | 49.5 | 3.9 |
| Dust Sebum | 63.9 | 60.1 | 53.8 | 61.7 | 59.4 | 60.6 | 69.2 | 65.5 | 5.3 |
| EMPA 101 (Olive Oil) | 8.7 | 8.2 | 7.3 | 8.4 | 9.7 | 9.9 | 8.7 | 7.8 | 0.9 |
| EMPA 112 (Cocoa) | 2.6 | 2.4 | 2.2 | 2.5 | 3.8 | 11 | 5.1 | 6.0 | 3.2 |
| EMPA 116 (Blood, Milk, Ink.) | 8.8 | 8.3 | 7.4 | 8.5 | 7.7 | 15.6 | 10.4 | 10.6 | 0.9 |
| Grass | 55.8 | 52.5 | 47.0 | 53.9 | 47.2 | 45.4 | 59.9 | 53.6 | 4 |
| Make up | 59.6 | 56.0 | 50.1 | 57.5 | 71.3 | 54.4 | 61.1 | 55.2 | 9.8 |
| Red wine | 30.8 | 28.9 | 25.9 | 29.7 | 26.9 | 39.1 | 27.5 | 25.5 | 2.4 |
| Spaghetti | 86.0 | 80.9 | 72.3 | 83 | 82.9 | 84.7 | 80.6 | 78.7 | 2 |
| Overall Soil Removal Totals | 434.7 | 408.8 | 365.7 | 419.6 | 425.2 | 442.4 | 442.4 | 421.4 | |
| % of Best | 102% | 96% | 86% | 99% | 100% | 104% | 104% | 99% | |

As seen in the tables, our lab produced standards, from which we swapped out surfactants, perform equivalent or better than the off-the-shelf standards. As mentioned before, ±10% is considered equivalent in the stain testing. We found The table above also includes SoyMix 1 which was a mixture of multiple soy candidates. No other surfactants were used in the formulation leading to a fully soybean-based formula. In that formula, we used an improved chelating surfactant.

Candidate 50

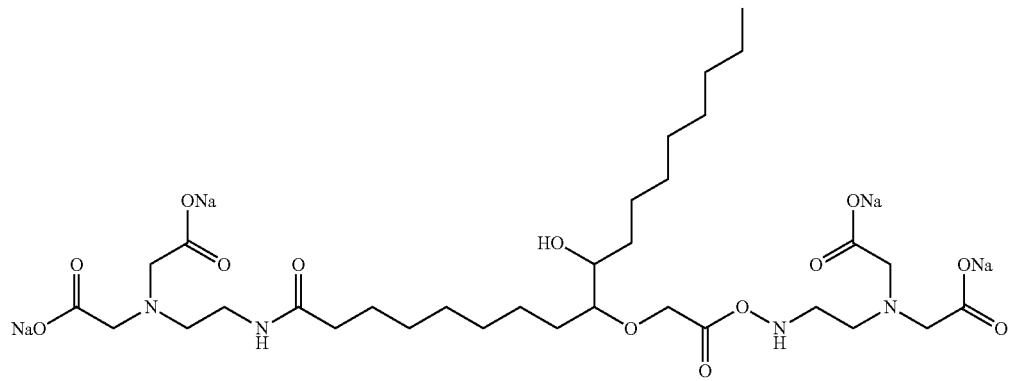

Candidate 50 builds off the earlier work where epoxidized HOSO was ring opened with ethyl glycolate. The intermediate was amidified with ethylenediamine followed by the reaction with chloroacetic acid in aqueous sodium hydroxide. The resulting candidate 50 chelates similarly to EDTA (ethylenediamine tetraacetic acid) while also acting as a surfactant. This was validated by tradition water hardness titration testing. A similar candidate was produced from ethyl lactate (Candidate 2 intermediate) and can be seen below.

Figure 2:
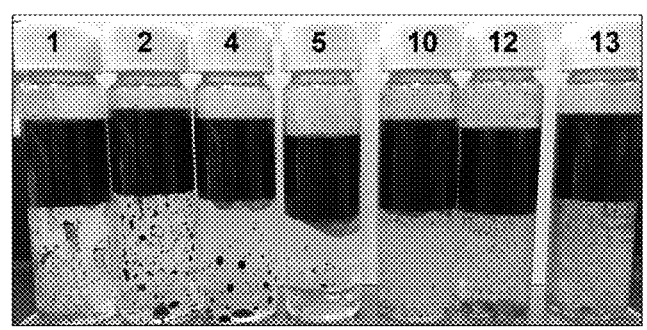
FIG. 2 shows the oil/aqueous phase separations for selected surfactants.

Another application area is in oil and gas. We chose to test multiple candidates at 1% concentration in water to evaluate oil separation from water (as seen in FIG. 2).

Figure 3:
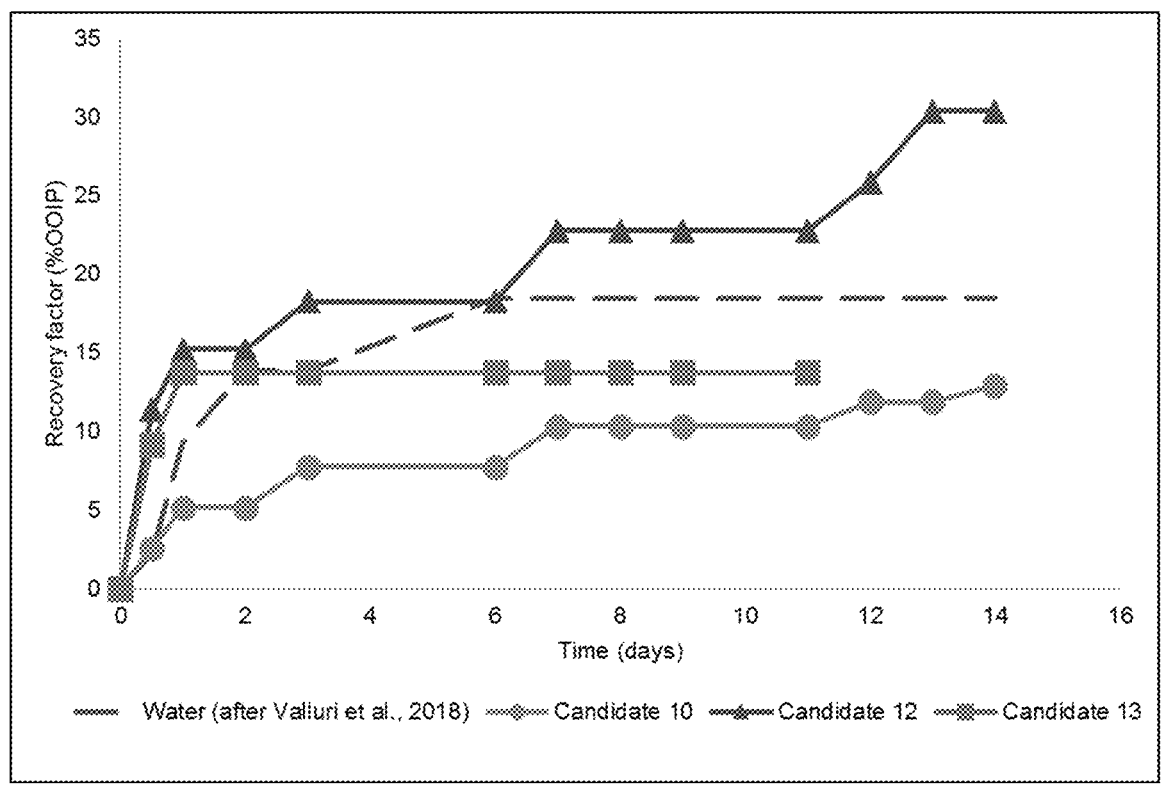
FIG. 3 shows recovery factors for selected surfactants.

It was noted that candidates 10 and 12 were the best performers. These candidates were in our earlier patent application and contained the reaction products of EHOSO with either ethylenediamine (Candidate 12) or diethylenetriamine (Candidate 10). The candidates were then tested in spontaneous imbibition testing. The results are shown in FIG. 3.

Candidate 46

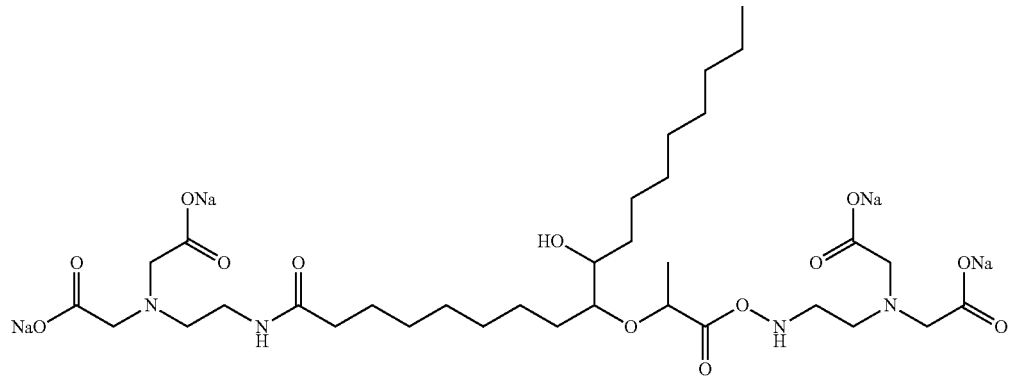

Candidate 32

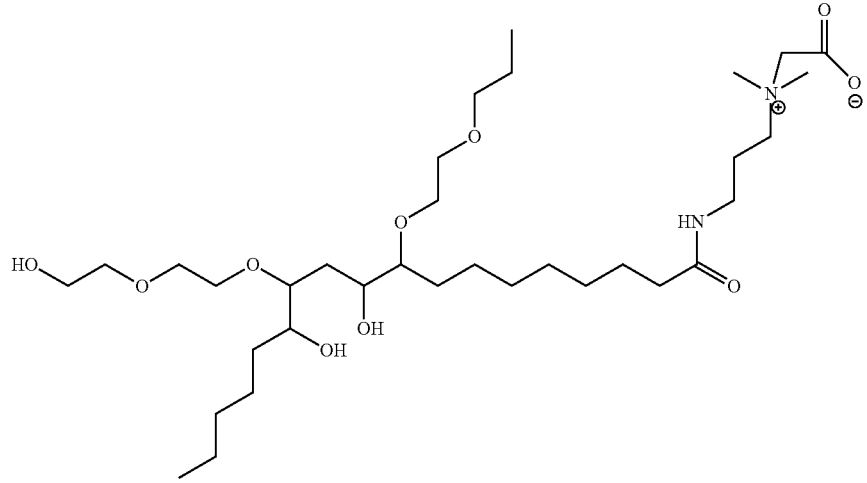

Candidate 12 was the best performer for oil extraction and correlated to an improvement in oil recovery of 72%. Two more candidates were produced to target enhanced oil recovery. The first candidate was produced from the amidification of hydroforymylated/hydrogenated HOSO methyl ester with diethylenetriamine (ethylenediamine could also have been produced). The structure can be seen below.

Candidate 18

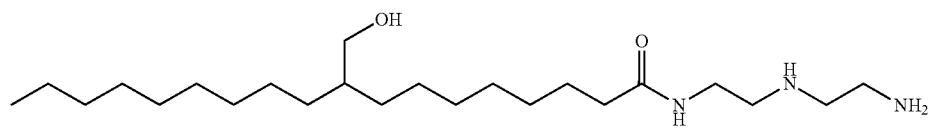

The second structure was produced by the amidification with diethylene triamine of the reaction product of ring opened EHOSO with methanol. Again, ethylenediamine could have been used. The structure can be seen below.

Candidate 19

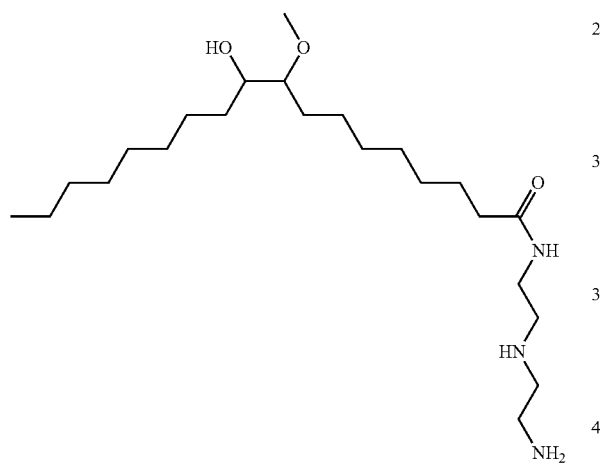

These structures could be quaternized in order to create an antimicrobial surfactant having reduced toxicity from the amine structures. Another option is to change properties by forming amides at the nitrogen sites. This would change the overall polarity of the structure. Although various levels of amides could be used, an idealized structure of four new amides can be seen below.

ring opened ethanolamide). As mentioned above, the amide structure is essential in improving enhanced oil recovery performance.

Another application where surfactants are used is agricultural adjuvants. Adjuvants are used to deliver herbicides and pesticides or can be used as drift reducing agents (DRA). On top of the wide array of our candidates could be used for this application, the ester intermediates could be applicable also. This is due to the need of the adjuvant to penetrate the waxy layer of plants. As a representation, one candidate intermediate can be seen below. However, the intermediate for any of our candidates will contain esters in place of sodium salts.

Candidate 4 Intermediate

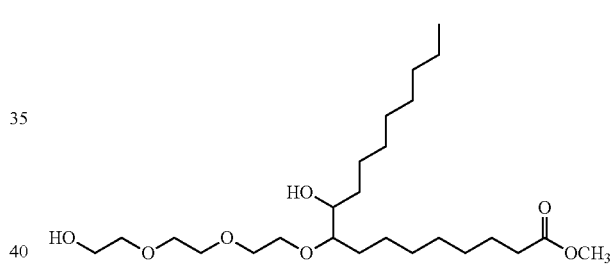

Another candidate that is commonly used as a drift reducing agent is an alkyl glucoside. One such structure was produced for evaluation as a DRA. Utilizing the intermediate Candidate 5 (similar to candidate 4 intermediate but with a PEG 200 group instead of triethylene glycol), we produced Candidate 21

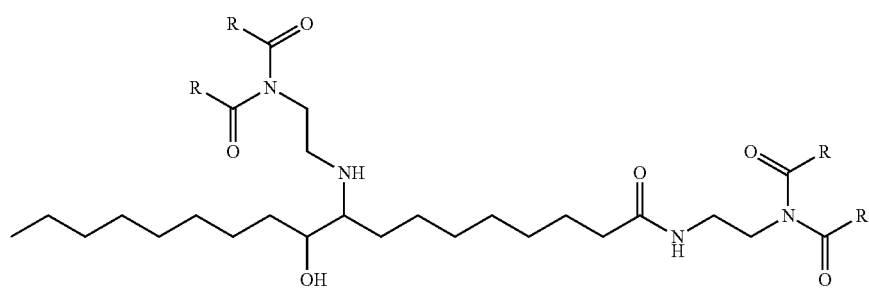

One other candidate that performed well in the water separation was mentioned earlier as Candidate 49 (methanol

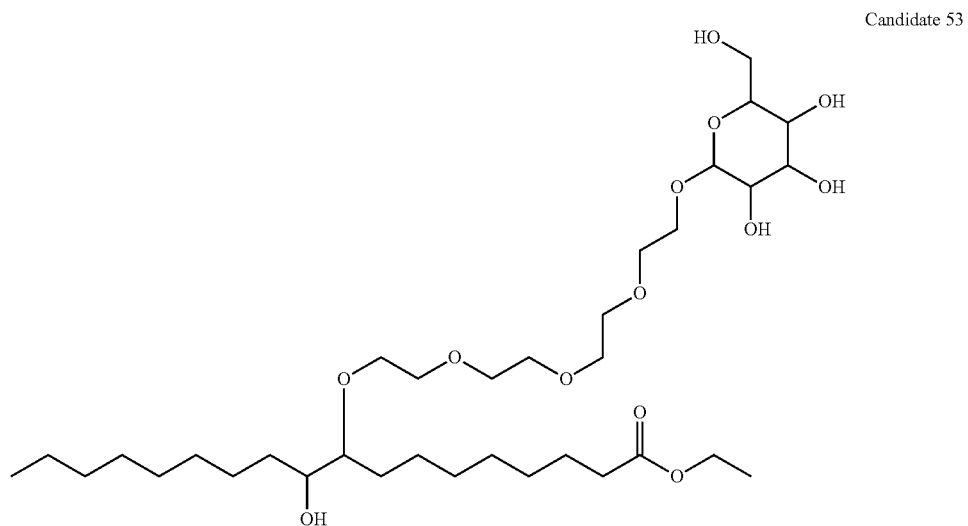 [SMILES: CCCCCCCCC(O)C(CCCCCCCC(=O)OCC)OCCOCCOCCOCCOC1OC(CO)C(O)C(O)C1O]
Candidate 53
We also produced a similar candidate from the diethanolamide of the intermediate for Candidate 5. The idealized structure can be seen below.
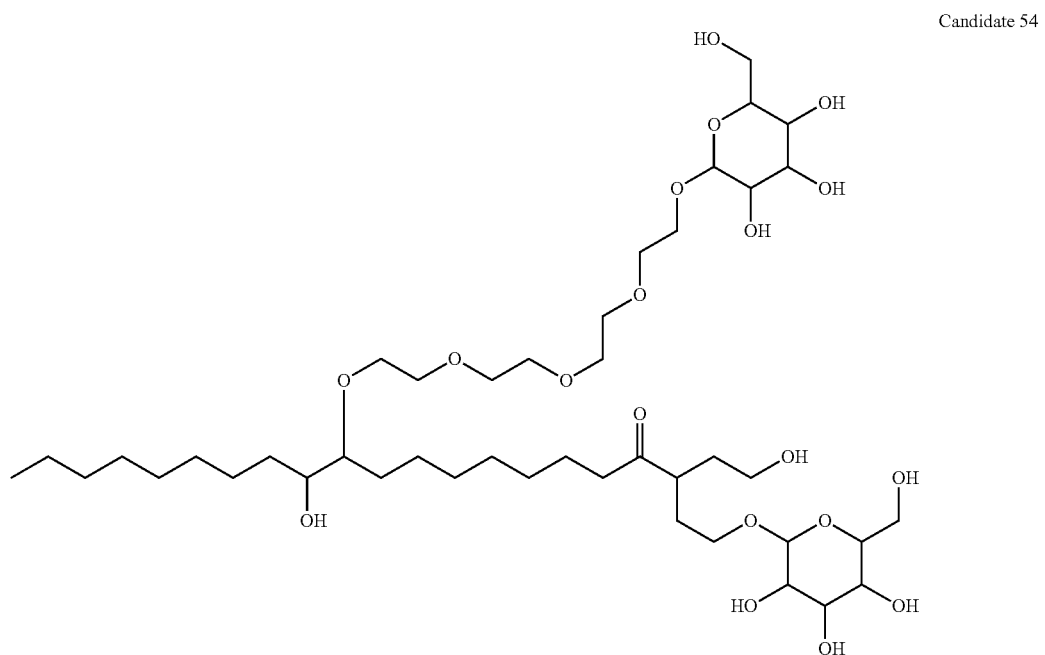 [SMILES: CCCCCCCCC(O)C(CCCCCCCC(=O)C(CCO)CCOC1OC(CO)C(O)C(O)C1O)OCCOCCOCCOCCOC1OC(CO)C(O)C(O)C1O]
Candidate 54
Other candidate structures produced but not mentioned above can be found here:

Candidate 31
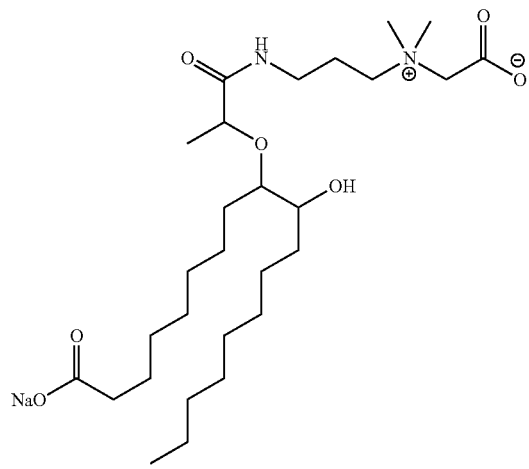
Candidate 33
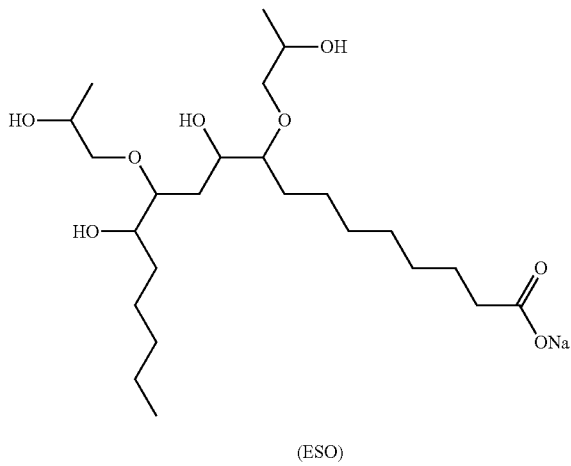
(ESO)
Candidate 34
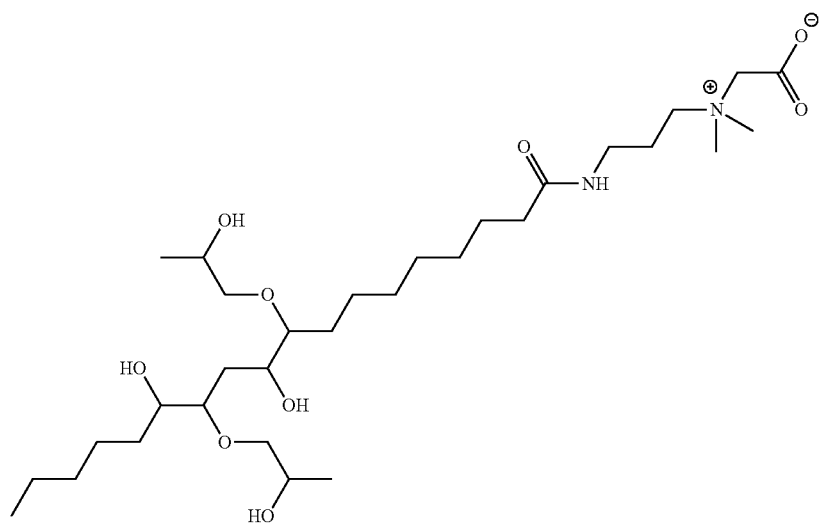
Candidate 35
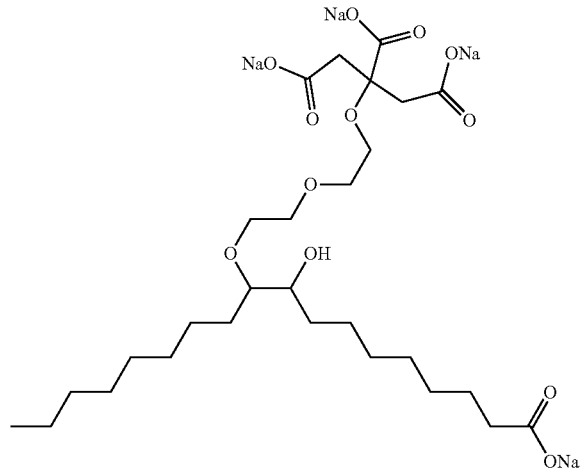
(produced from dialkoxylated triethyl citrate)

Candidate 36
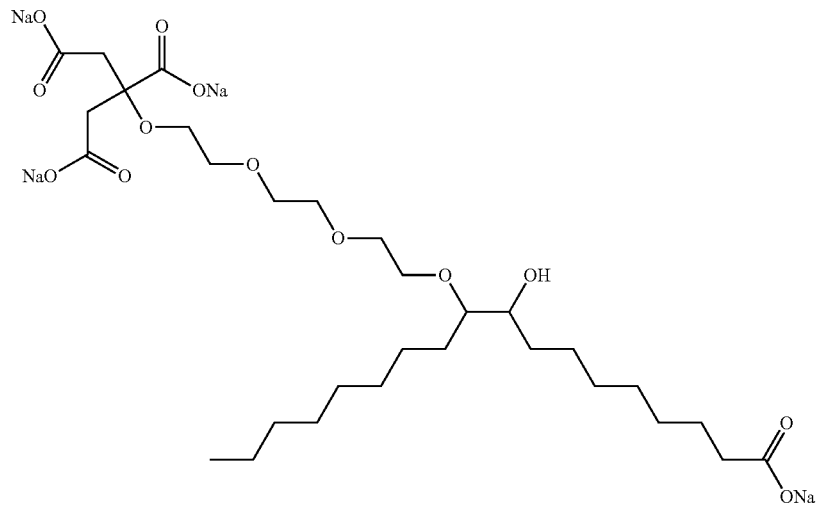
(produced from trialkoxylated triethyl citrate)
Candidate 37
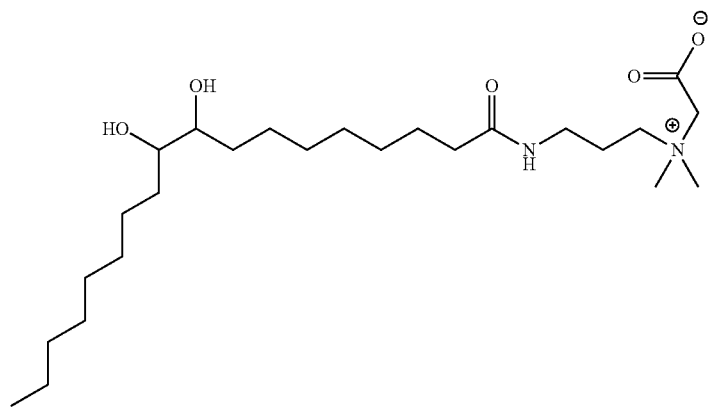
Candidate 38
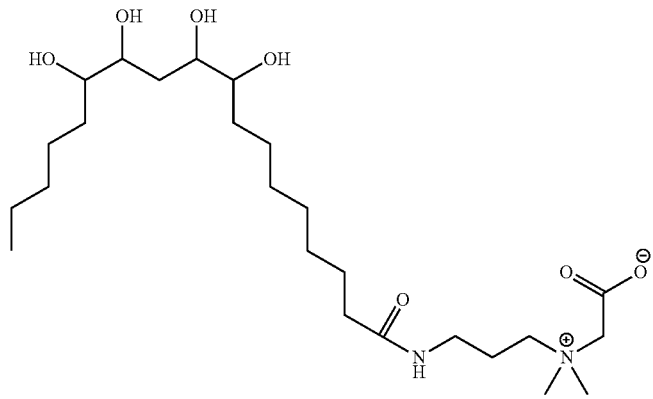
(ESO)

Candidate 39
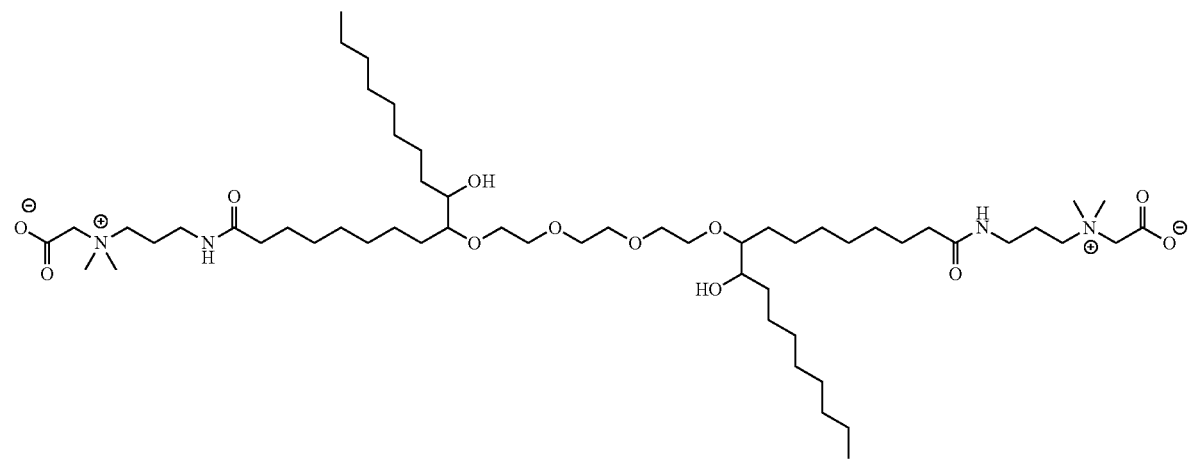
Candidate 40
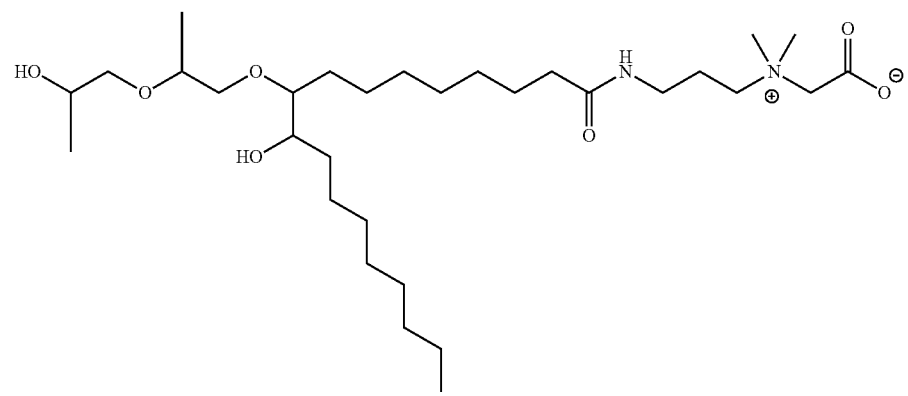
Candidate 41
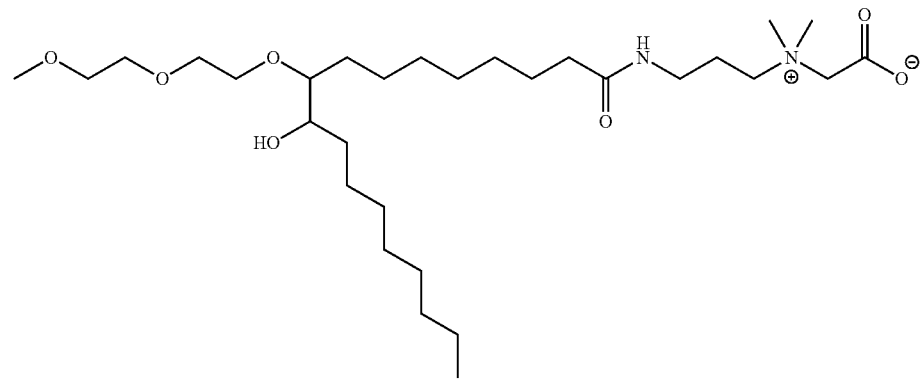
Candidate 42
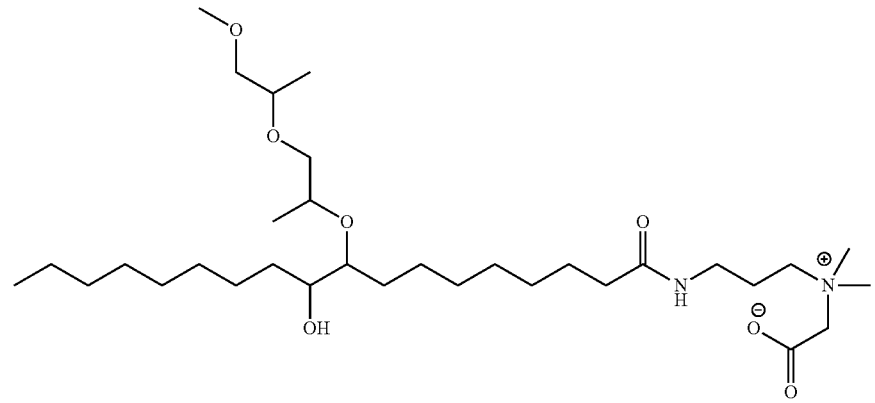

-continued
Candidate 44
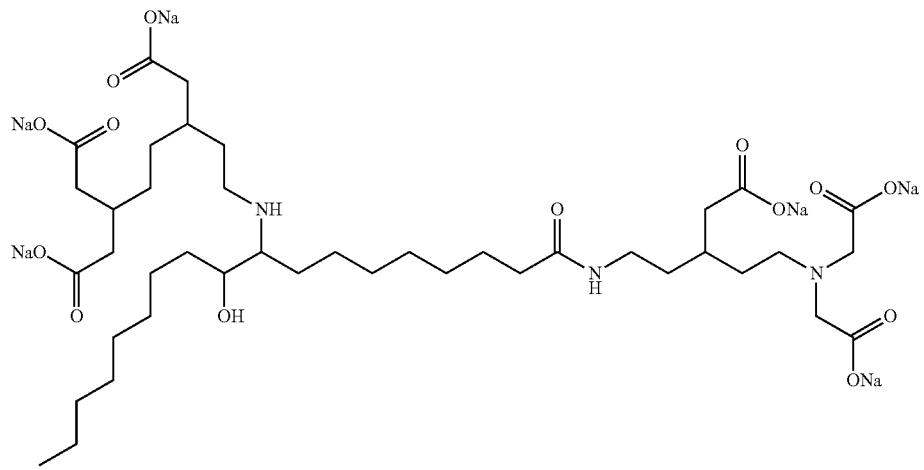
Candidate 45
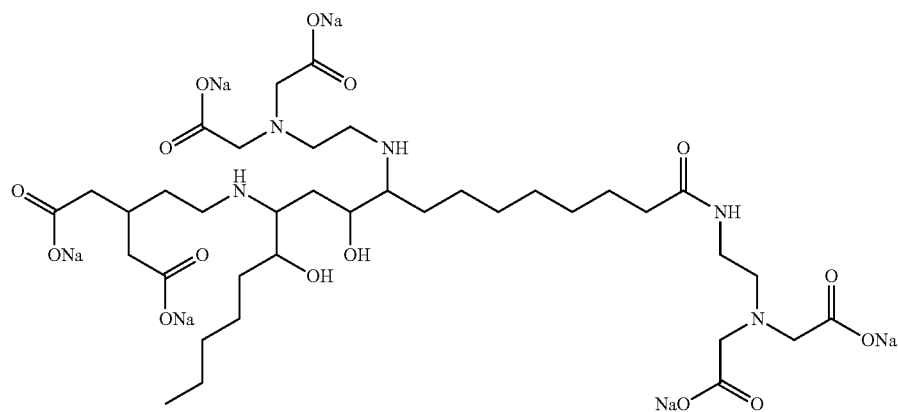
Candidate 47
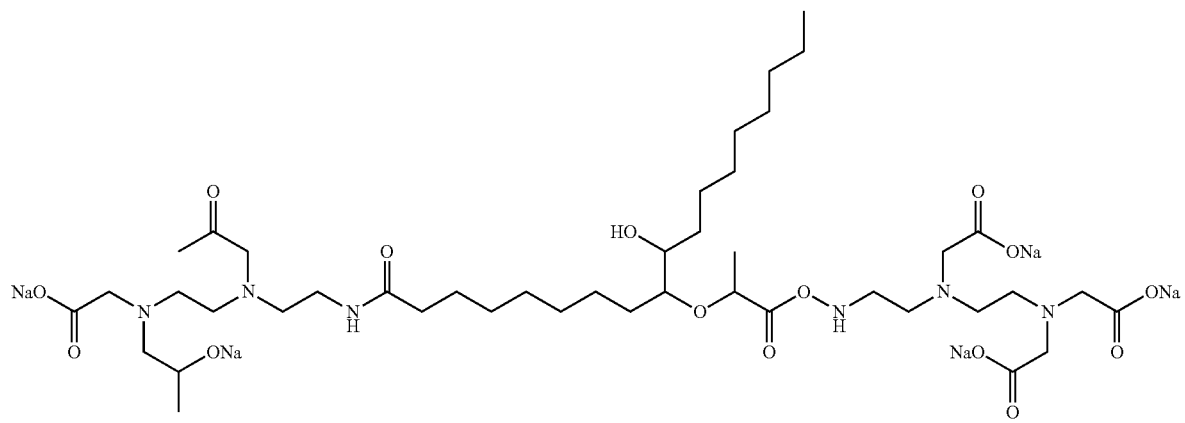
Candidate 51
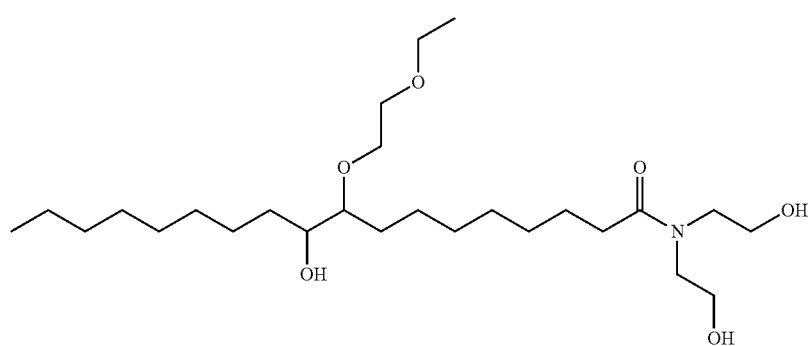

Candidate 52

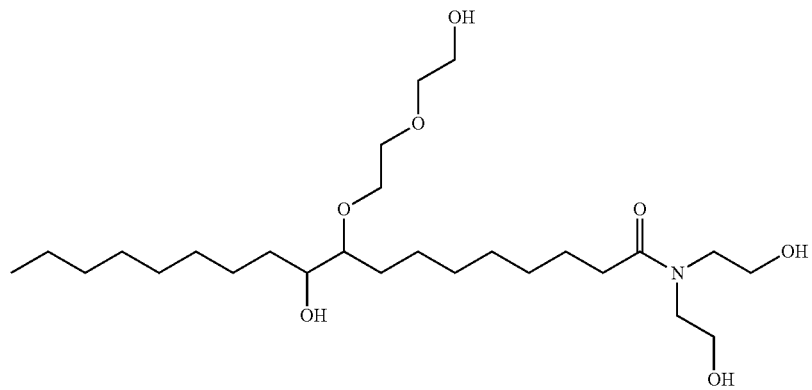

General procedures can be found below.

Example 1

Transesterification of Epoxidized High Oleic Soybean Oil 2 kilograms of epoxidized plenish were mixed with 600 mL Methanol and heated to 50 C for 6 hours. Excess methanol was removed by vacuum and the pot was passed through a short column of alumina to remove the catalyst. The resulting product was labeled epoxidized methyl plenish.

Example 2

Epoxy Ring-Opening with a Hydroxyl or Water 1 kilogram of epoxidized plenish was added to 632.34 grams of diethylene glycol and heated to 60 C. 8.41 grams of copper (II) tetrafluoroborate were dissolved 50 grams of diethylene glycol and added to the mixture. The reaction was then heated to 90 C for 4 hours. Catalyst was removed by passing through a small amount of basic alumina. The excess diethylene glycol was removed by vacuum distillation (245 C at 1 atm) to produce Candidate 25 Intermediate 1.

Example 3

Epoxy Ring-Opening with an Amine 49.93 grams of epoxidized high oleic soybean oil was added to 66.33 grams of diethylenetriamine in an autoclave. The mixture was heated to 180 C for 12 hours. The amidification was verified by IR. The water-soluble product was verified by $^1$H NMR.

Example 4

Saponification of the Carboxylic Acid Ester 274.13 grams of sodium hydroxide were dissolved into 1284.79 grams of distilled water and heated to 90 C. 1 kilogram of Candidate 1 Intermediate was slowly added to the mixture. After addition, the mixture was raised to 96 C and held for 6 hours.

Example 5

Amidification of the Carboxylic Acid Ester 1 kilogram of Candidate 25 Intermediate 1 was added to 219 grams of 3-(dimethylamino)-1-propylamine and heated to 130 C for 6 hours. Amidification was followed by IR. The excess amine was removed by vacuum distillation (133 C at 1 atm) to produce Candidate 25 Intermediate 2.

Example 6

Propoxylation of an Alkyl Hydroxy Ester 65 grams of ethyl-L-lactate were charged into an autoclave with 1 mL boron trifluoride diethyl etherate. The autoclave was held at ambient temperature. 67.45 grams of propylene oxide (PO) was charged to a ballast tank and placed under 100 psi pressure. The PO was then charged to the autoclave under pressure resulting in an exotherm from ~18 C to 60 C. The mixture was then heated to 130 C for 8 hours. The reaction was analyzed by $^1$H NMR and revealed ~1.1 moles of PO had reacted to the lactate hydroxyl. Excess PO was removed by vacuum.

Example 7

Sulfonation of a Hydroxyl 444.7 grams of Candidate 4 intermediate (triethylene glycol ring-opened epoxidized HOSO) were dissolved into 740 mL of chloroform and placed into reactor with magnetic stirring. 115.23 grams of chlorosulfonic acid were then added to the reactor dropwise over 45 minutes. The exhaust gas was trapped in a base bath to capture hydrochloric acid as it was created. The reactor temperature was then held at 50 C for 2 hours. Solvent was then removed by vacuum.

Example 8

Hydroformylation and Hydrogenation of High Oleic Soybean Oil 200.66 grams of epoxidized HOSO methyl ester, 1.64 grams of rhodium on alumina, and 2.10 grams of triphenylphosphine were charge to an autoclave. The reactor was purged 3 times with nitrogen and 5 times with syn gas (50% carbon monoxide with hydrogen balance). The reactor was then heated to 120 C and pressurized to 1050 psi with syngas. Pressure and temperature were held for 8 hours. The rhodium catalyst was removed by filtration resulting in a dark brown liquid. The resulting product was verified by $^1$H NMR. The mixture was then charged back to the autoclave and 12.36 grams of ruthenium on carbon and 8.25 grams of ruthenium on titanium oxide were added to the autoclave. After purging, the autoclave was pressurized to 750 psi hydrogen and heated to 100 C and run for 10 hours. 98% of the aldehyde was converted to hydroxyl as verified by $^1$H NMR. The catalyst was removed by filtration.

Example 9

N-Oxide Formation 50 grams of 2-(dimethylamino)-ethanol ring opened epoxidized HOSO were charged to a reactor with mechanical stirring. 10.23 grams of 50% hydrogen peroxide were added dropwise with stirring resulting in an exotherm with a max temperature of 48.2 C.

Example 10

Chloroacetic Acid Reaction to Form Chelator 76.76 grams of propoxylated ethyl lactate ring opened epoxidized methyl HOSO that was amidified with ethylenediamine was weighed into a flask containing 49.31 grams of sodium hydroxide and 180.70 grams of water. Using magnetic stirring, 56.75 grams of chloroacetic acid were then added slowly to maintain a temperature below boiling. After addition was complete, the temperature was held at 95 C for 4 hours. Chelation capacity was verified by hard water titration.

Example 11

Chloroacetic Acid Reaction to Form Zwitterion 81.84 grams of sodium hydroxide were dissolved into 1275.19 grams of distilled water. 1 kilogram of Candidate 25 Intermediate 1 were added and mixed followed by the slow addition of 193.35 grams of chloroacetic acid. The mixture was then heated to 90 C and held for 2 hours resulting in Candidate 25 formation.

Example 12

Hydroxysultaine Formation 99.20 grams of Candidate 43 Intermediate 2 [ethyl cellosolve ring opened HOSO epoxide amidified with 3-(dimethylamino)-1-propylamine] were weighed into a flask containing 161.73 grams of water. The mixture was stirred with magnetic stirring. 63.65 grams of 3-chloro-2-hydroxy-1-propanesulfonic acid sodium salt were then added slowly to the reaction mixture. The mixture was then heated to 90 C for 2 hours. The resulting surfactant (Candidate 55) was verified by $^1$H NMR.

Example 13

Butyl Glucoside Formation

To activate the acid catalyst, 7.5 g DOWEX 50W X8 was rinsed in a fritted funnel 5 times with distilled, deionized water, and 3 times with acetone. After letting dry, the DOWX 50W X8 sample was added to a flask containing 25.0 g (0.138 mol) glucose and 500 mL (5.46 mol) 1-butanol and heated for 4 h using a heating mantle while stirring. The solution was cooled down to room temperature and the excess 1-butanol was removed by vacuum at 110° C. at 200 μm Hg for 4 h. The synthesis of butyl glucoside was confirmed by $^1$H NMR.

Example 14

Ethyl Glucoside Formation 125.0 g (0.694 mol) glucose was added to a flask containing 500 mL (8.57 mol) ethanol. 1.50 mL conc. sulfuric acid was added dropwise to the flask while stirring. The flask was then heated to reflux (77° C.) using a heating mantle for 4 hours while stirring with a mechanical stir rod. The completion of the reaction was verified by NMR. The reaction was cooled to room temperature. 1.0 g calcium hydroxide was added to the solution to neutralize the H2SO4 and stirred. The calcium hydroxide was removed via vacuum filtration with a fritted funnel. The excess ethanol was removed via at 42° C. at 3 in Hg for 2 hours.

Example 15

Glucoside Formation of Epoxy HOSO Ring Opened with PEG 200 and Amidified with Diethanolamine 11.35 g (8.40 mmol) of PEG 200 DEA Soy Epoxy Plenish and 3.01 g (16.7 mmol) glucose were added to a flask and heated to 40° C. while stirring. 100 μL conc. sulfuric acid was added to the flask dropwise, which was subsequently heated to 70° C. After 1 h, the reaction was let cool to room temperature, and the identity of the product was verified via NMR.

Example 16

Synthesis of Glucose-Modified PEG 200 Soy Epoxy Plenish 25.01 g (0.138 mol) glucose and 59.34 g (41.9 mmol) PEG 200 Soy Epoxy Plenish were added to a flask containing 300 mL dimethylacetamide. While stirring with a mechanical stirrer, 0.5 mL H2SO4 was added to the flask, which was then heated to 80° C. To further drive the reaction, an additional 25.00 g glucose was dissolved, as well as 0.308 mL (2.50 mmol) BF3 diethyletherate. After letting react for 24 h, the resulting product was confirmed with NMR.

Prophetic Example 17

Synthesis of Glucose-Modified PEG 200 Soy Epoxy Plenish 50 g (0.260 mol) ethyl glucoside and 50 g (35.3 mmol) PEG 200 Soy Epoxy Plenish were added to a flask containing 300 mL dimethylacetamide. While heating to 70° C. under vacuum, 0.5 mL $H_2SO_4$ was added to the flask, which was then heated to 80° C. After letting react for 24 h, the resulting product was verified via NMR, and the dimethylacetamide was removed via vacuum distillation.

What is claimed:

1. A composition, comprising:

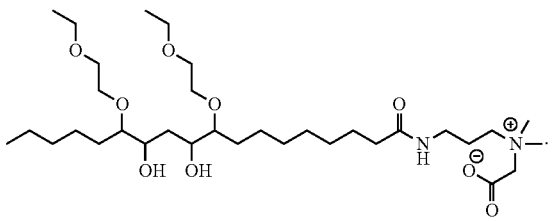

Candidate 48

2. The composition of claim 1 comprising at least 0.5 wt % of one or more compounds selected from:

Candidate 14
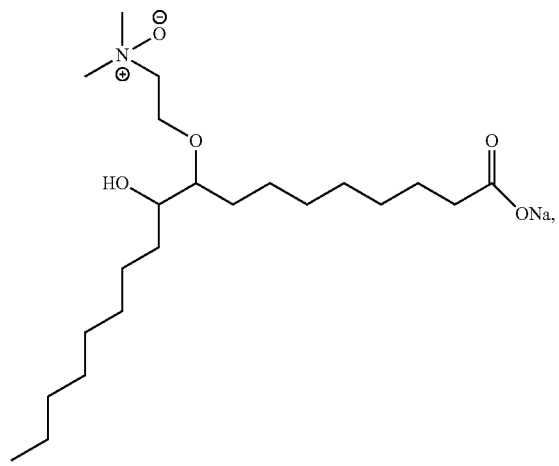
Candidate 15
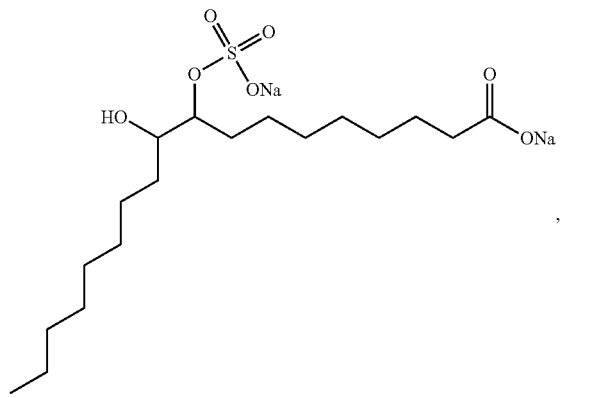
Candidate 16
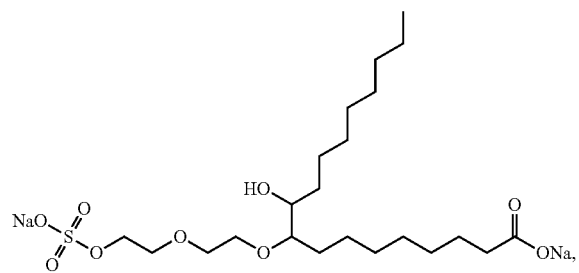
Candidate 17
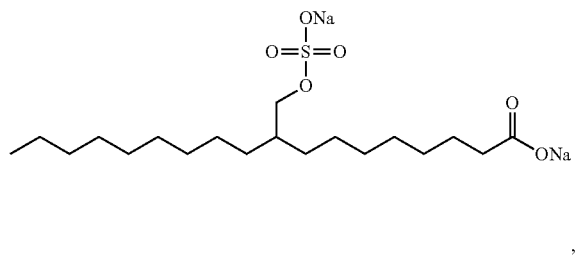
Candidate 18
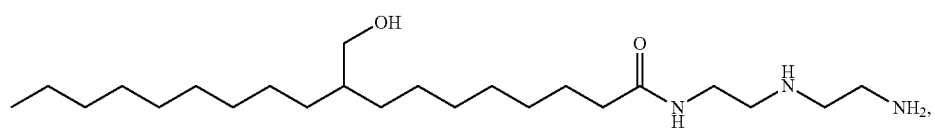
Candidate 19
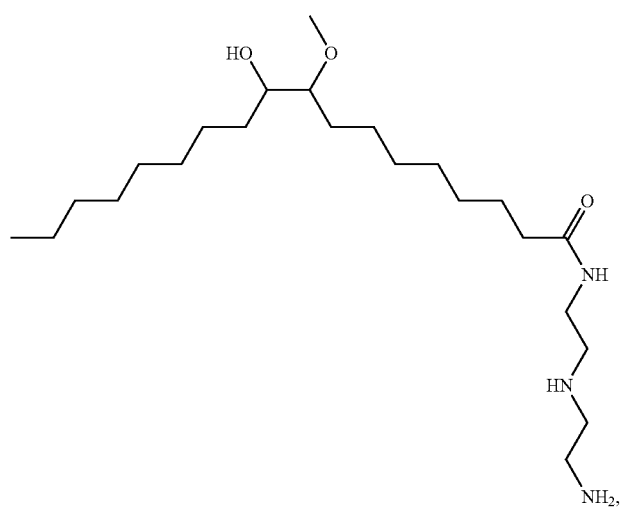

Candidate 20
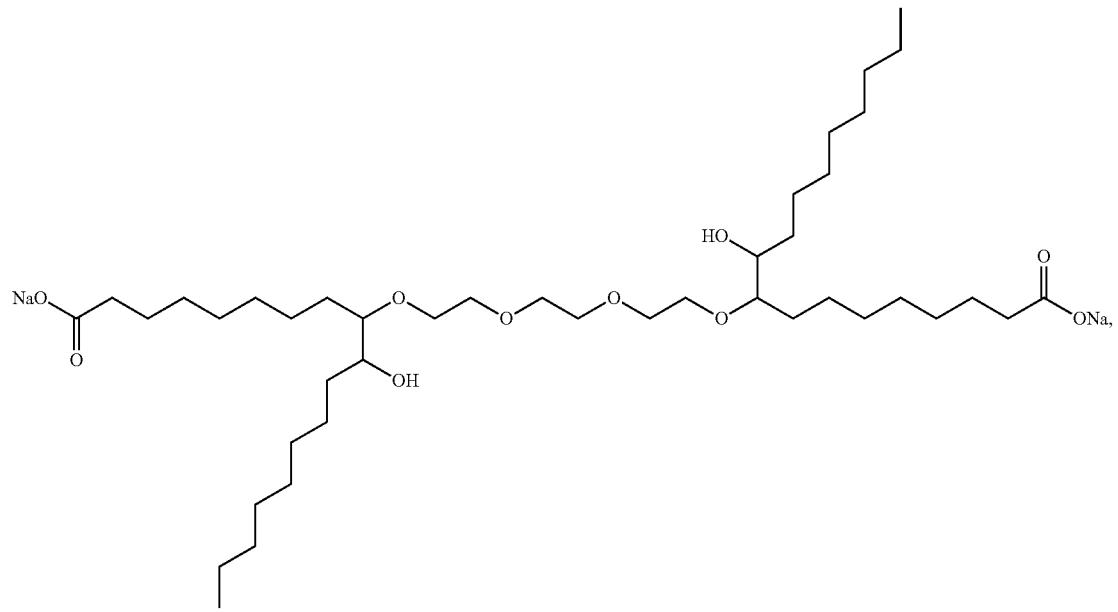
Candidate 21
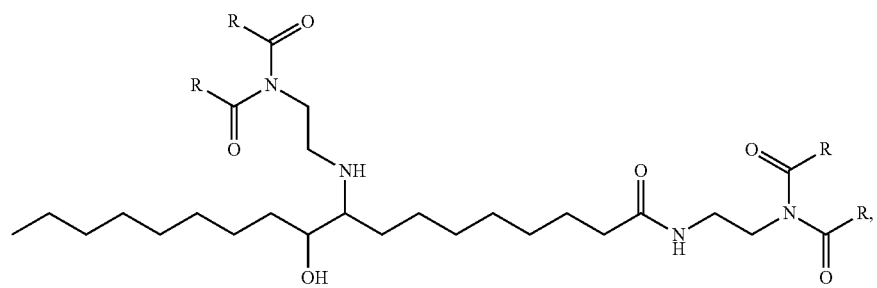
Candidate 22
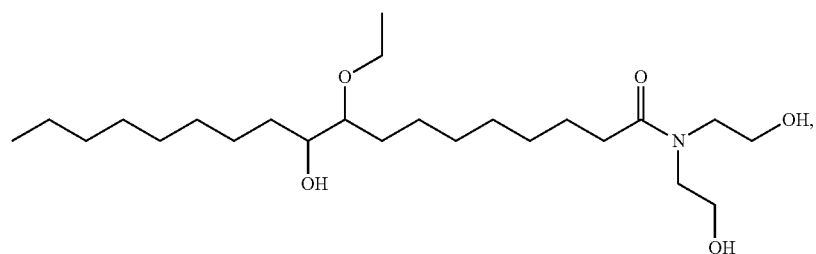
Candidate 23 Candidate 24
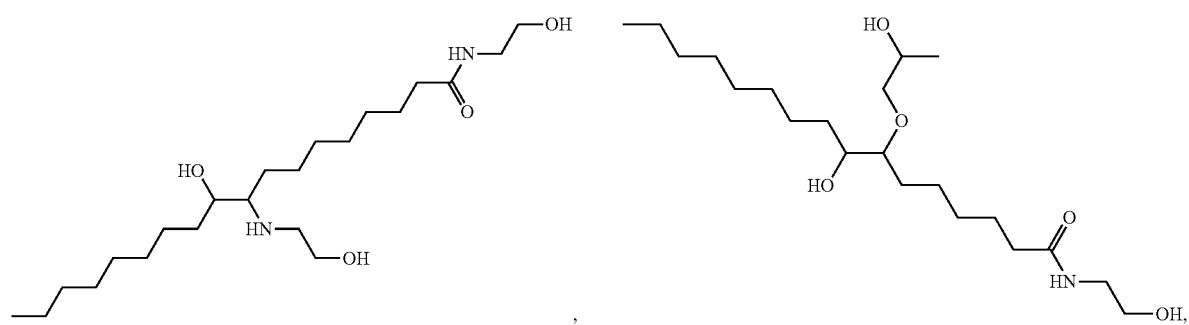

-continued
Candidate 25
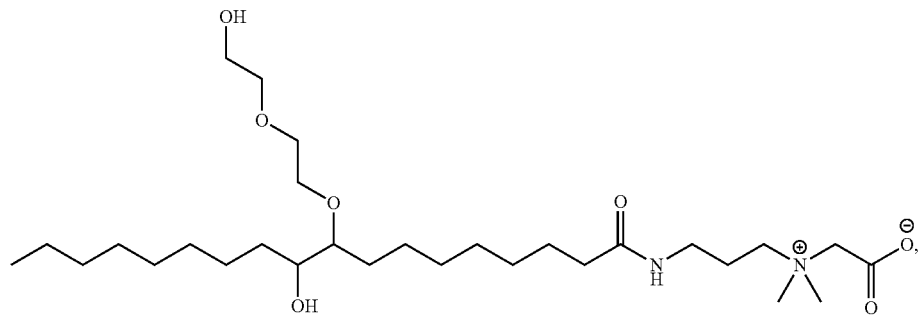
Candidate 26
Candidate 27
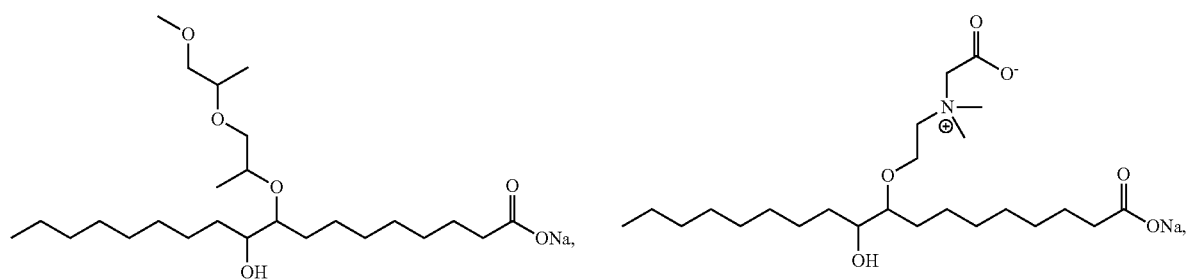
Candidate 28
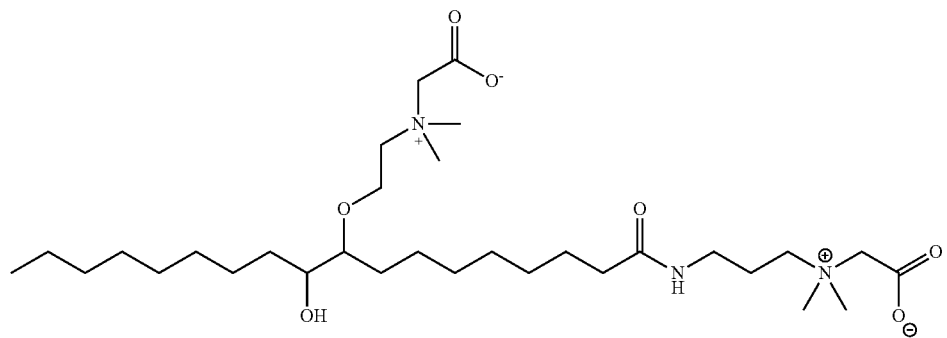
Candidate 29
Candidate 30
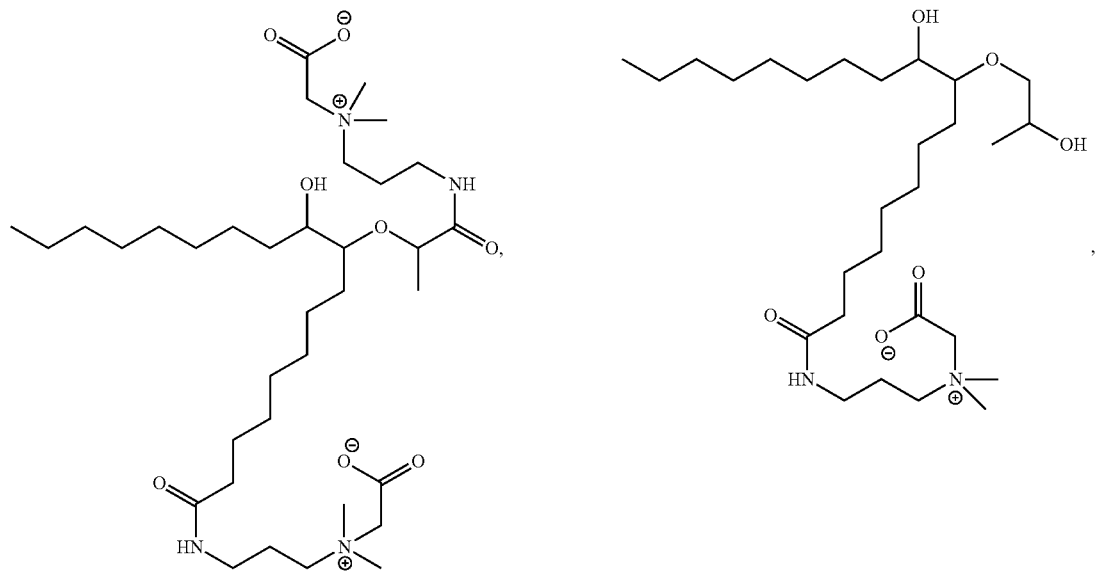

-continued
Candidate 31
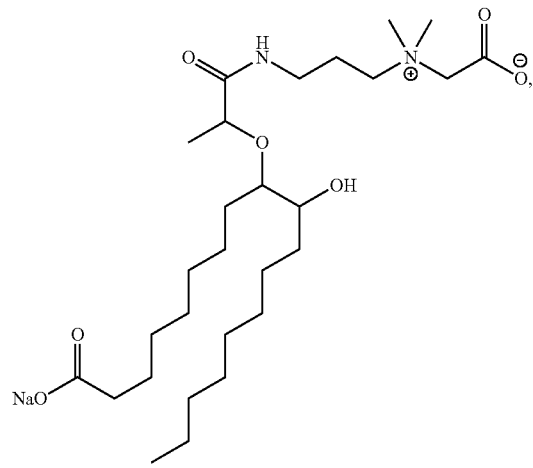
Candidate 32
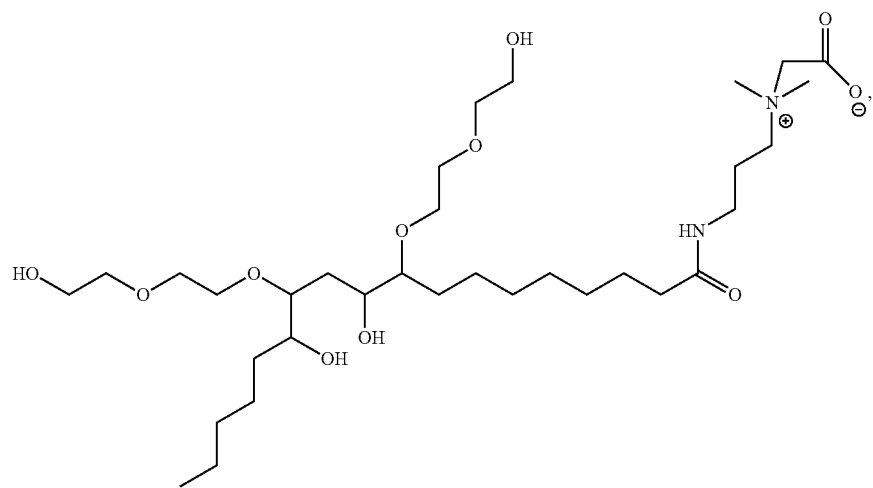
Candidate 34
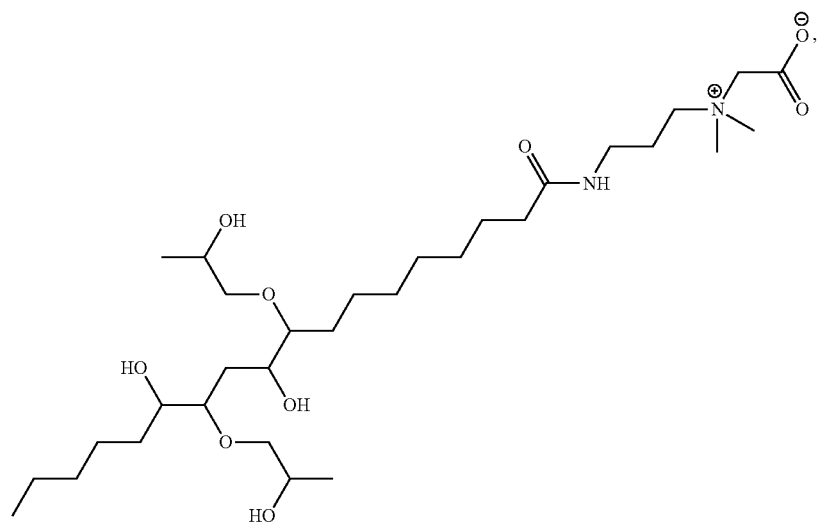

-continued
Candidate 35
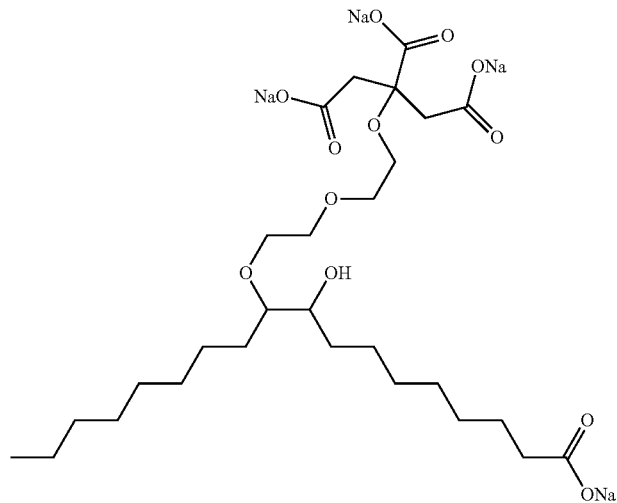
Candidate 36
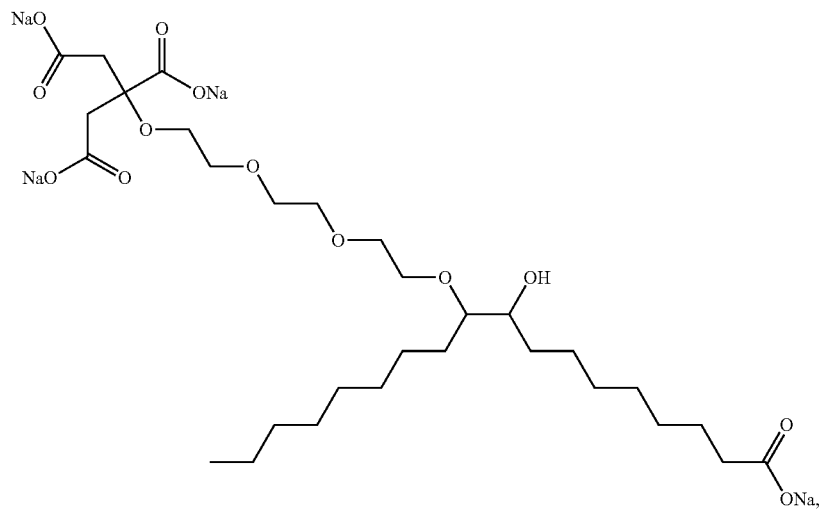
Candidate 37
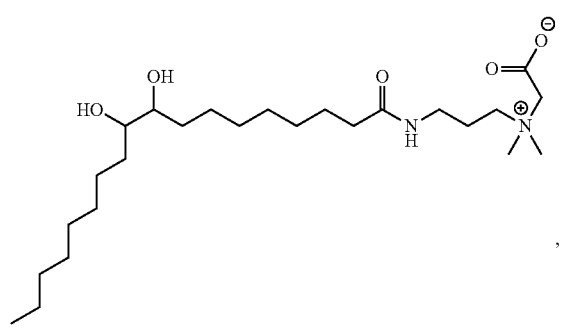
Candidate 38
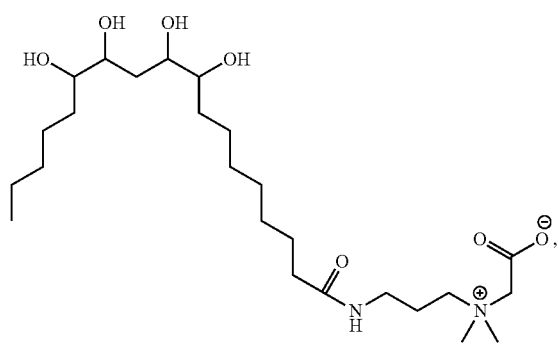

-continued
Candidate 39
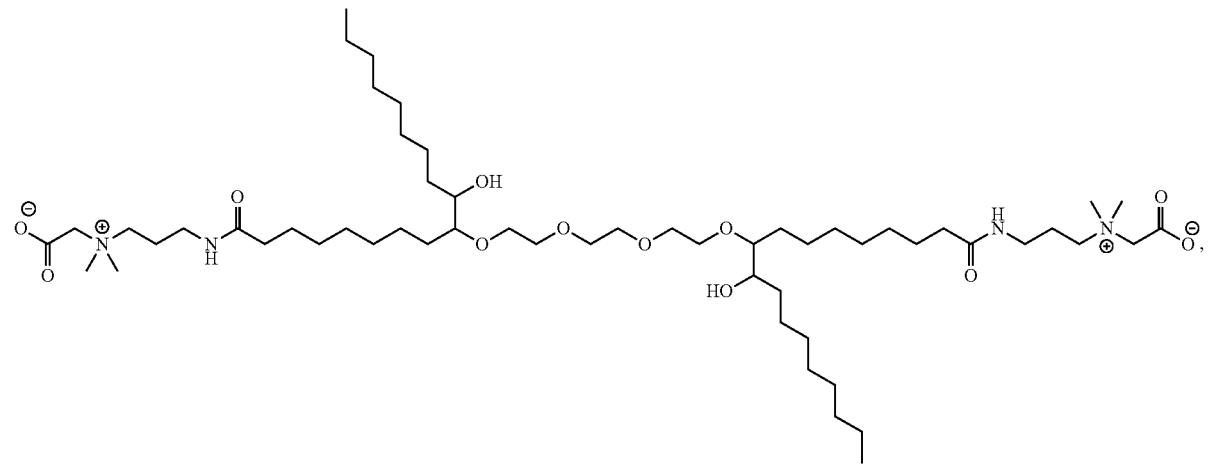
Candidate 40
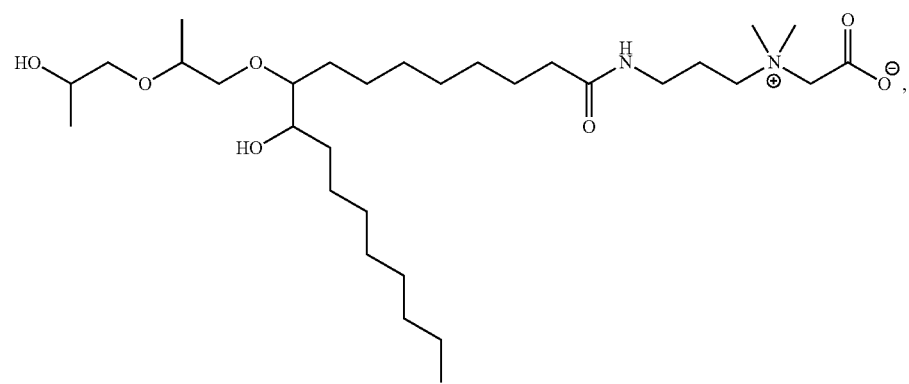
Candidate 41
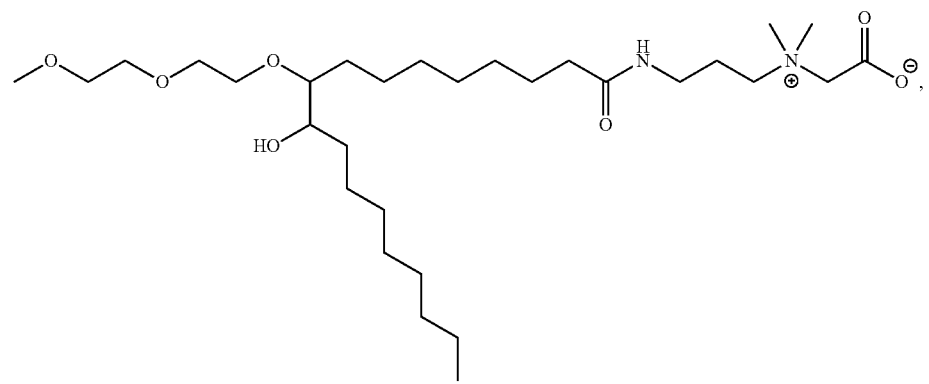

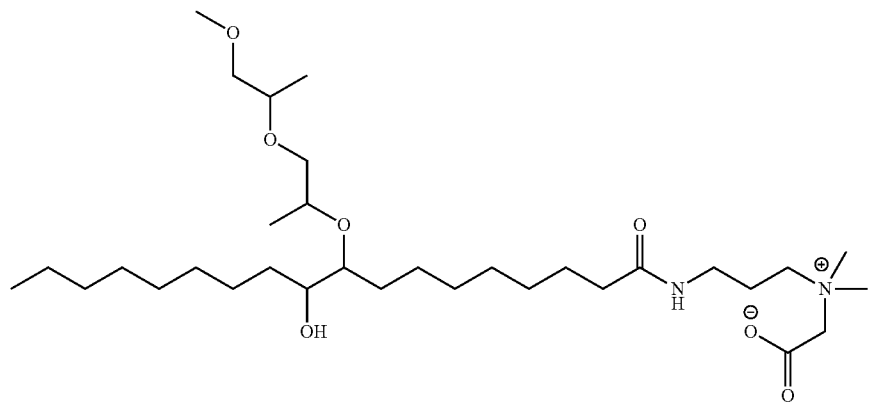
Candidate 42
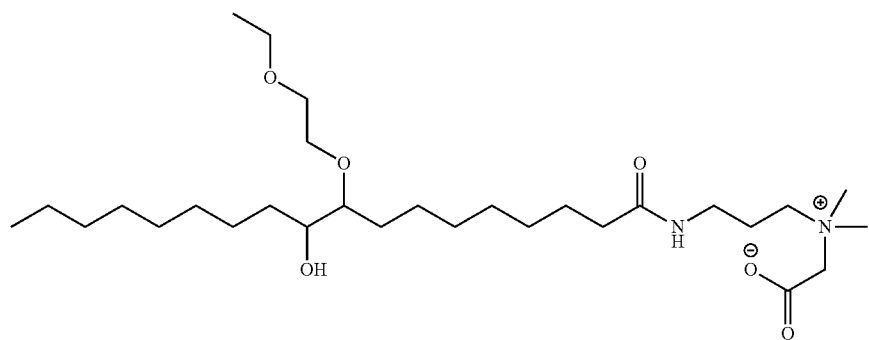
Candidate 43
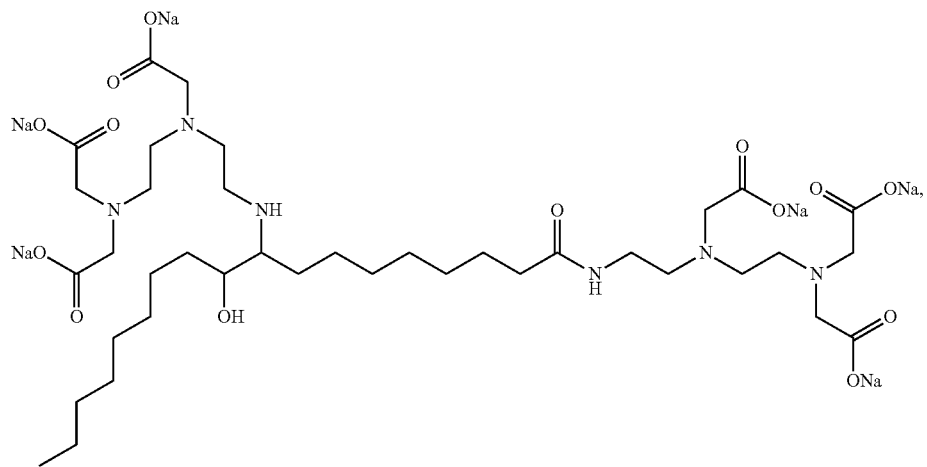
Candidate 44
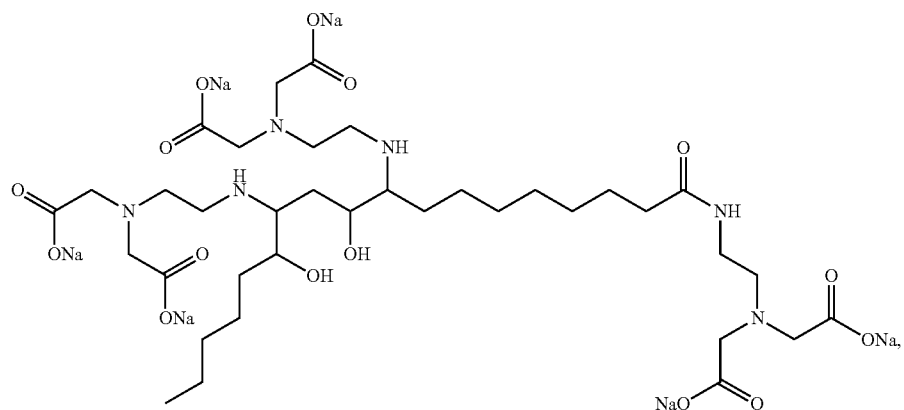
Candidate 45

Candidate 46
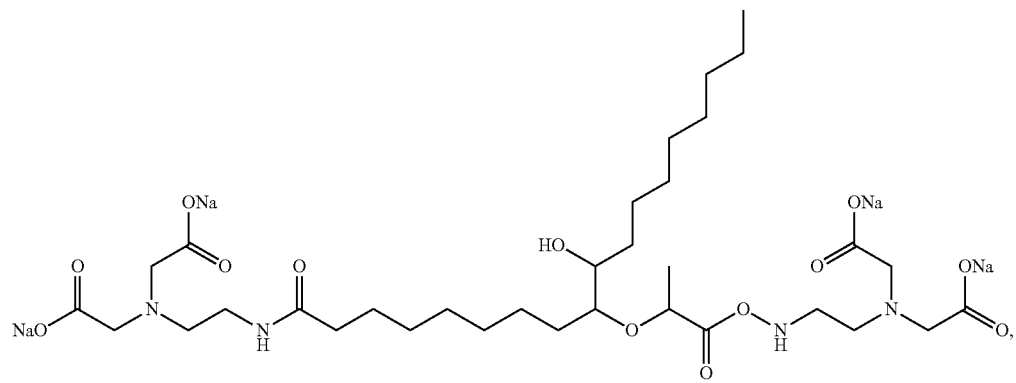
Candidate 47
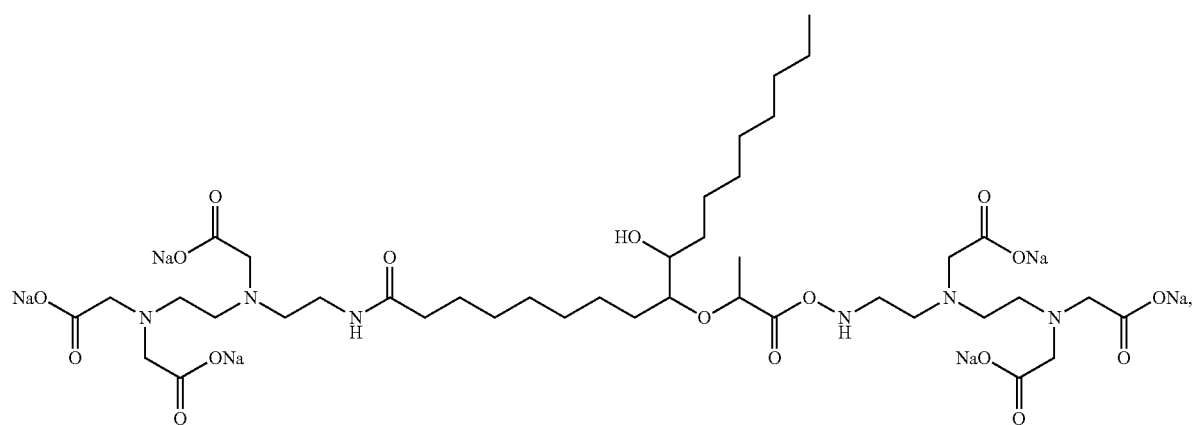
Candidate 50
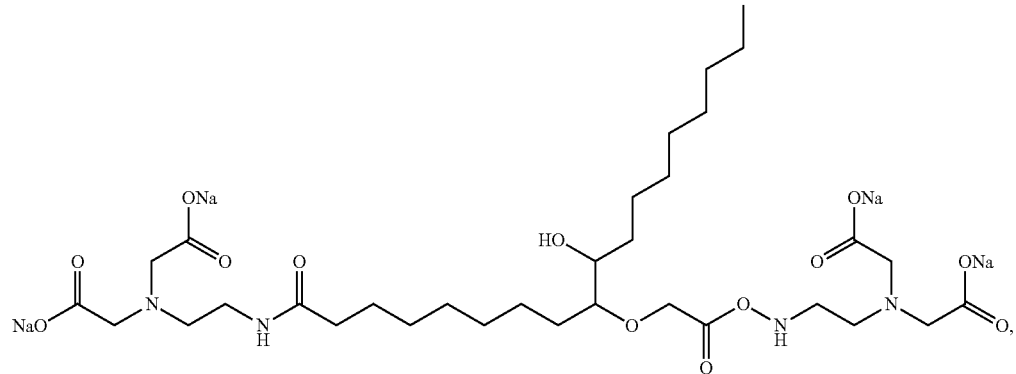
Candidate 51
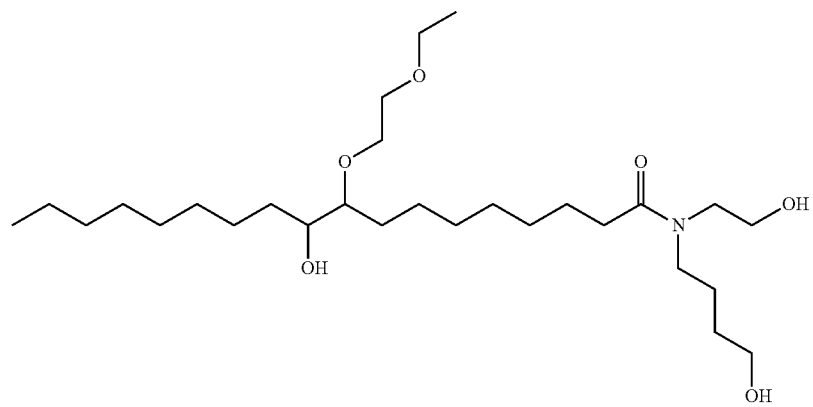

Candidate 52
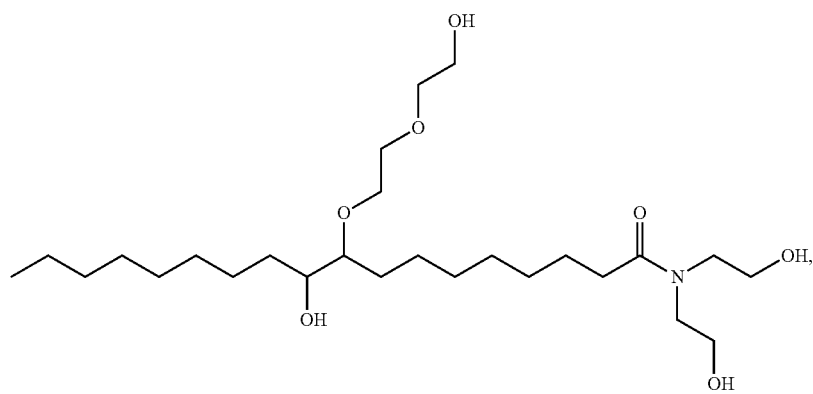
Candidate 53
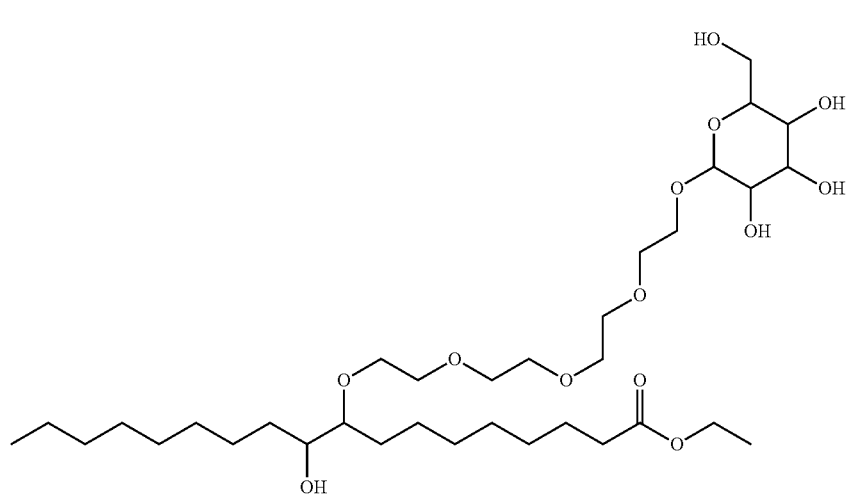
Candidate 54
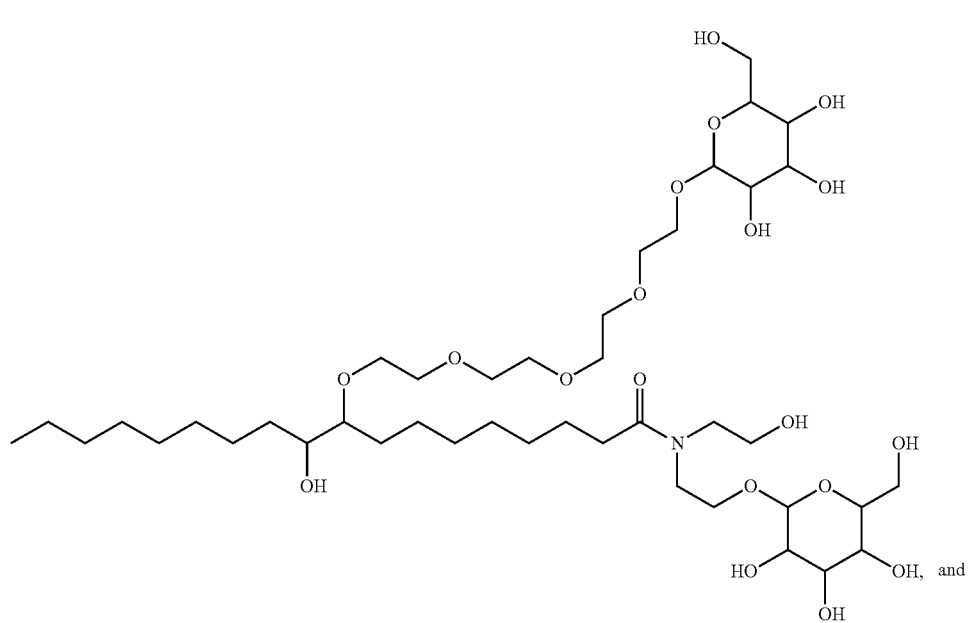
, and

Candidate 55

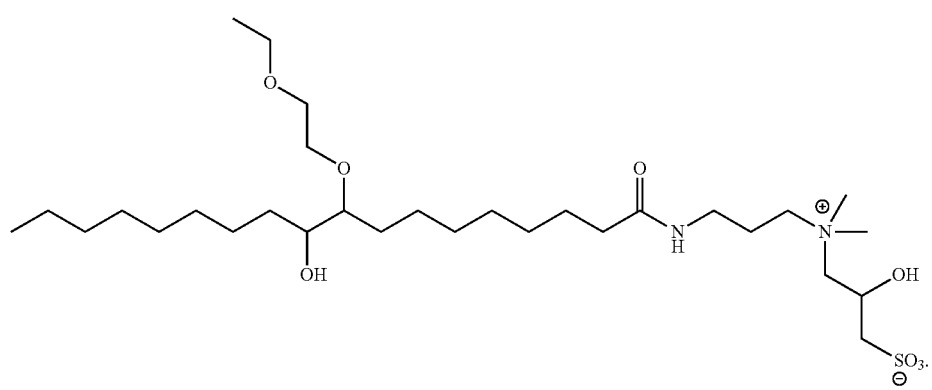

3. The composition of claim 1 comprising candidate 48 mixed with SDBS in a weight ratio in the range of 1:10 to 10:1.

4. The composition of claim 1 wherein candidate 48 is at least 50% biobased carbon.

5. The composition of claim 1 further comprising one or more of candidates 25, 32, and 43.

6. A method of washing laundry, comprising contacting dirty laundry with the composition of claim 1.

7. An intermediate composition comprising:

Candidate 48

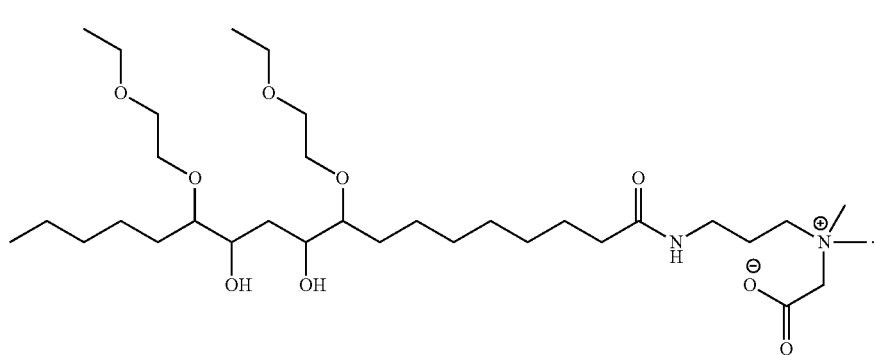

8. The composition of claim 1 comprising at least 2 wt % of one or more compounds selected from:

Candidate 14

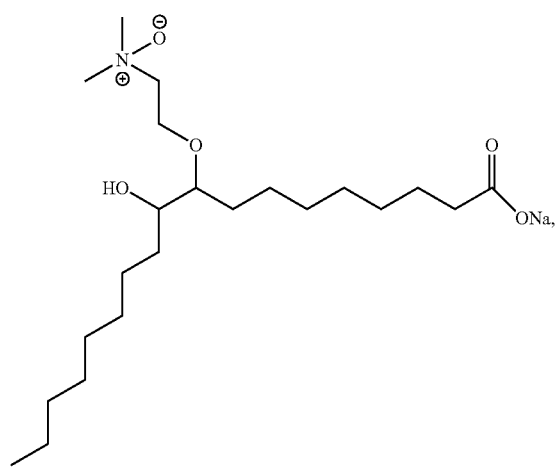

Candidate 15

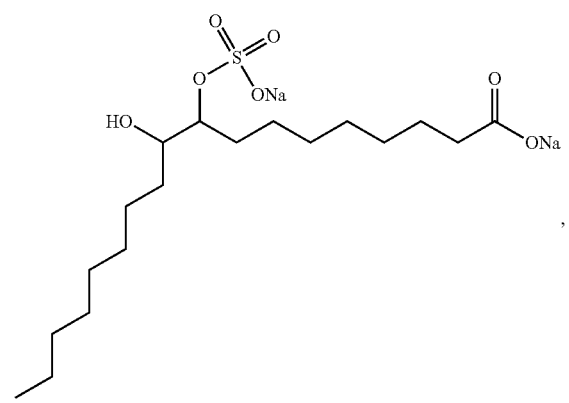

-continued
Candidate 16
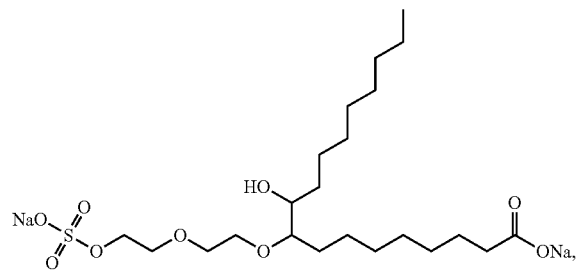
Candidate 17
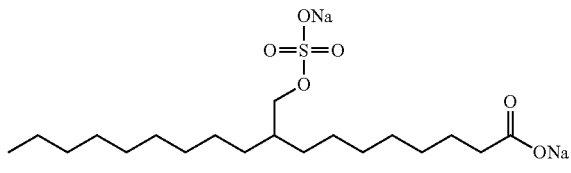
Candidate 18
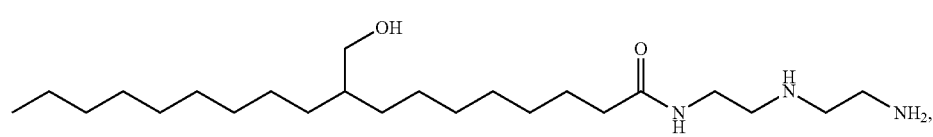
Candidate 19
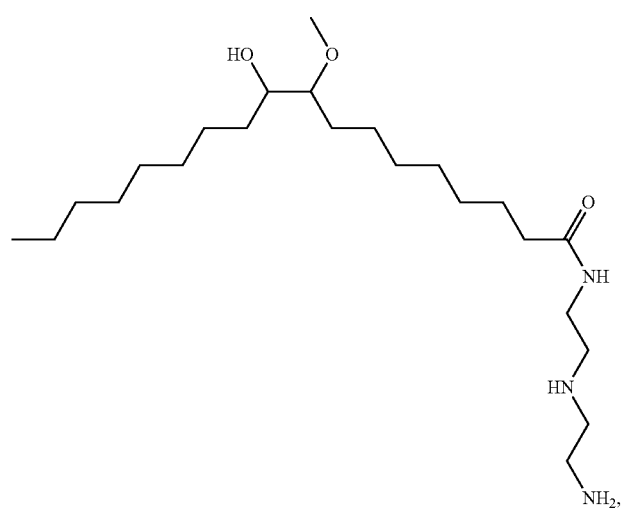
Candidate 20
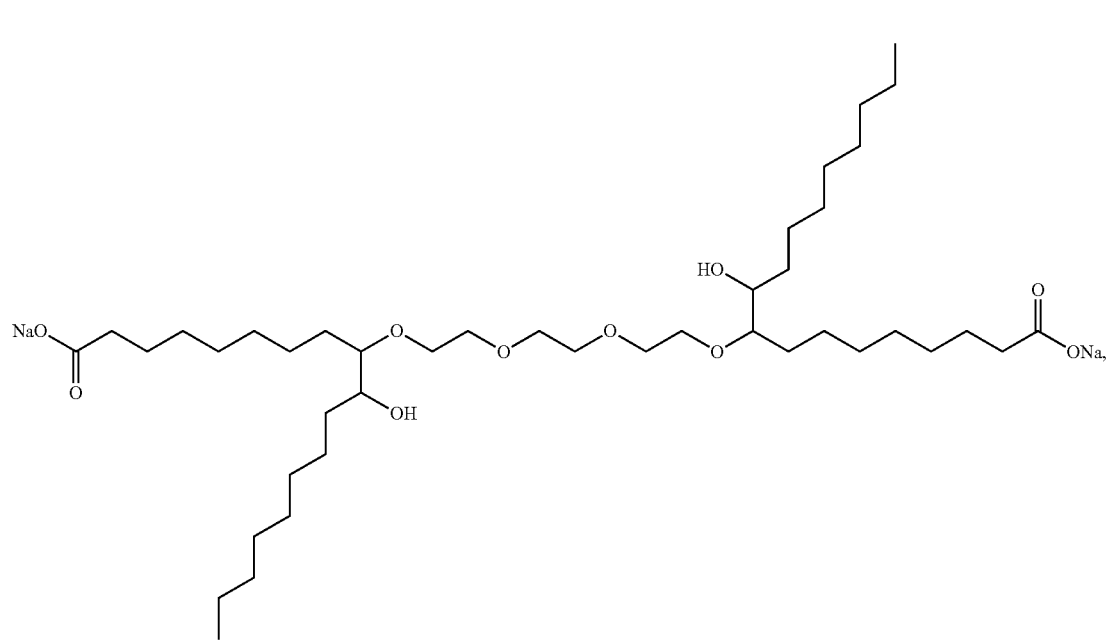

-continued
Candidate 21
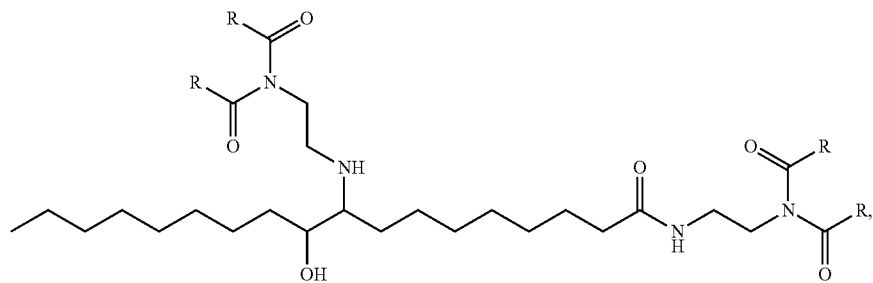
Candidate 22
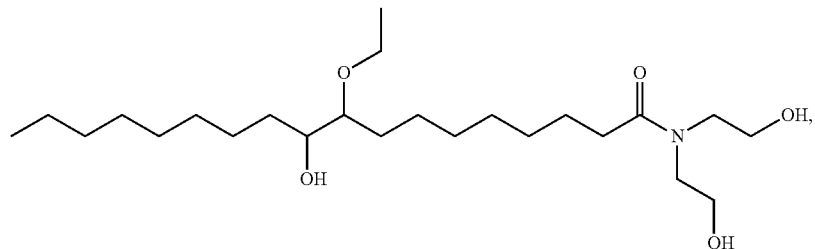
Candidate 23
Candidate 24
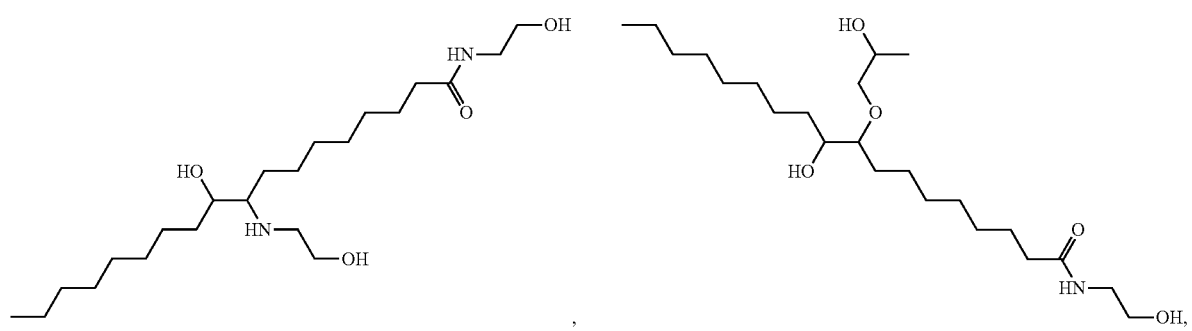
Candidate 25
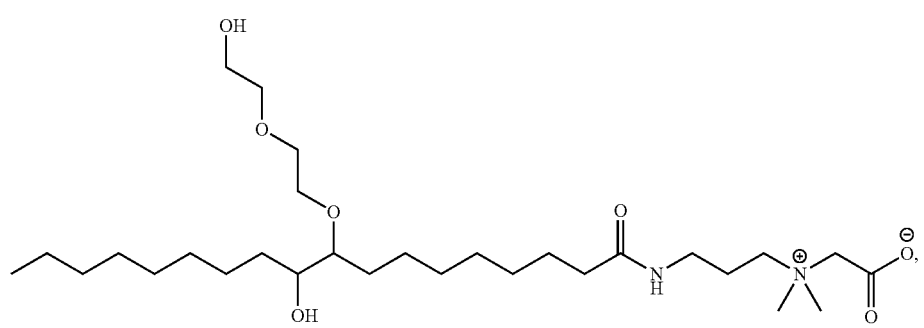
Candidate 26
Candidate 27
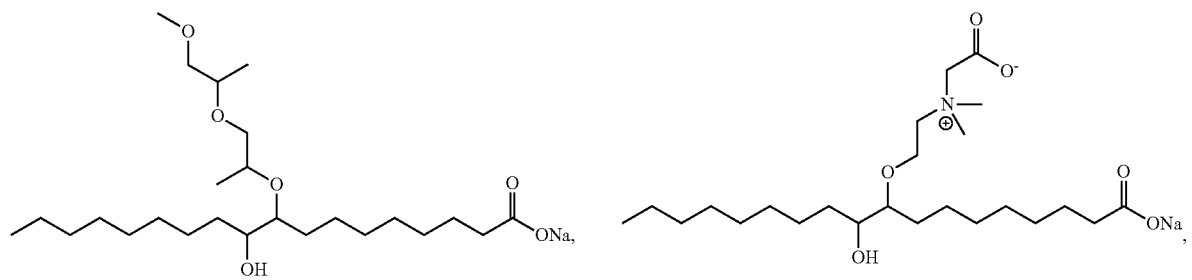

Candidate 28
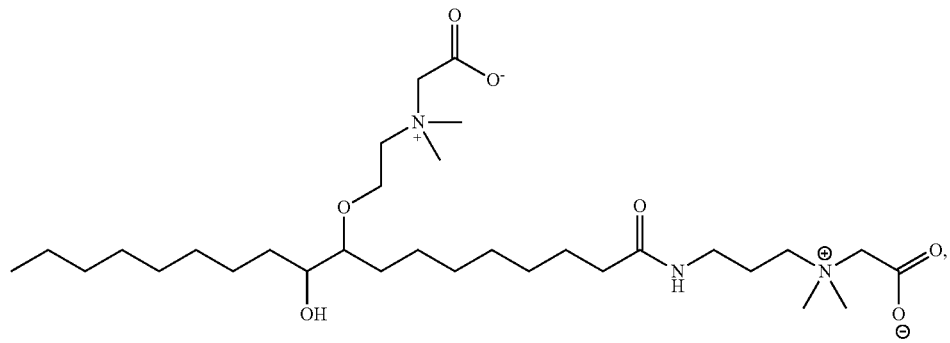
Candidate 29
Candidate 30
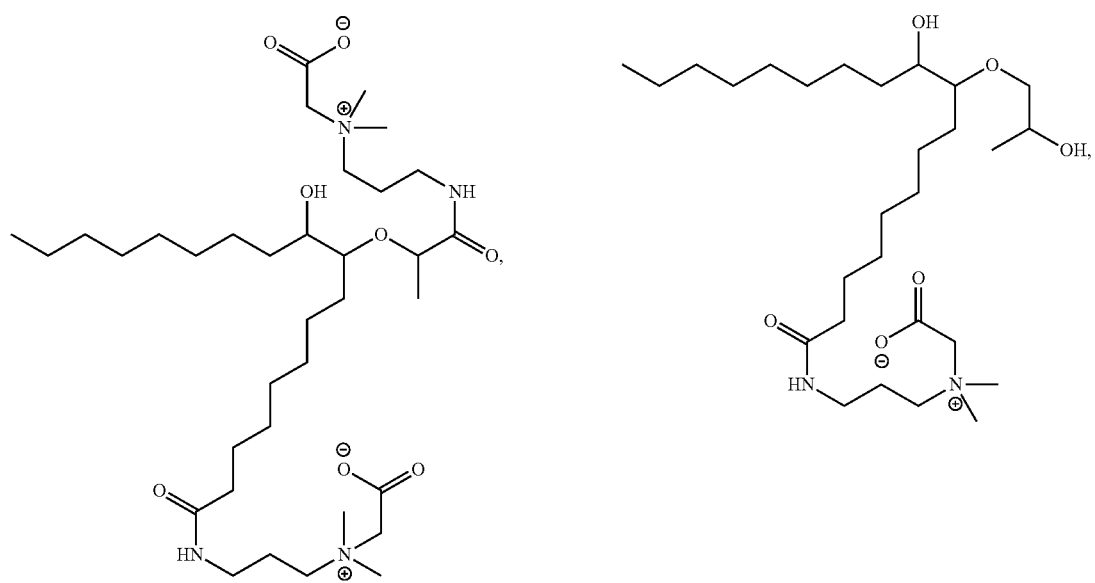
Candidate 31
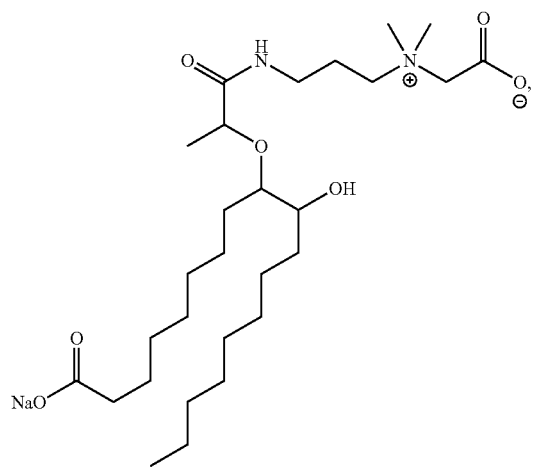

Candidate 32
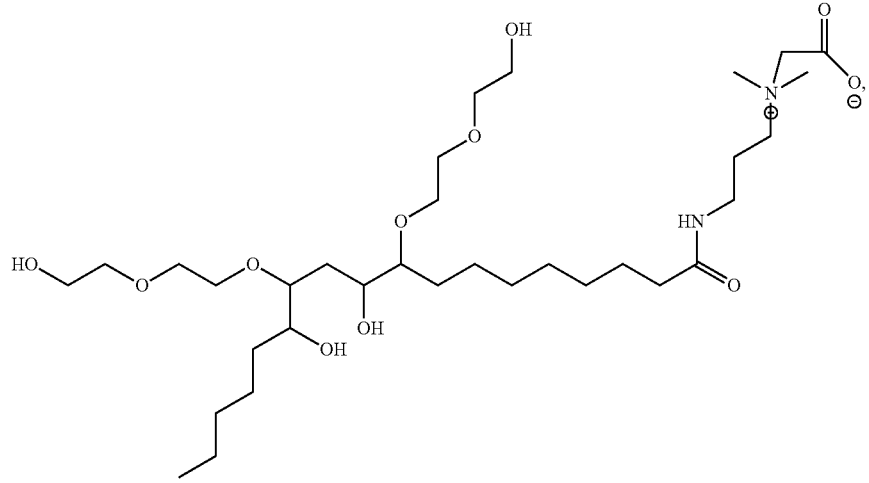
Candidate 34
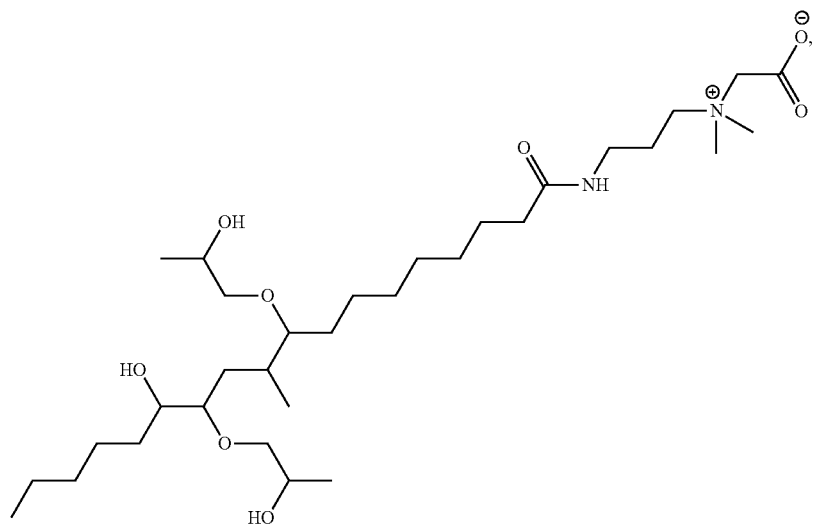
Candidate 35
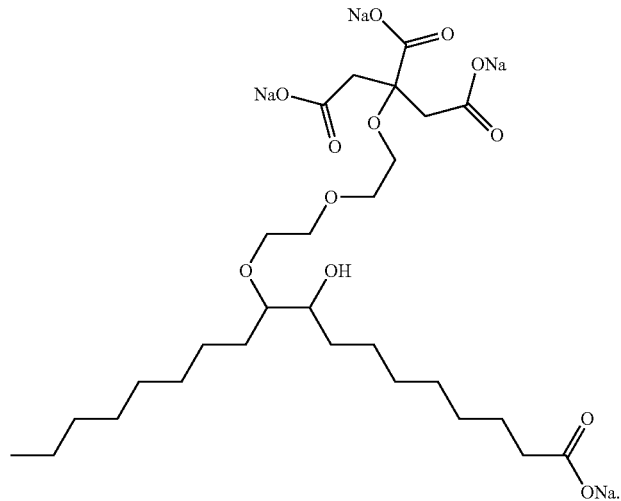

Candidate 36
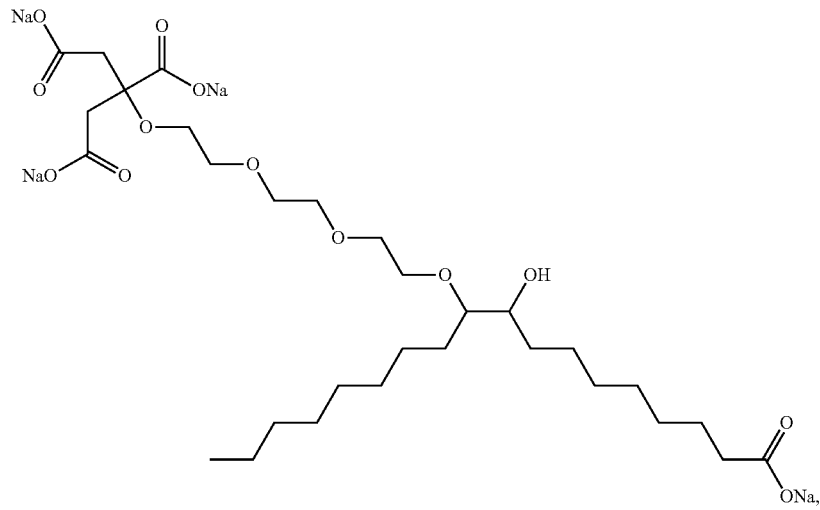
Candidate 37
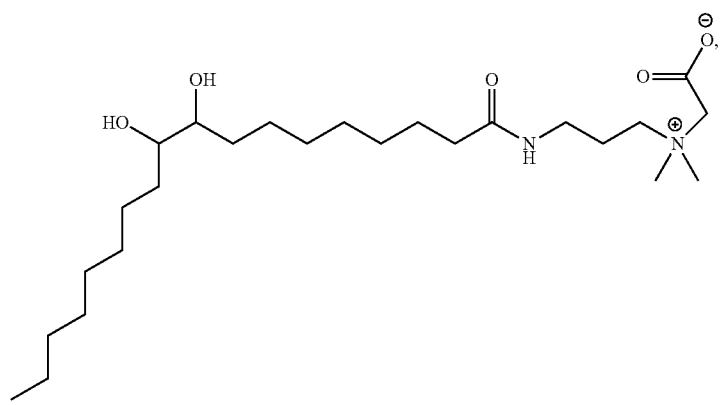
Candidate 38
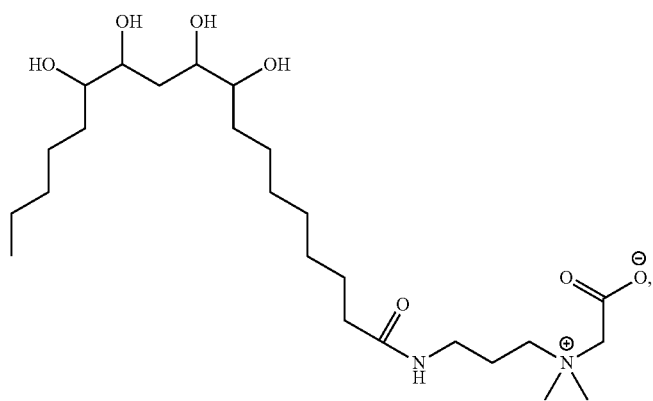

Candidate 39
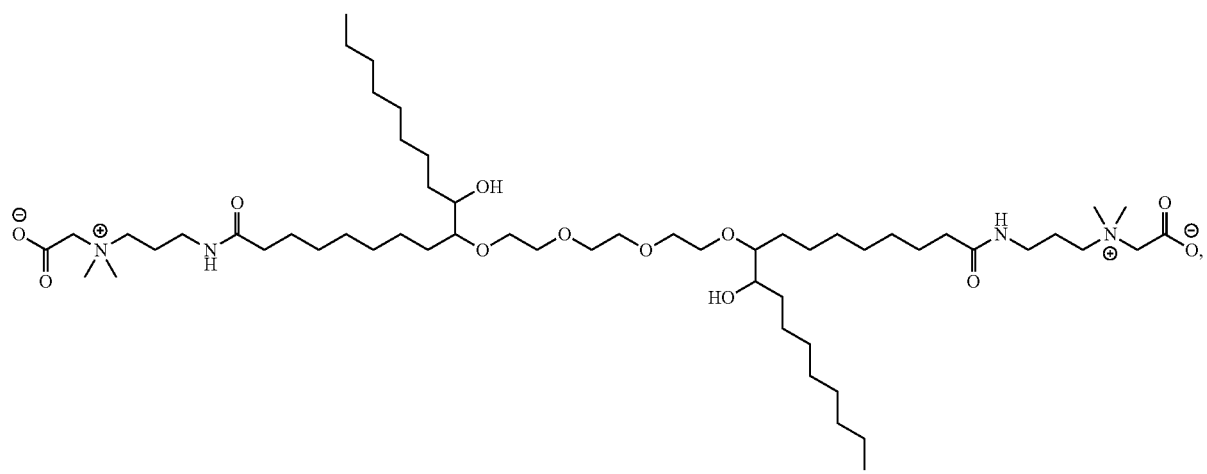
Candidate 40
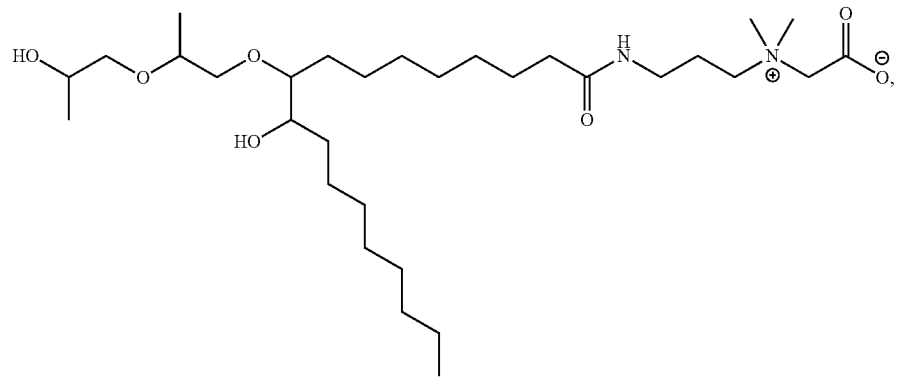
Candidate 41
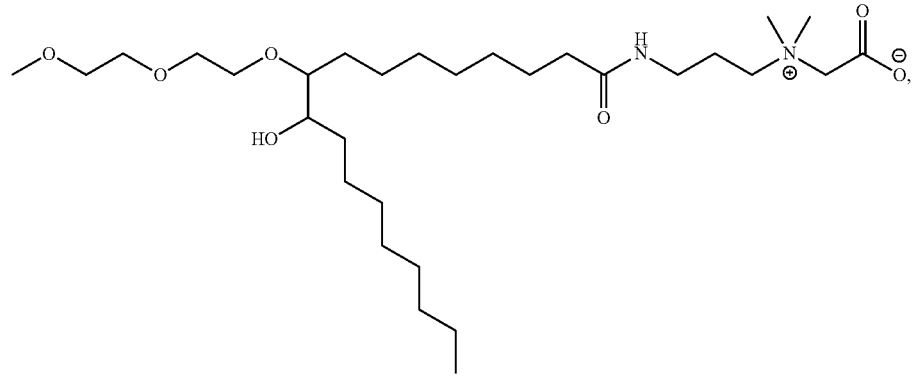
Candidate 42
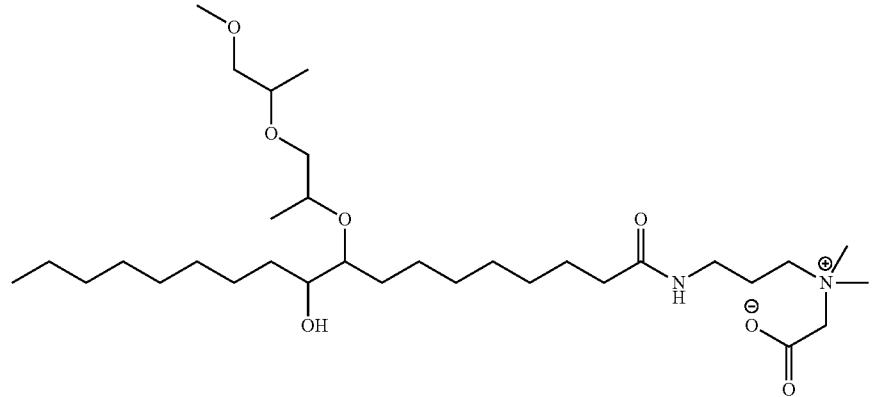

-continued
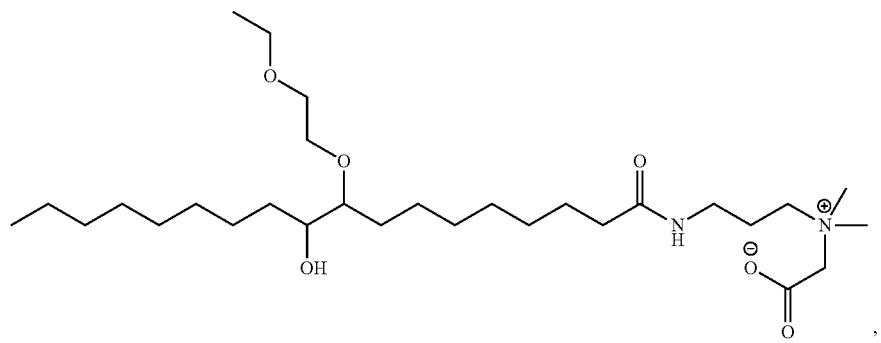
Candidate 43
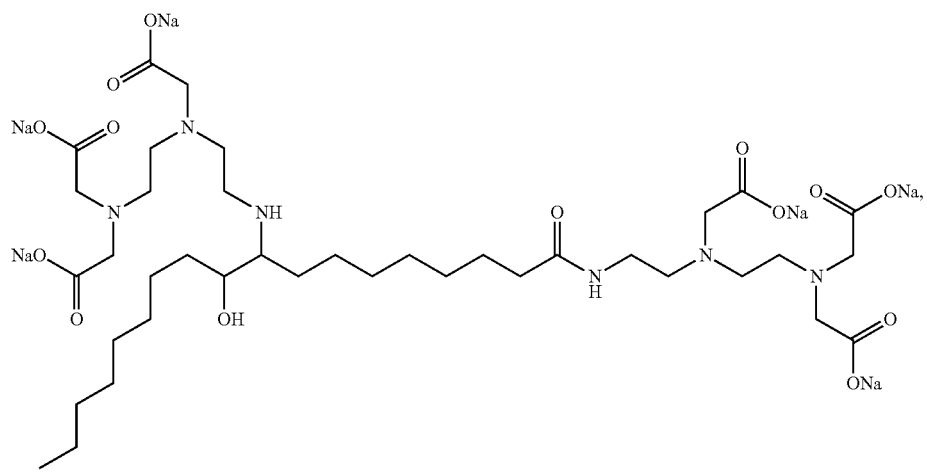
Candidate 44
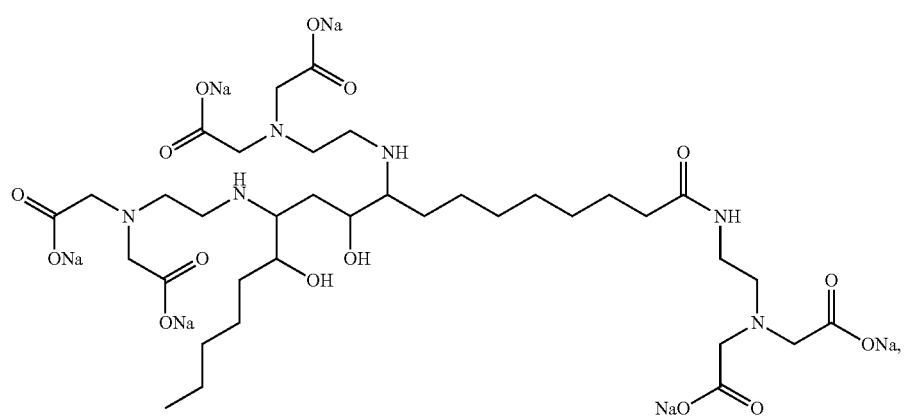
Candidate 45

-continued
Candidate 46
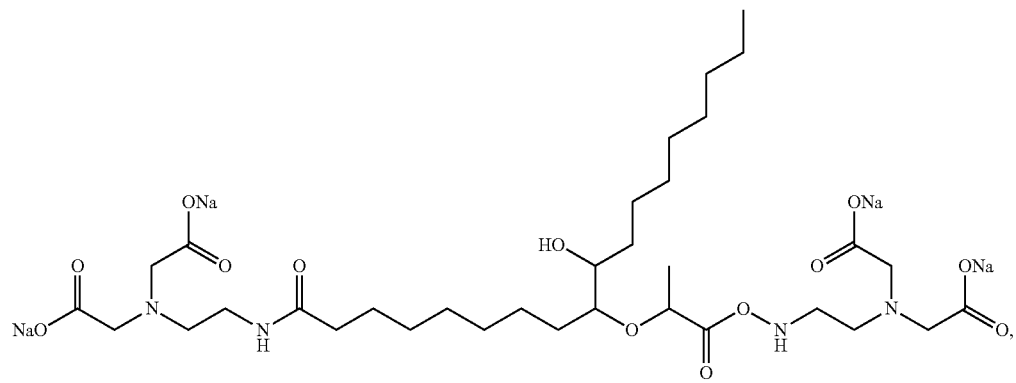
Candidate 47
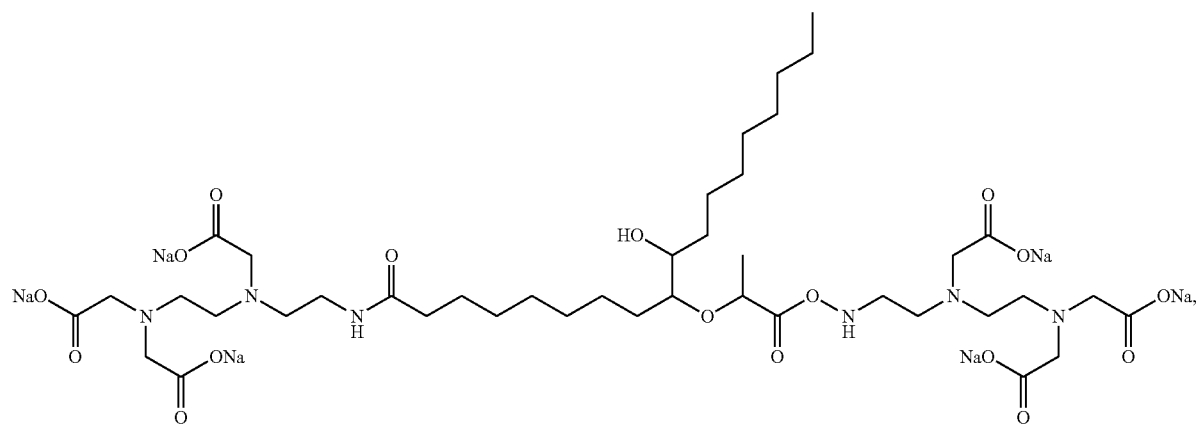
Candidate 50
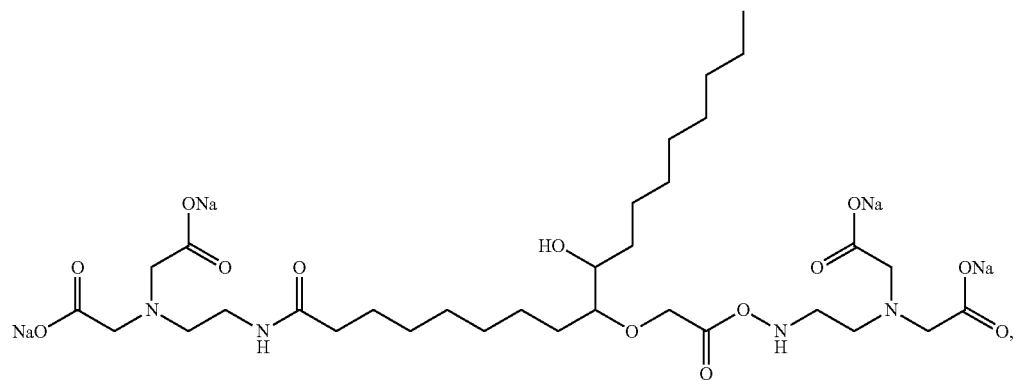
Candidate 51
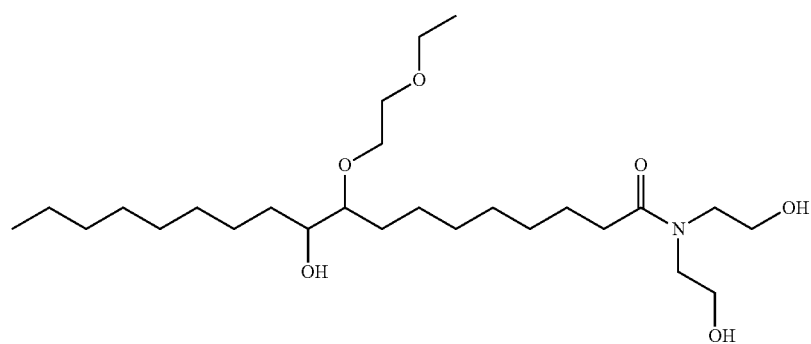

-continued
Candidate 52
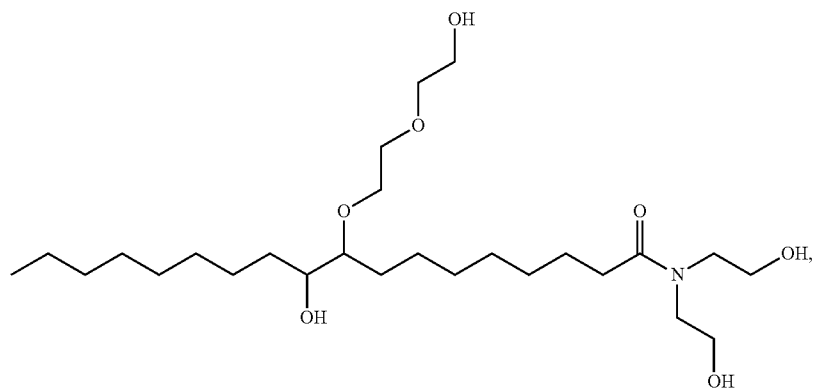
Candidate 53
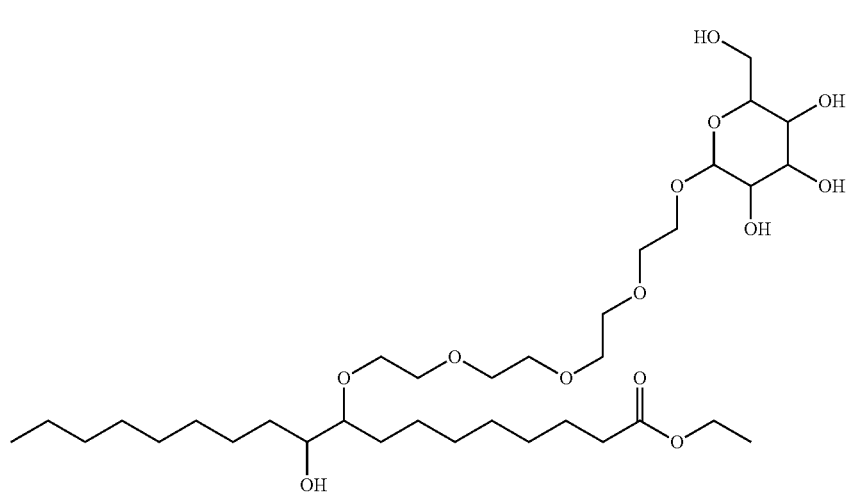
Candidate 54
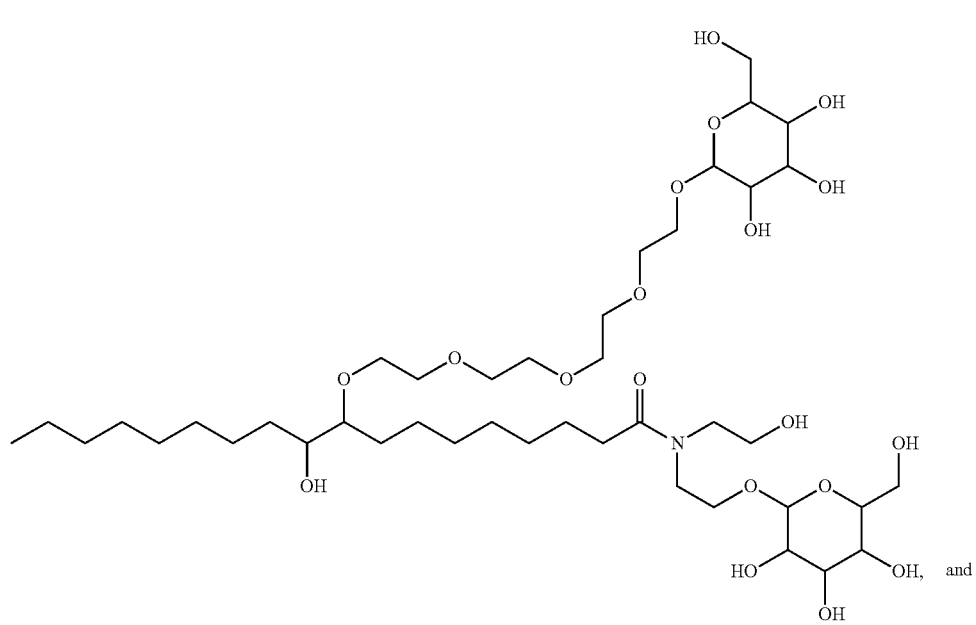
and Candidate 55

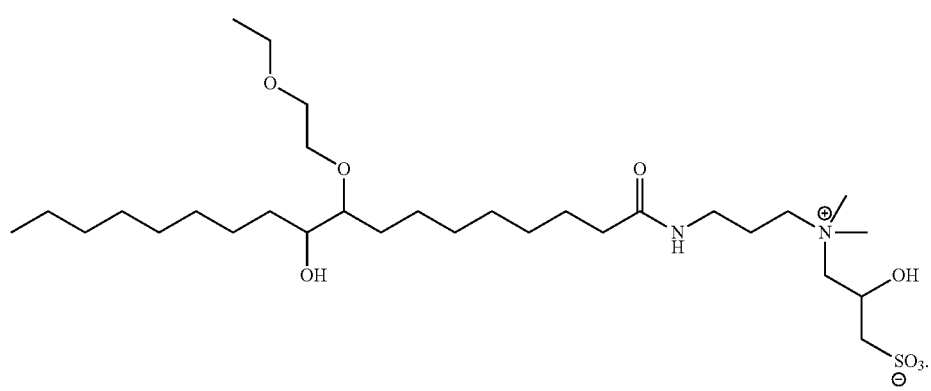

9. The composition of claim 1 comprising candidate 48 mixed with SDBS in a weight ratio in the range of 2:1 to 1:2.

10. The composition of claim 1 wherein candidate 48 is at least 70% biobased carbon.

11. The composition of claim 2 comprising at least 5 wt % of one or more compounds selected from candidates 14-32, 34-48, and 50-55.

12. The composition of claim 3 further comprising one or more compounds selected from candidates 25, 32, and 43.

13. The composition of claim 8 comprising one or more compounds selected from candidates 25, 32, and 43.

14. The composition of claim 2 comprising at least 0.5 wt % of candidate 25.

15. The composition of claim 2 comprising at least 0.5 wt % of candidate 32.

16. The composition of claim 2 comprising at least 0.5 wt % of candidate 43.

17. The composition of claim 1 comprising at least 0.5 wt % of candidate 48.

18. The composition of claim 1 further comprising one or more compounds selected from:

Candidate 14

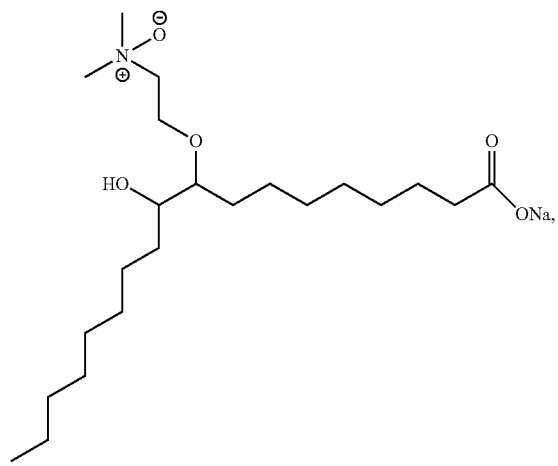

Candidate 15

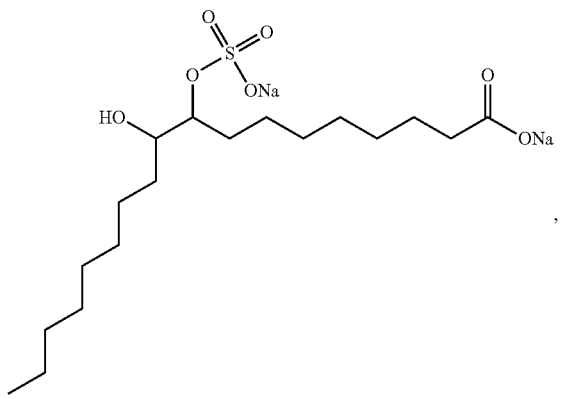

Candidate 16

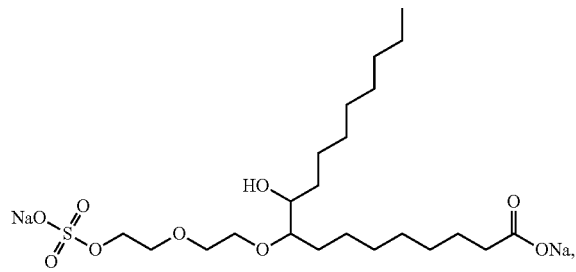

Candidate 17

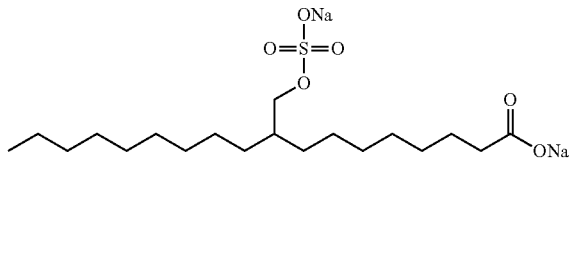

-continued
Candidate 18
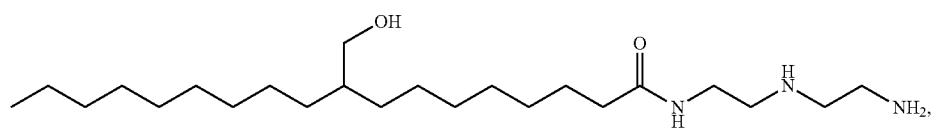
Candidate 19
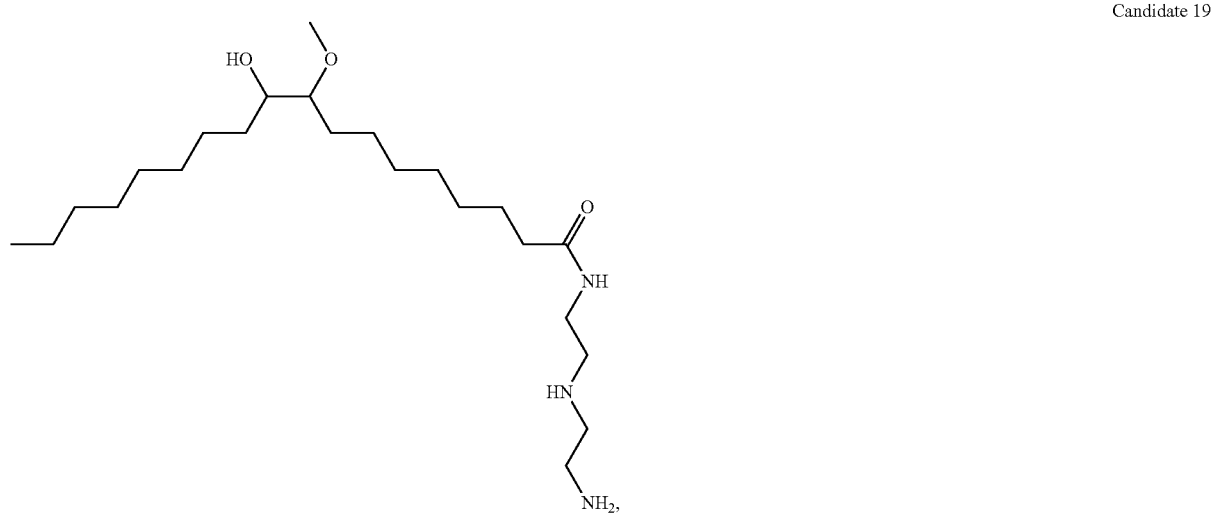
Candidate 20
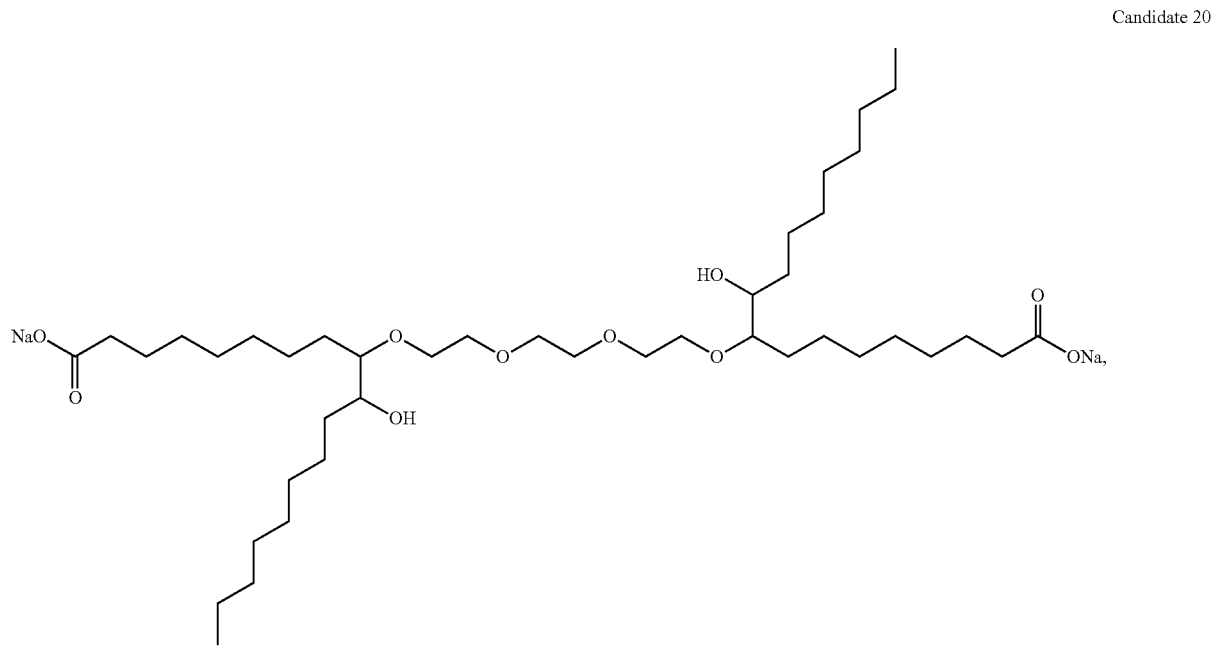
Candidate 21
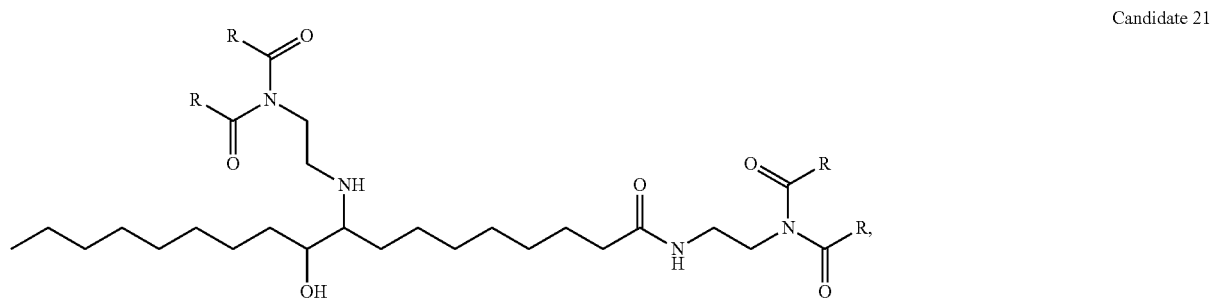

Candidate 22
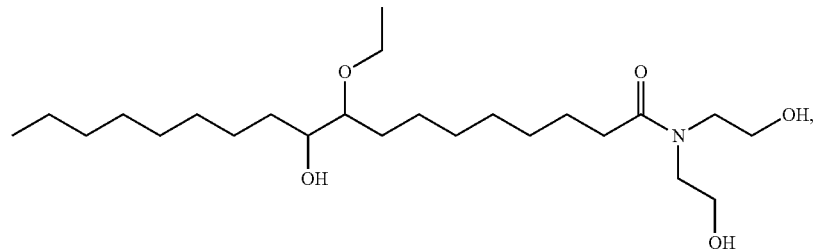
Candidate 23
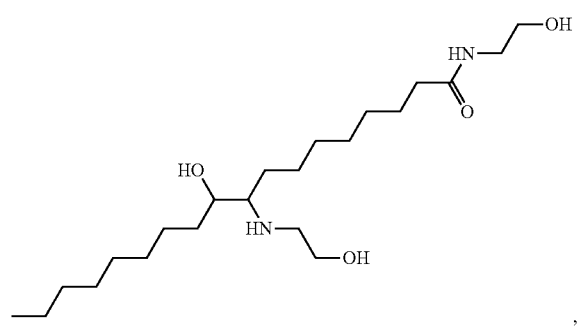
Candidate 24
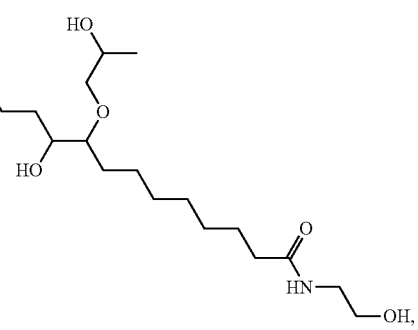
Candidate 25
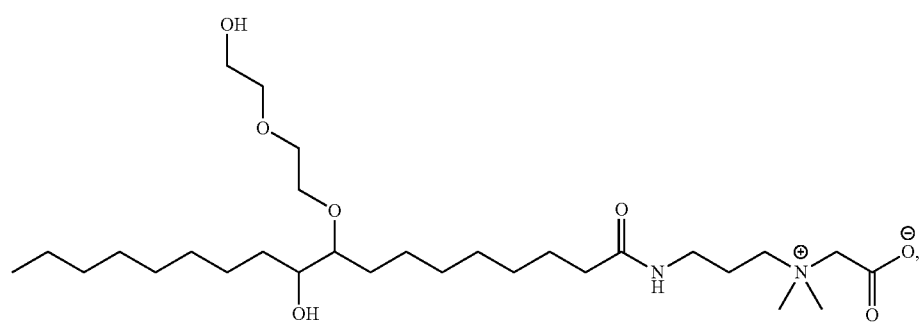
Candidate 26
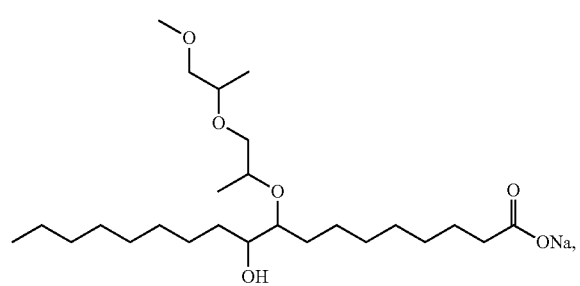
Candidate 27
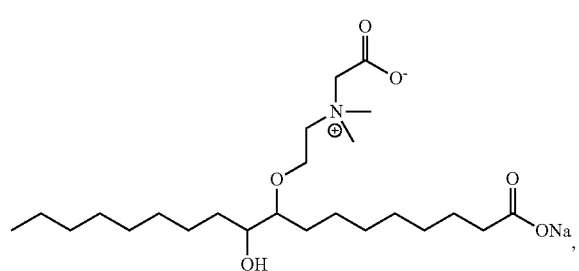
Candidate 28
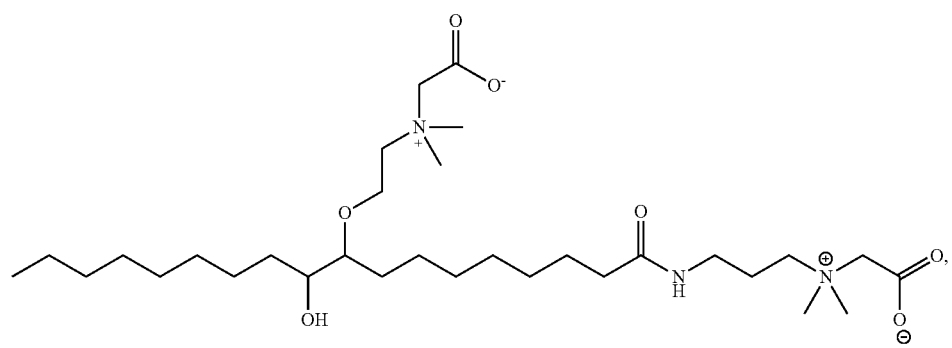

Candidate 29
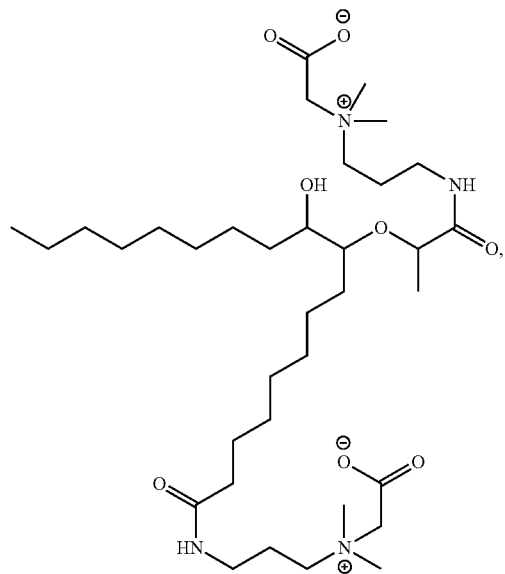
Candidate 30
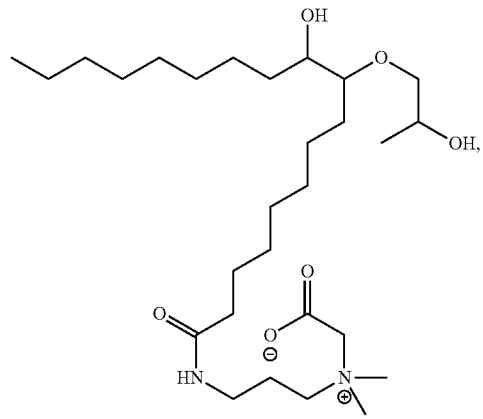
Candidate 31
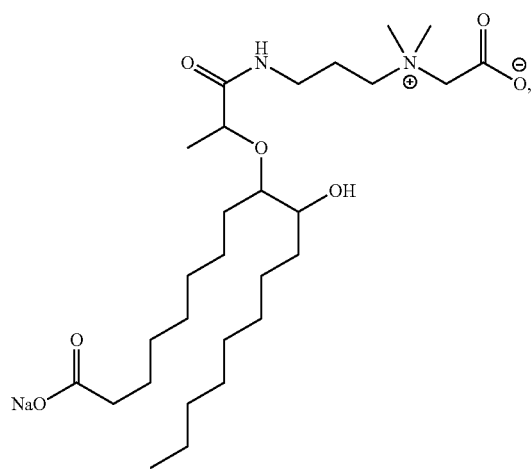
Candidate 32
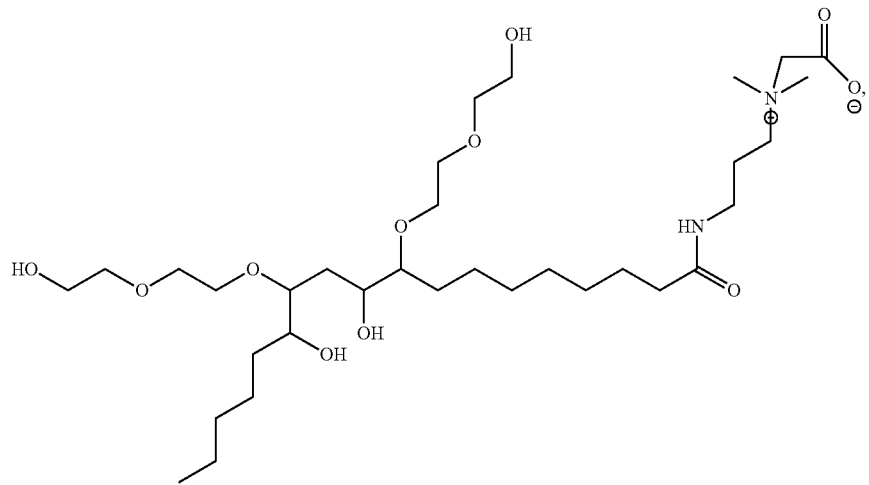

-continued
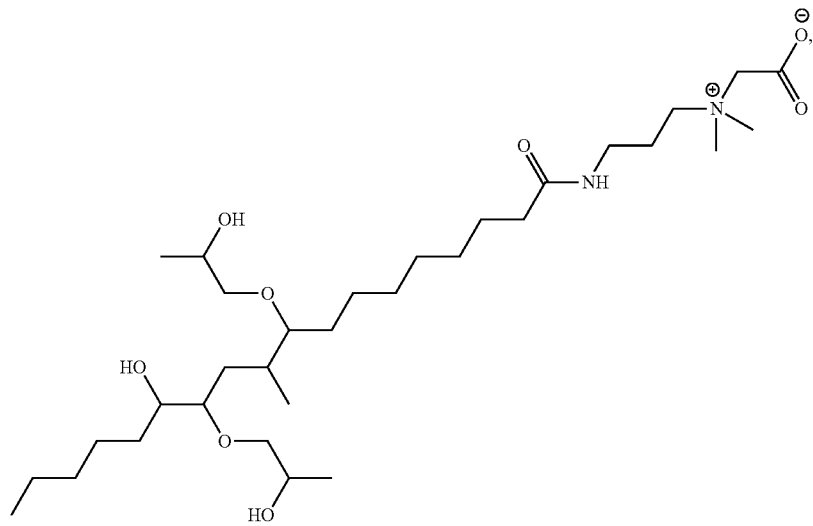
Candidate 34
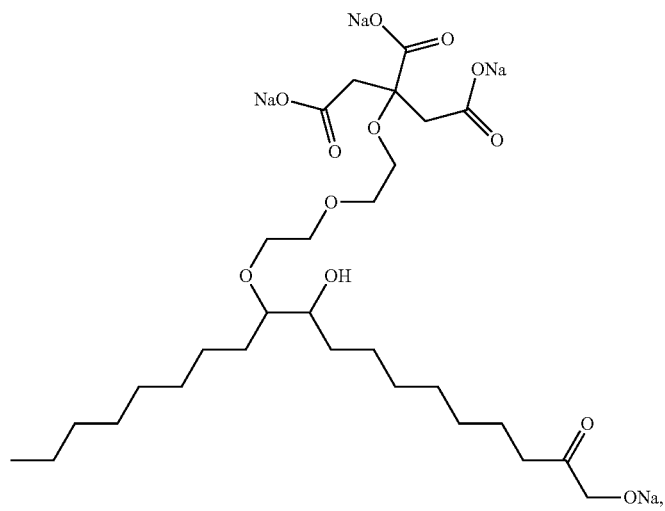
Candidate 35
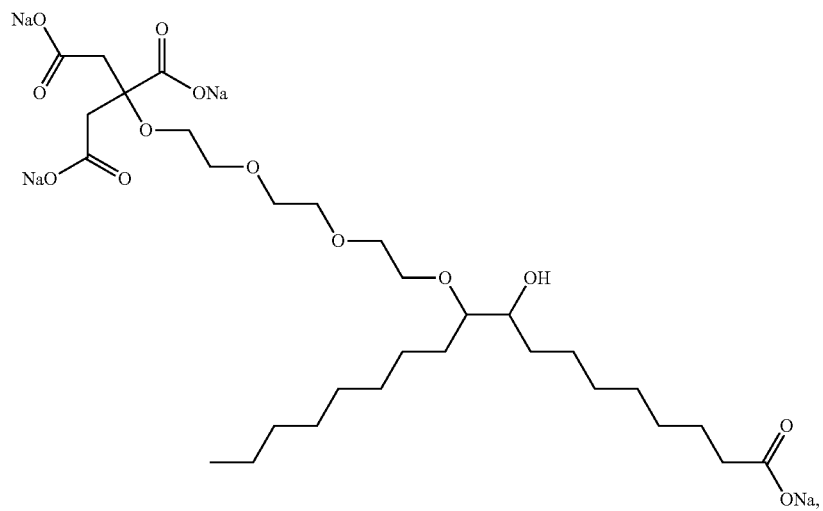
Candidate 36

-continued
Candidate 37
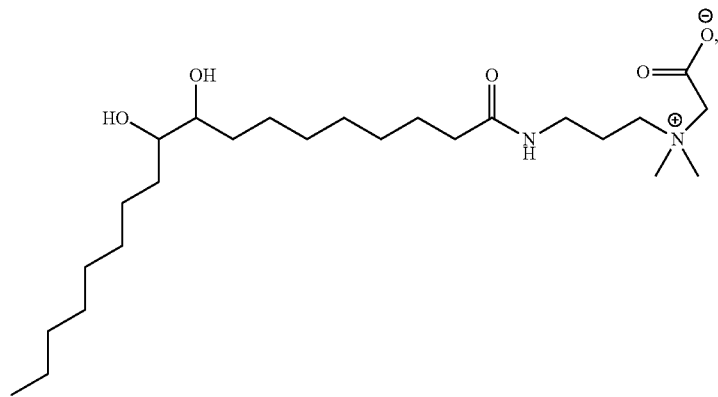
Candidate 38
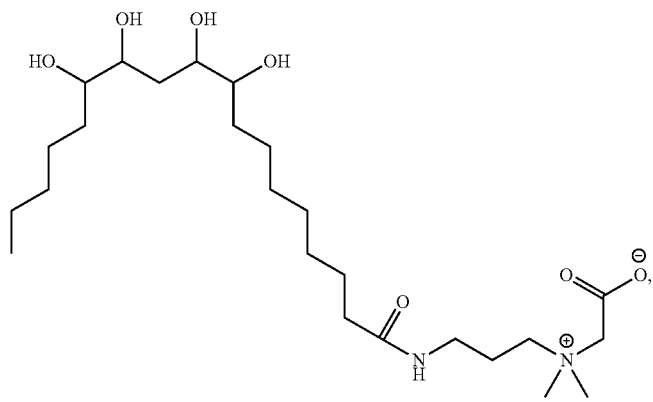
Candidate 39
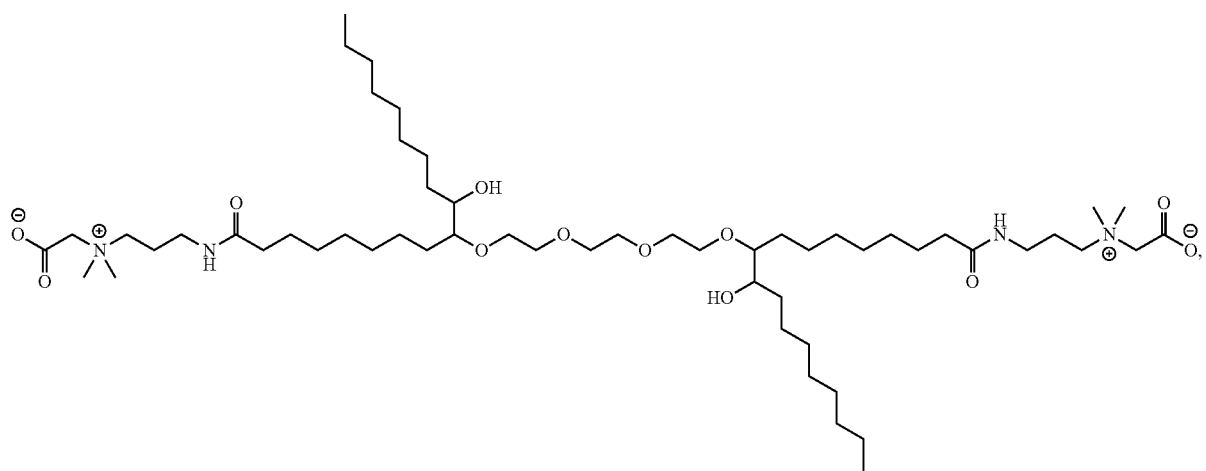

-continued
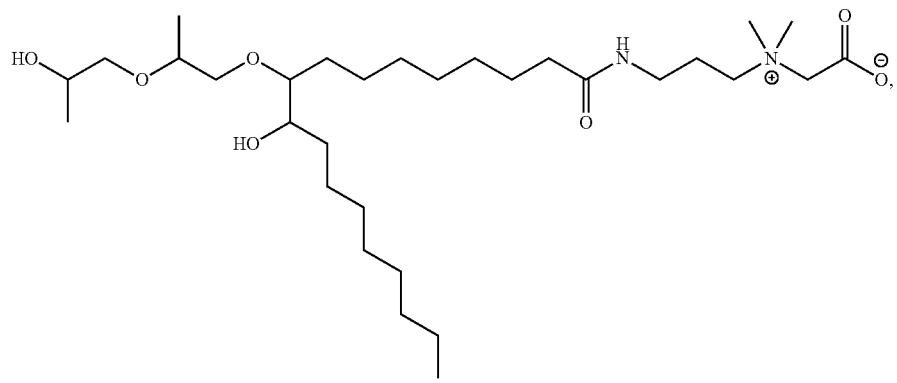
Candidate 40
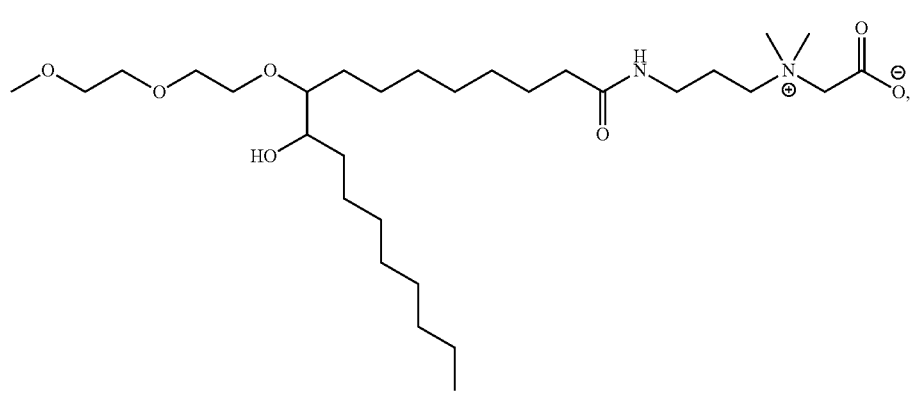
Candidate 41
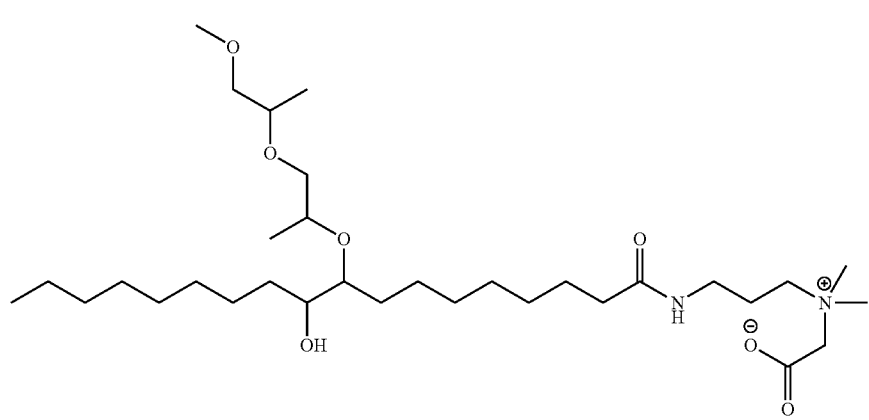
Candidate 42
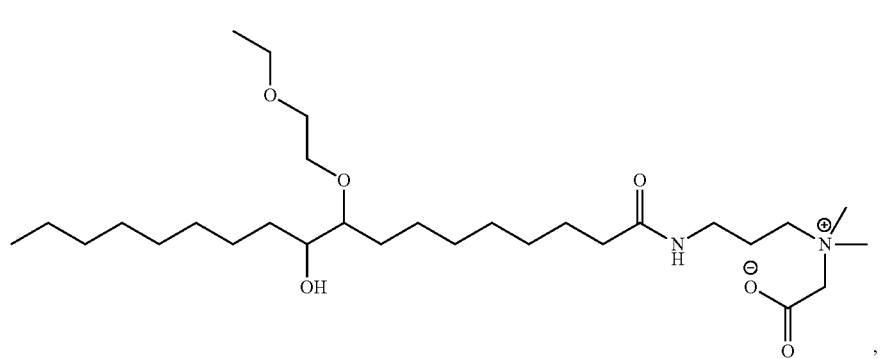
Candidate 43

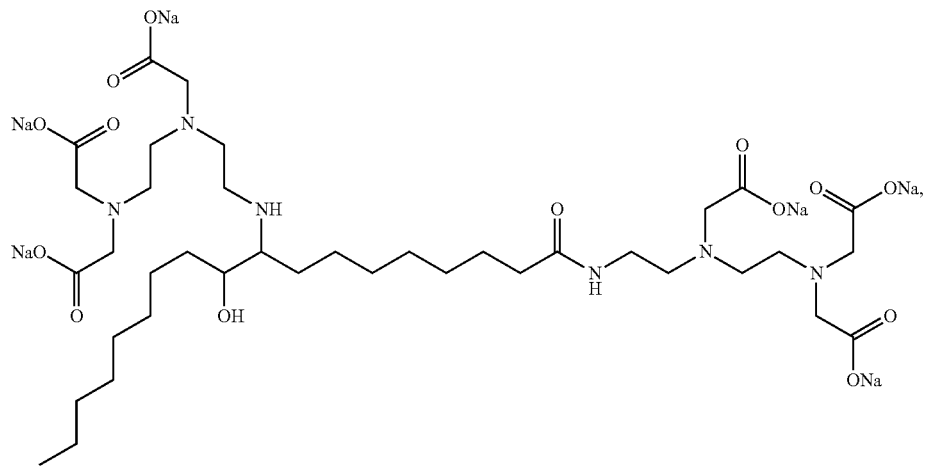
Candidate 44
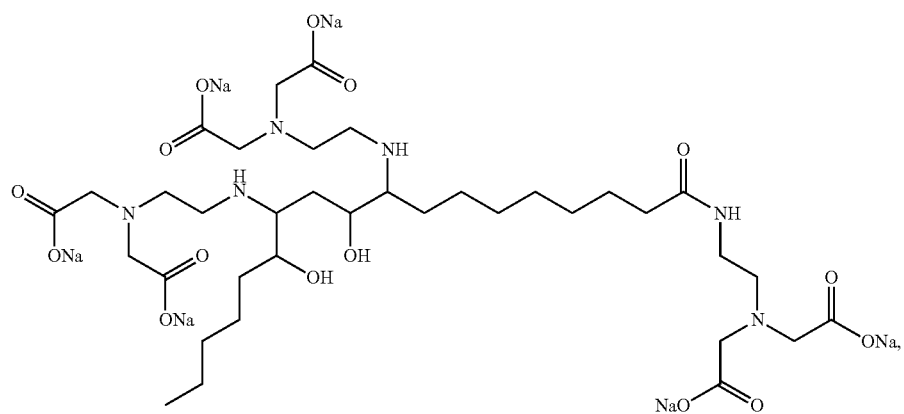
Candidate 45
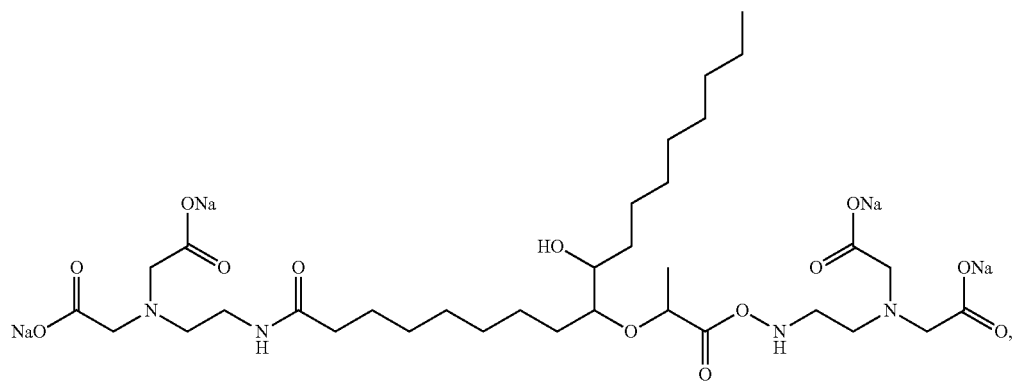
Candidate 46

-continued
Candidate 47
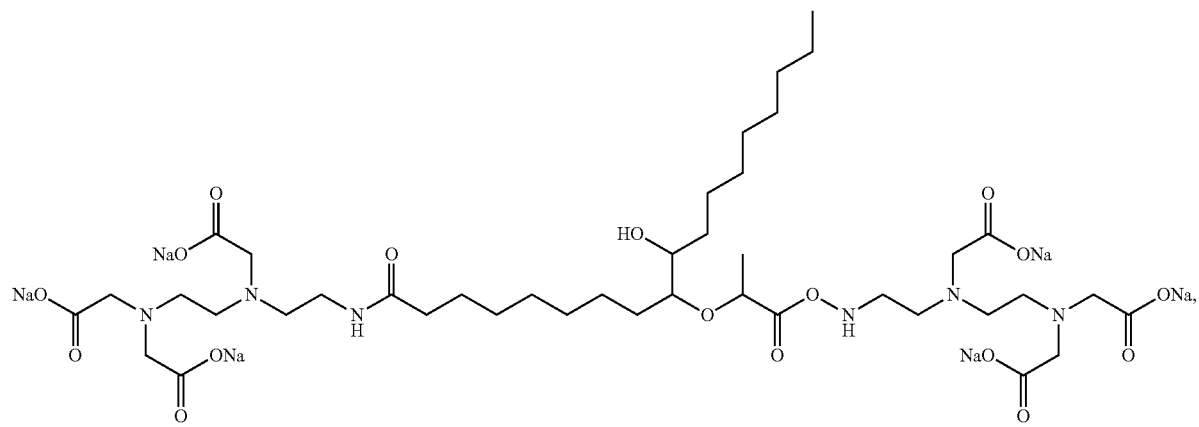
Candidate 50
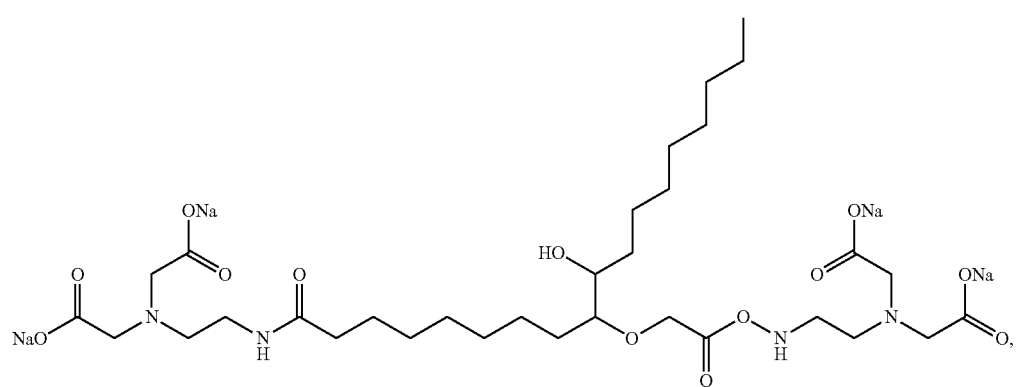
Candidate 51
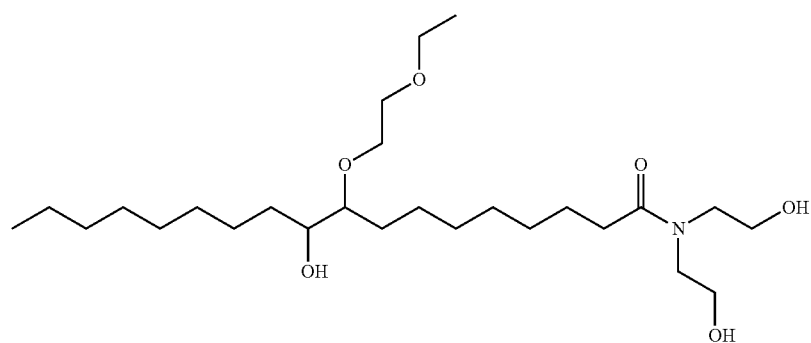
Candidate 52
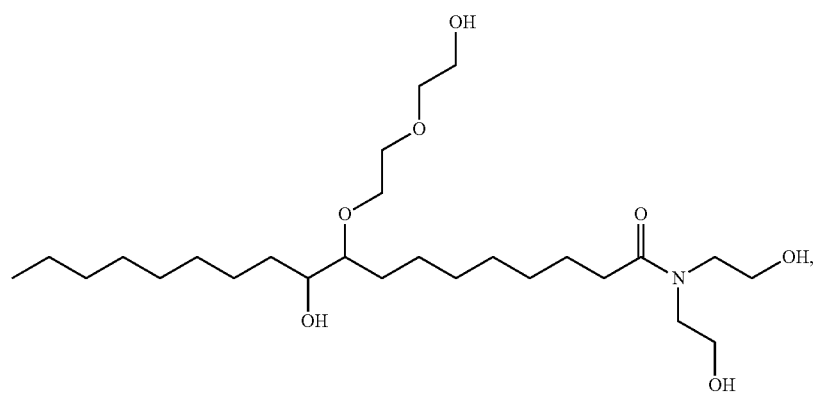

Candidate 53
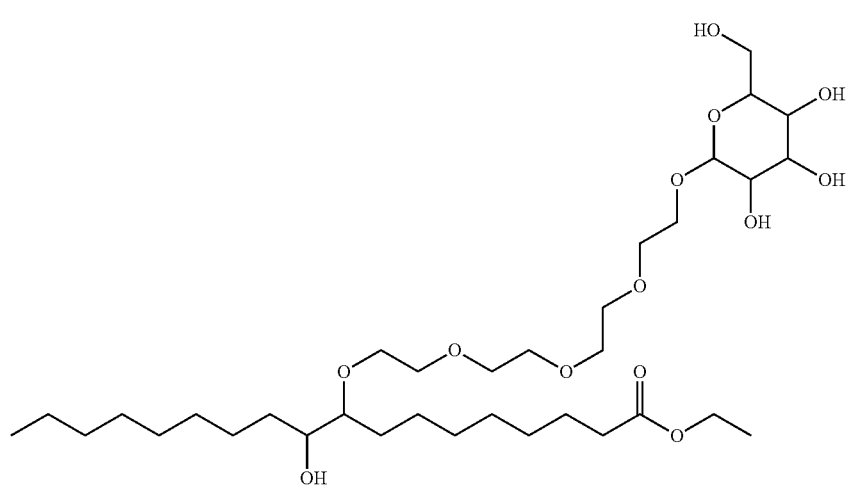
Candidate 54
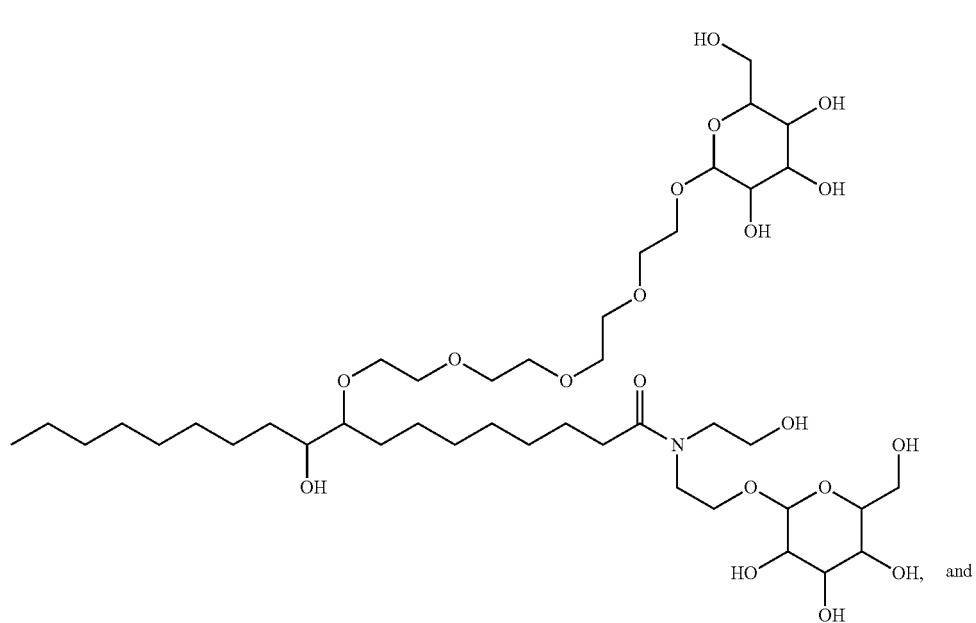
and
Candidate 55
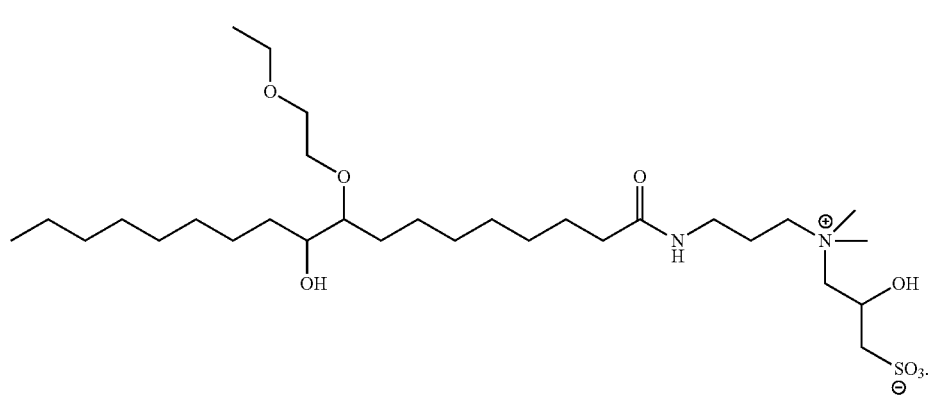

19. The intermediate composition of claim 7 comprising one or more compounds selected from:
Candidate 14
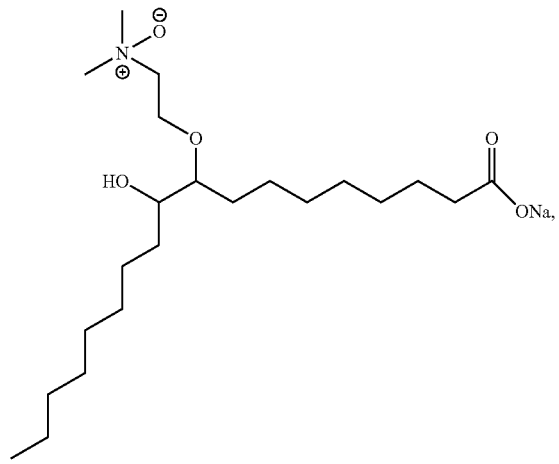
Candidate 15
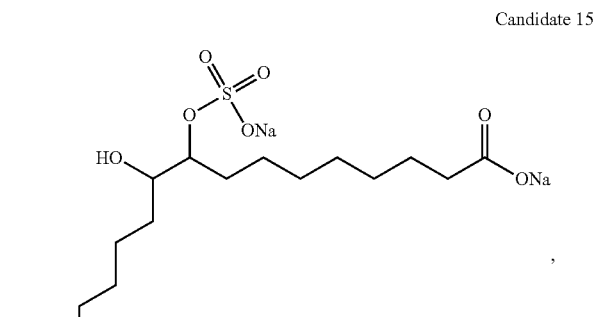
Candidate 16
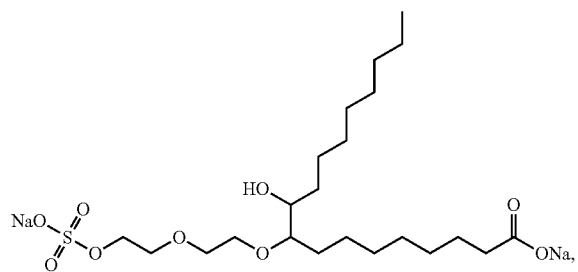
Candidate 17
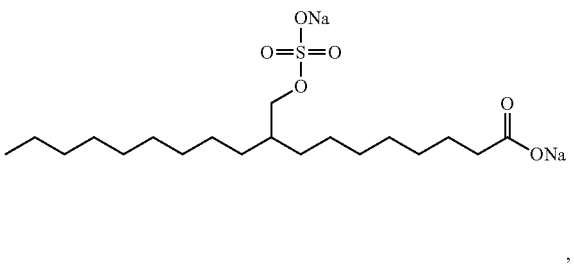
Candidate 18
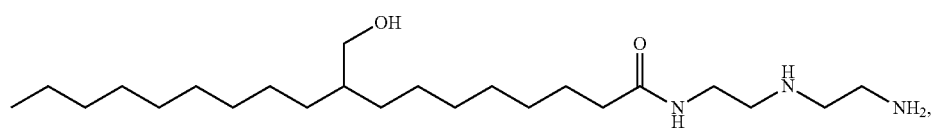
Candidate 19
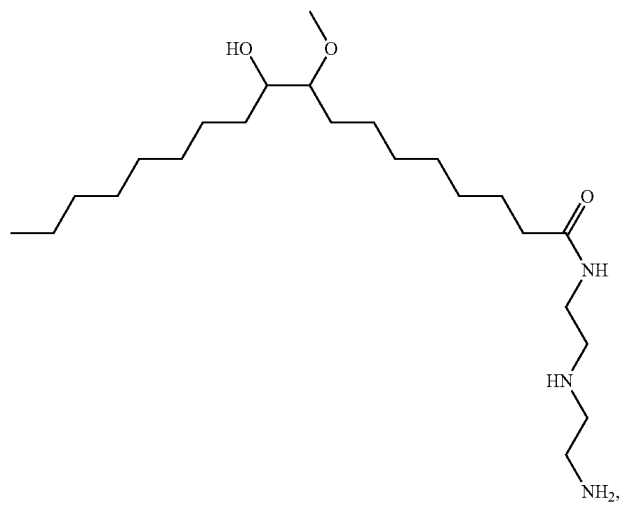

Candidate 20
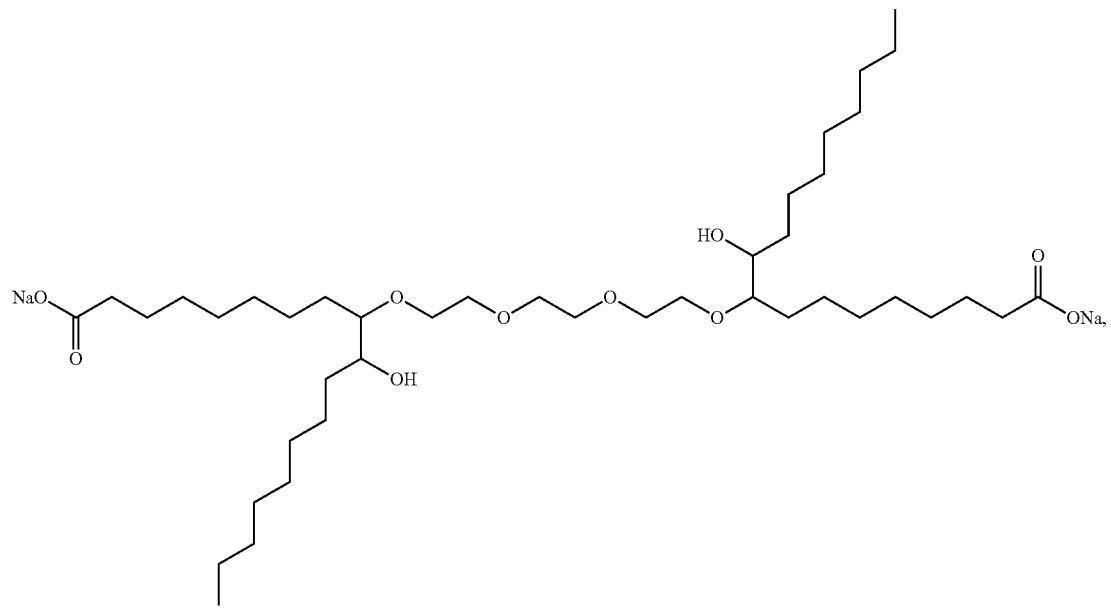
Candidate 21
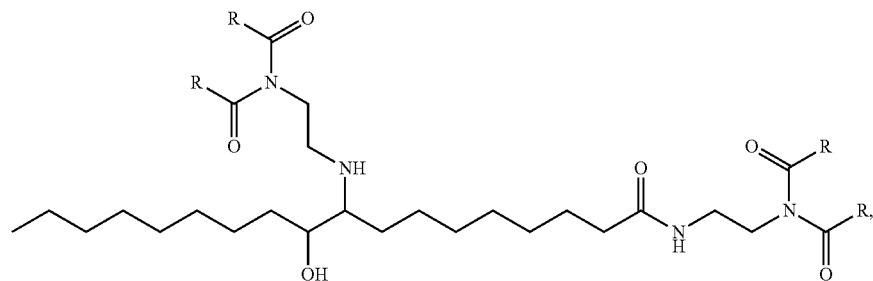
Candidate 22
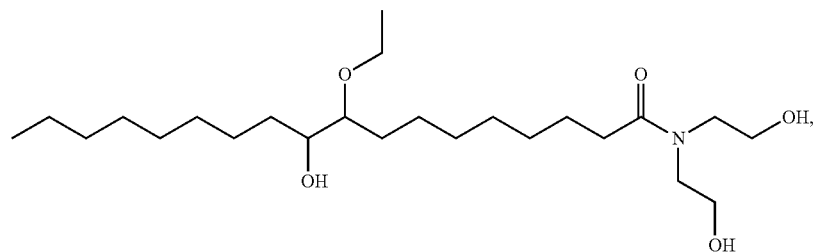
Candidate 23 Candidate 24
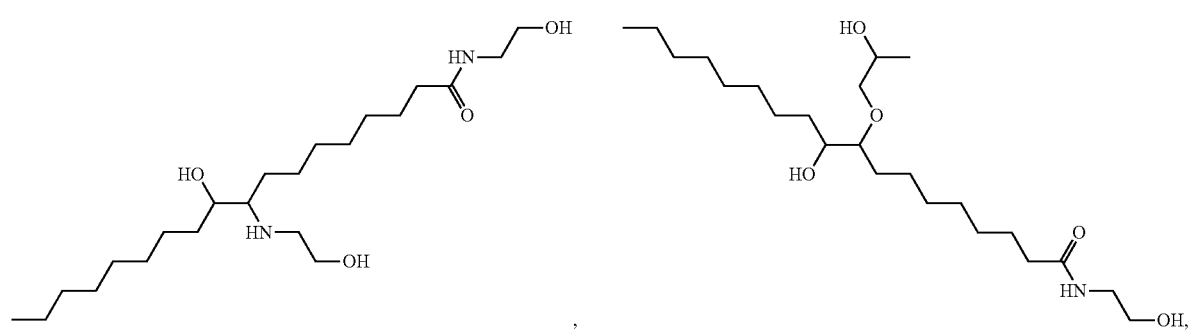

-continued
Candidate 25
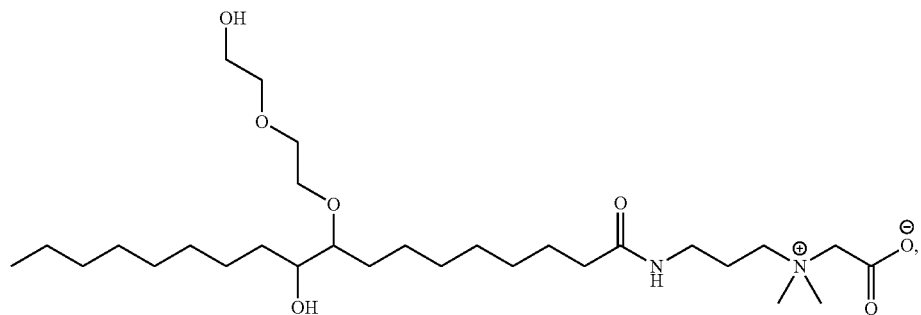
Candidate 26
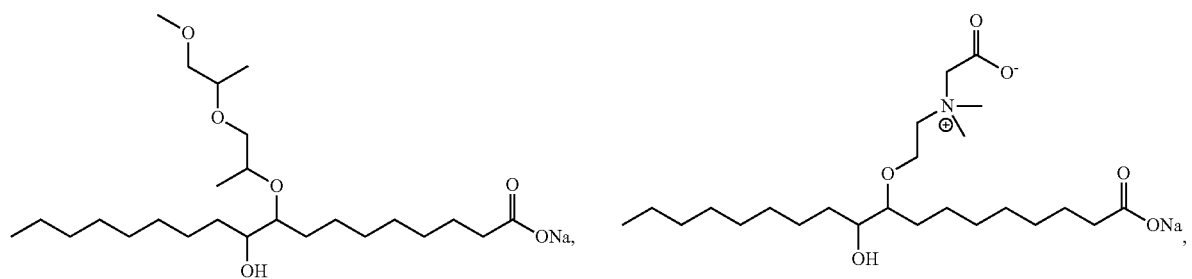
Candidate 27
Candidate 28
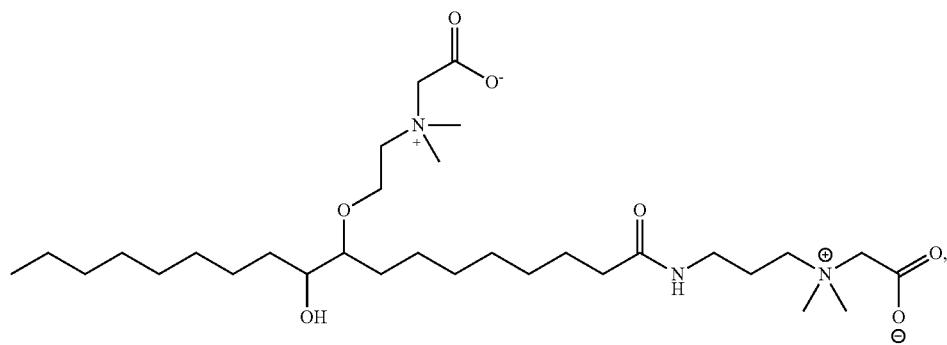
Candidate 29
Candidate 30
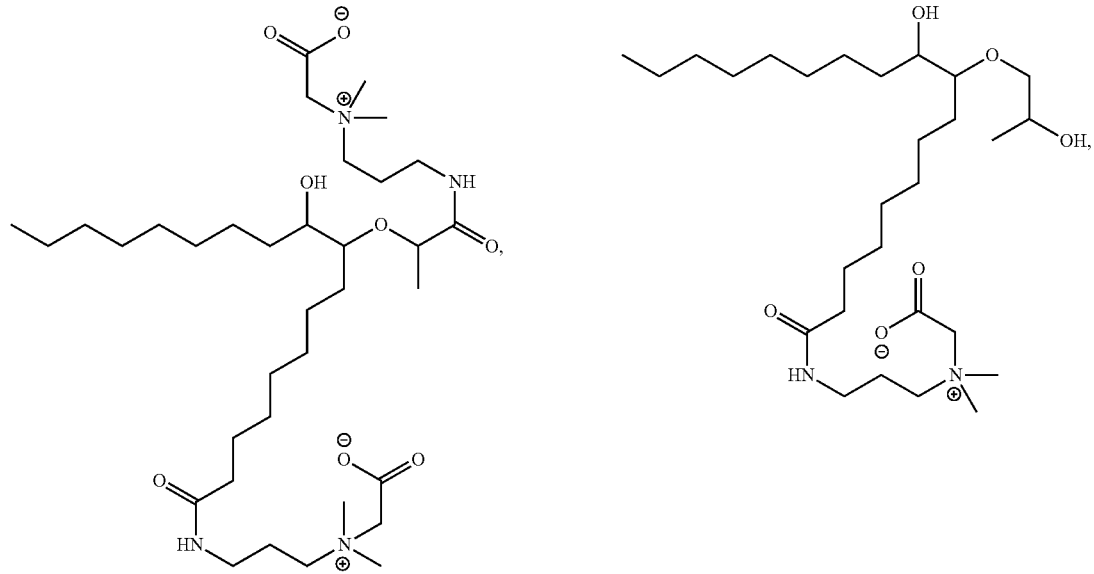

-continued
Candidate 31
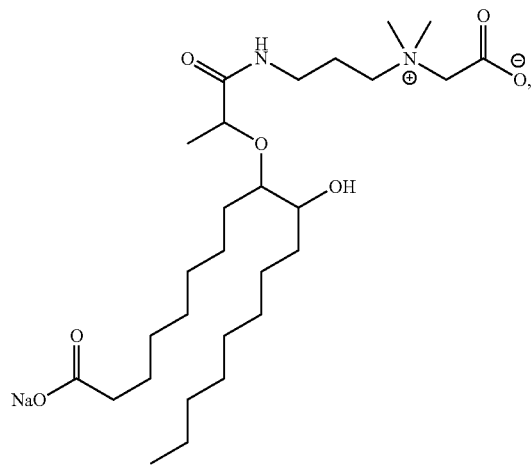
Candidtate 32
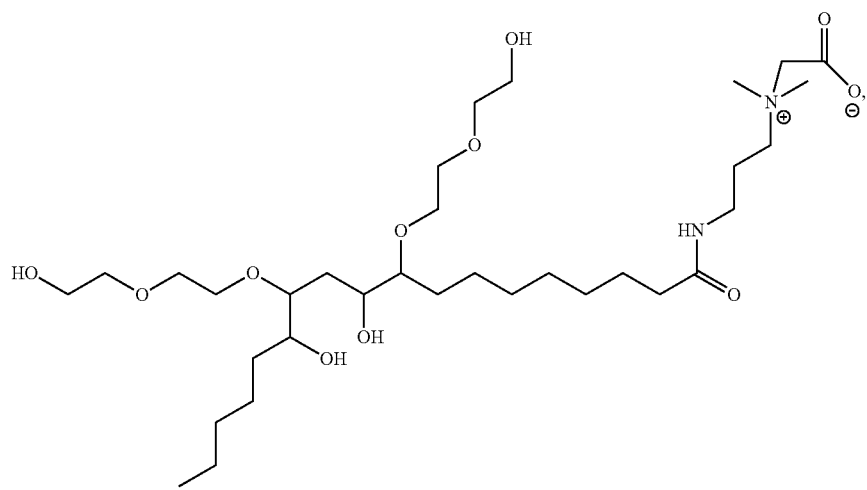
Candidate 34
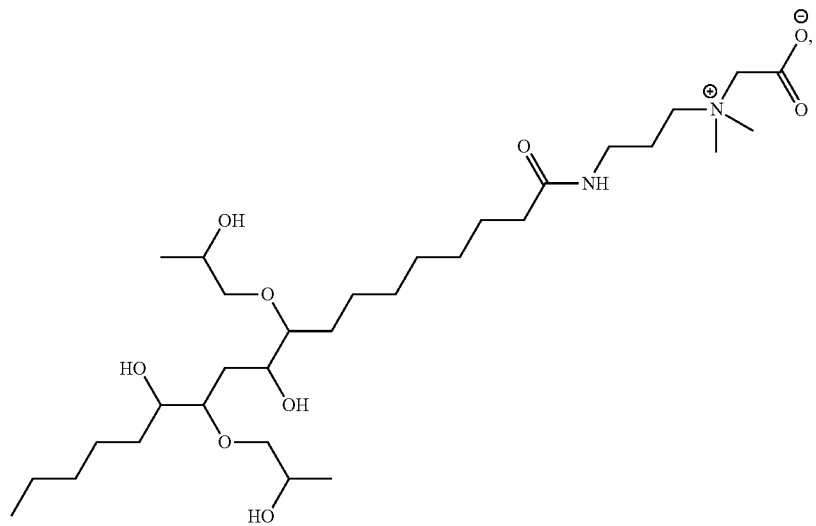

-continued
Candidate 35
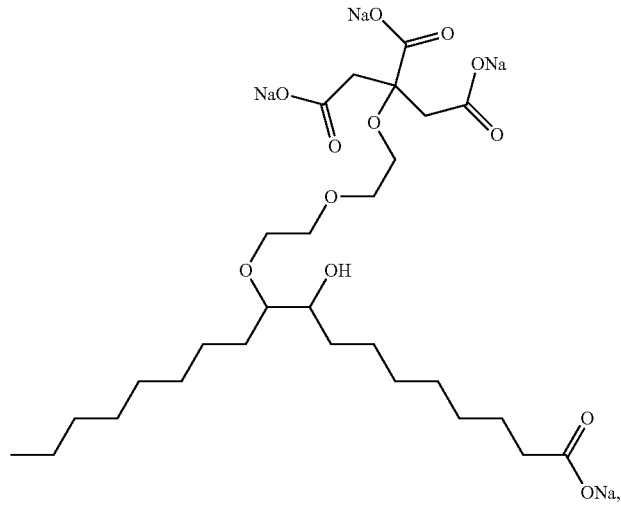
Candidate 36
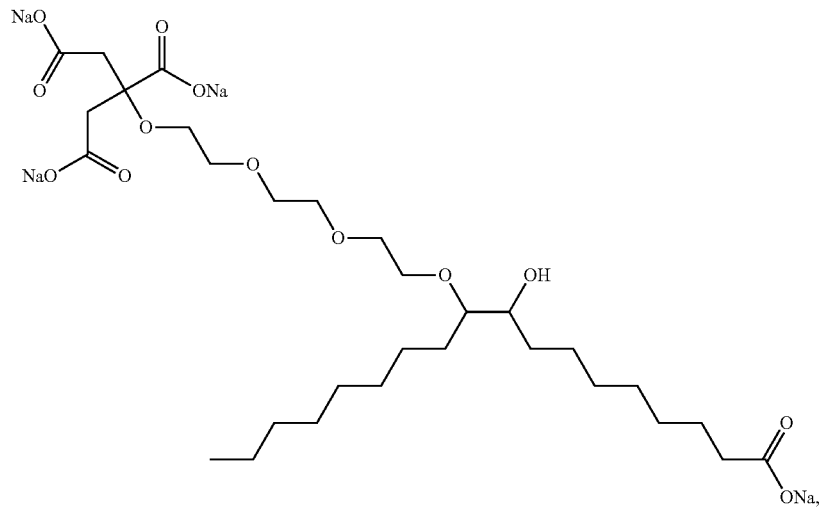
Candidate 37
Candidate 38
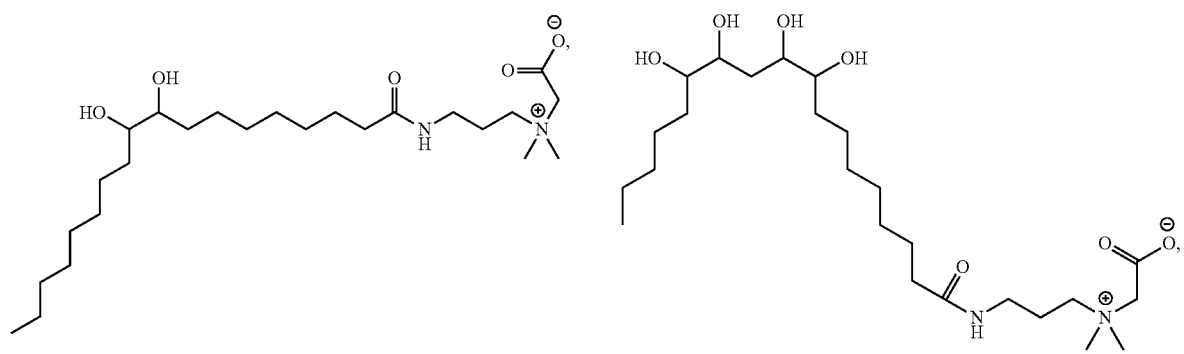

-continued
Candidate 39
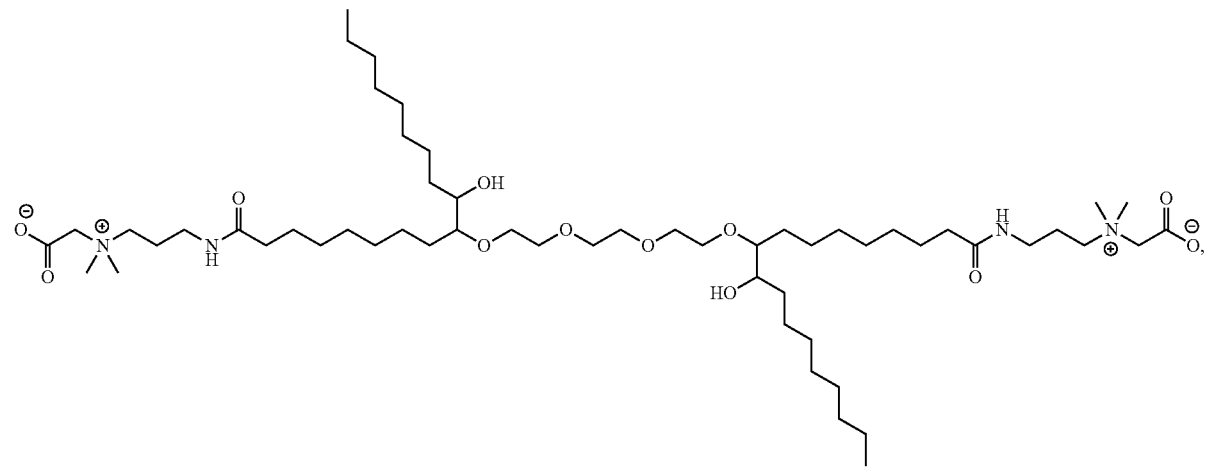
Candidate 40
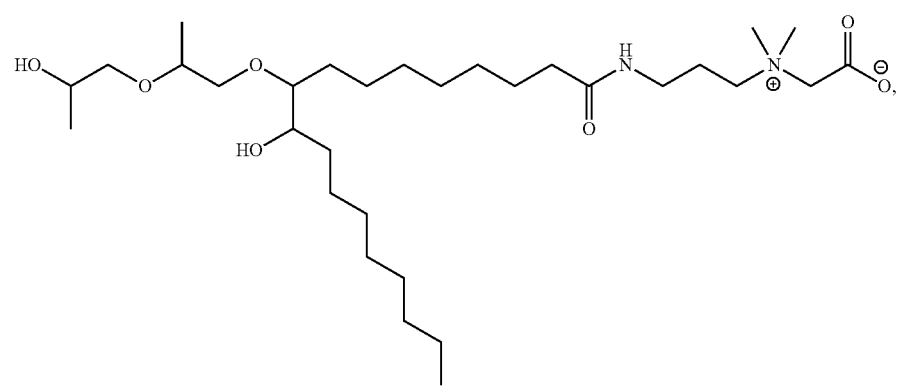
Candidate 41
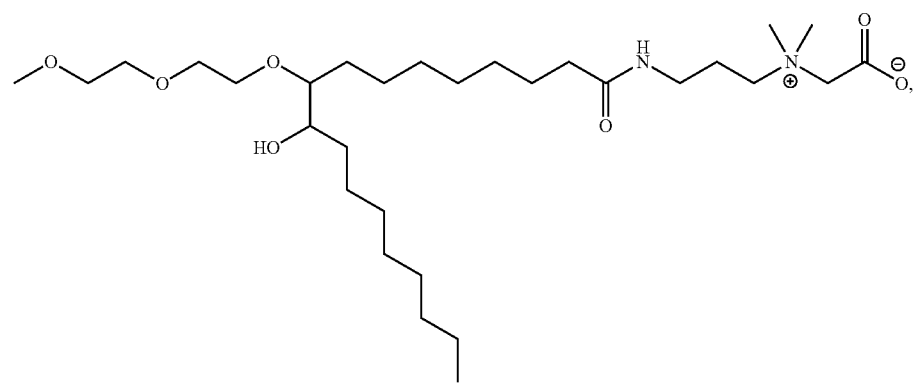

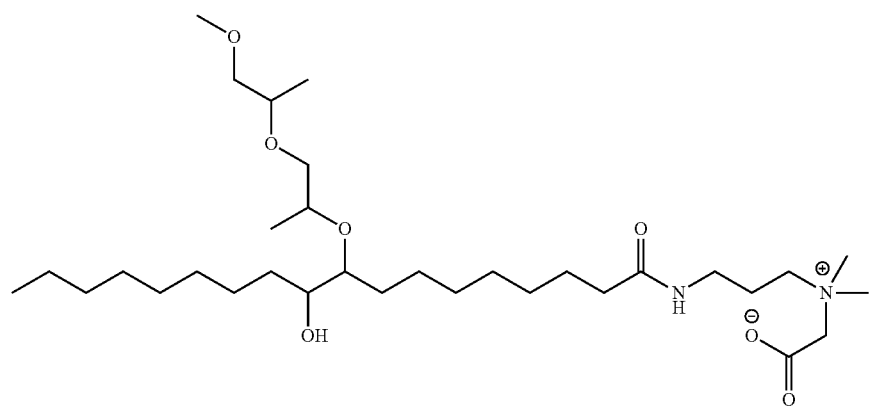
Candidate 42
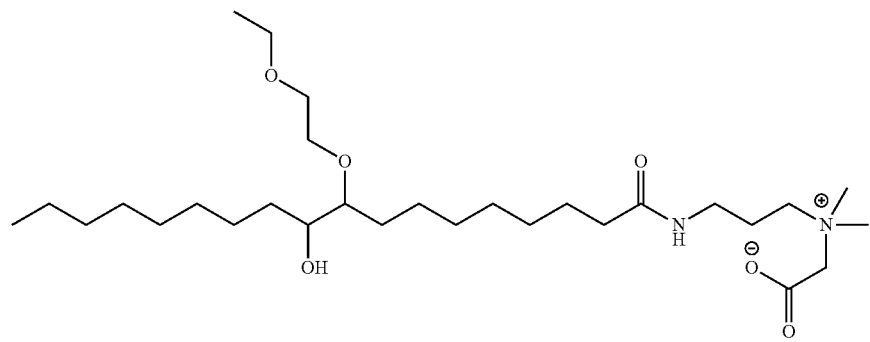
Candidate 43
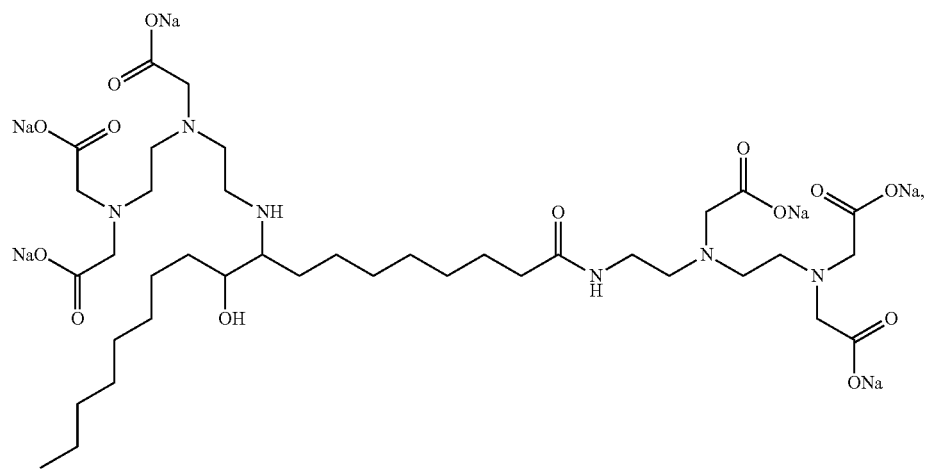
Candidate 44
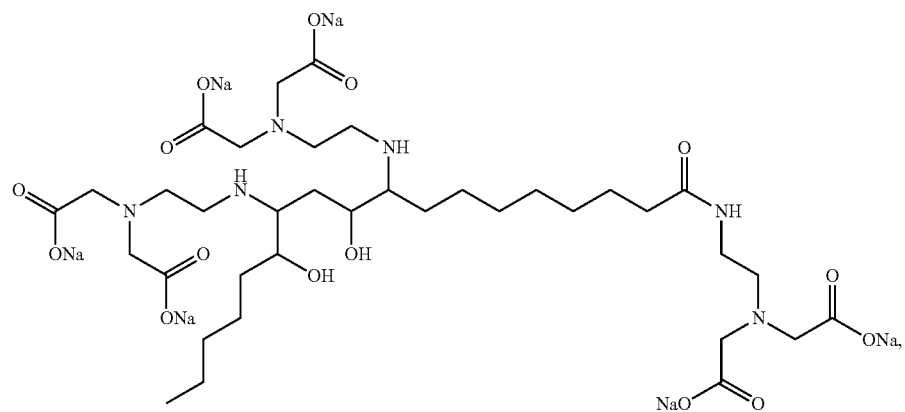
Candidate 45

Candidate 46
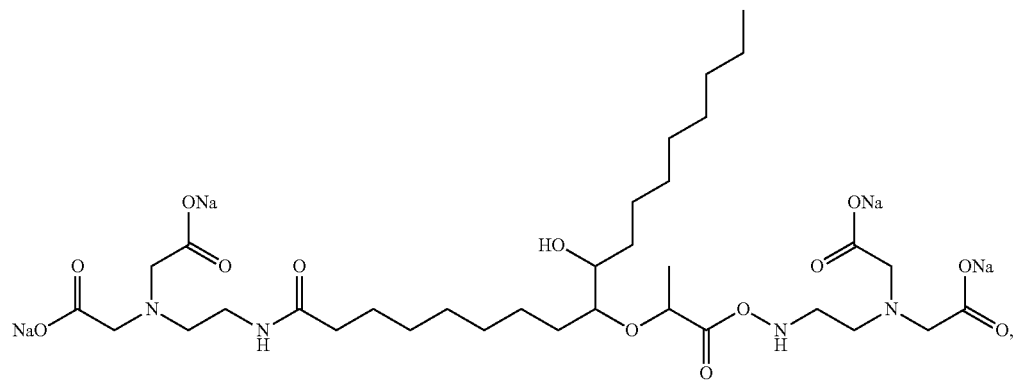
Candidate 47
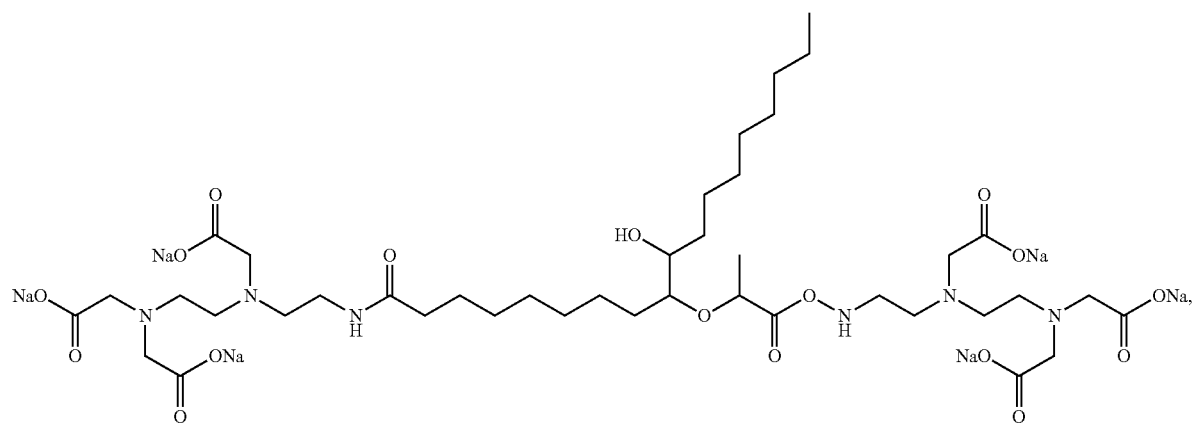
Candidate 50
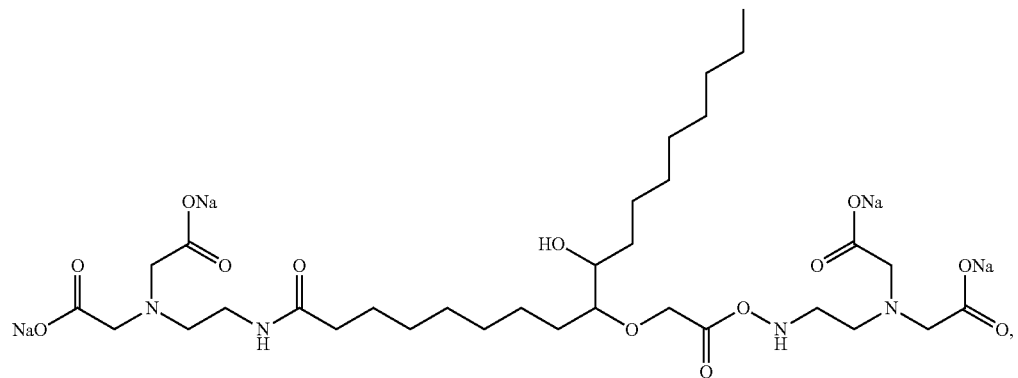
Candidate 51
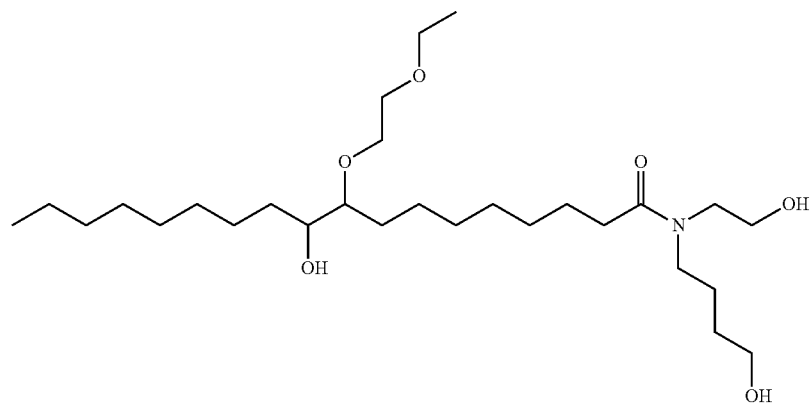

Candidate 52
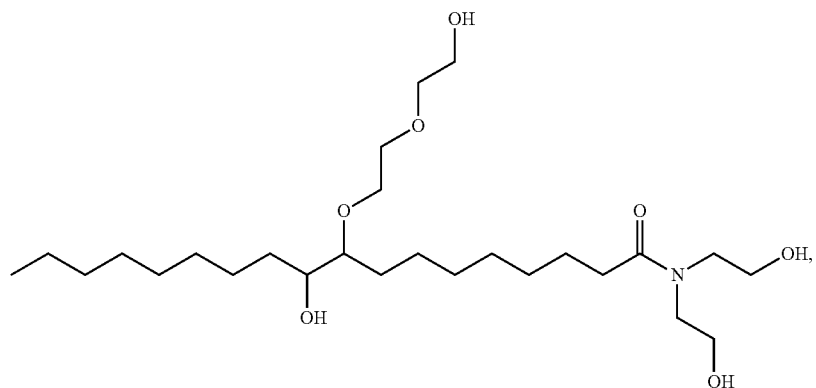
Candidate 53
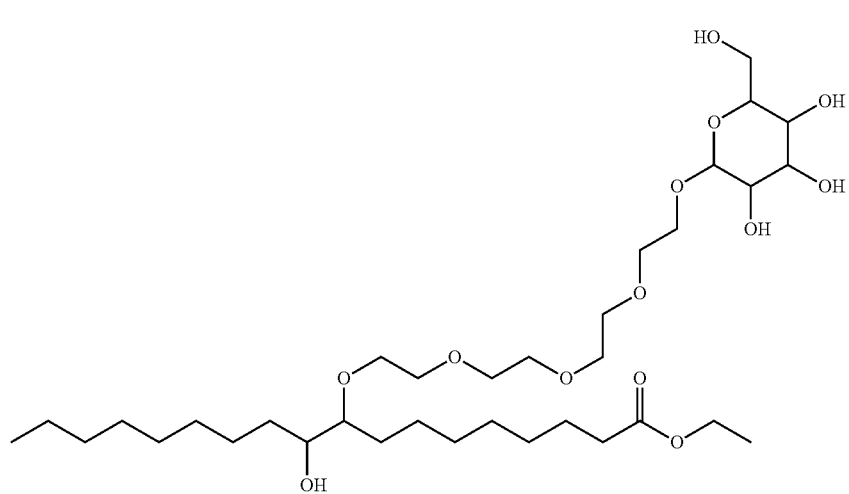
Candidate 54
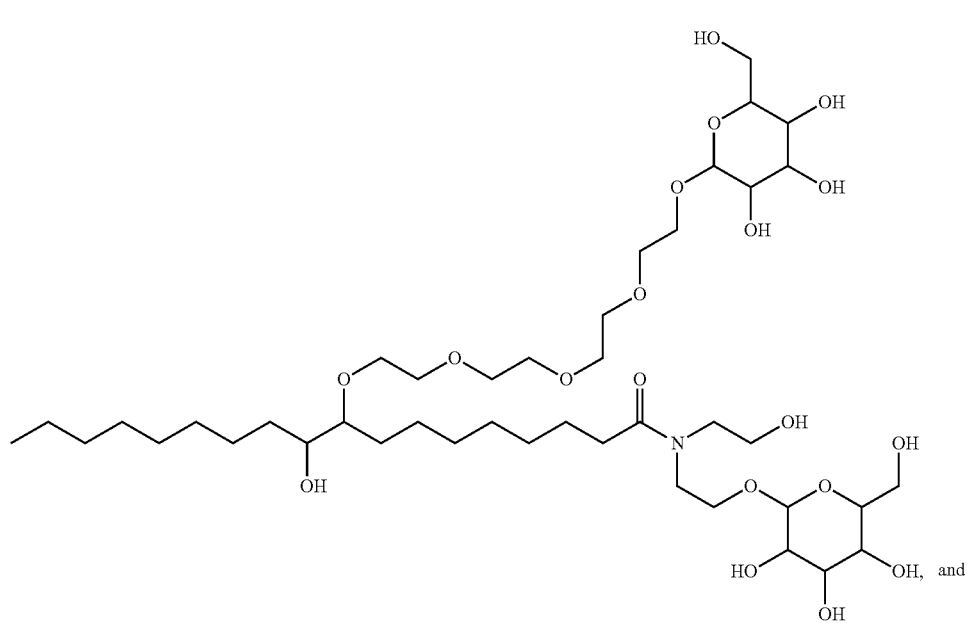

Candidate 55
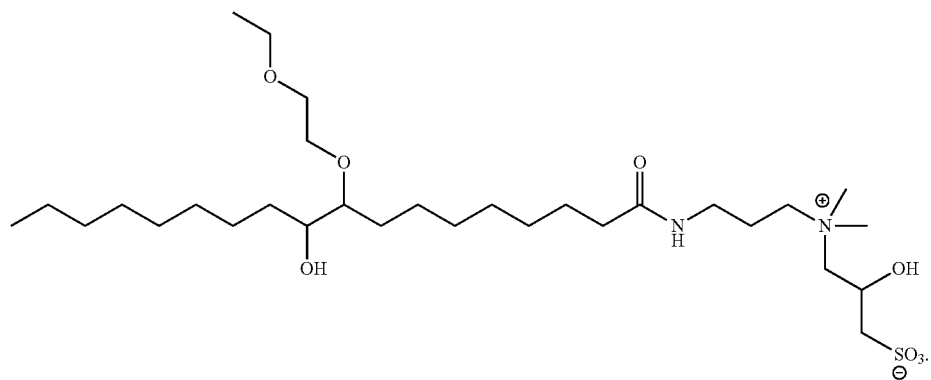
* * * * *